US009040278B2

(12) United States Patent
Cascao-Pereira et al.

(10) Patent No.: US 9,040,278 B2
(45) Date of Patent: *May 26, 2015

(54) **PRODUCTION OF GLUCOSE FROM STARCH USING ALPHA-AMYLASES FROM *BACILLUS SUBTILIS***

(75) Inventors: Luis G. Cascao-Pereira, Redwood City, CA (US); Regina Chin, Palo Alto, CA (US); William A. Cuevas, San Francisco, CA (US); David A. Estell, San Francisco, CA (US); Sang-Kyu Lee, Palo Alto, CA (US); Michael J. Pepsin, Castro Valley, CA (US); Scott D. Power, San Bruno, CA (US); Sandra W. Ramer, Sunnyvale, CA (US); Carol A. Requadt, Tiburon, CA (US); Andrew Shaw, San Francisco, CA (US); Amr R. Toppozada, San Francisco, CA (US); Louise Wallace, Menlo Park, CA (US)

(73) Assignee: DANISCO US INC., Palo Alto, CA (US)

( * ) Notice: Subject to any disclaimer, the term of this patent is extended or adjusted under 35 U.S.C. 154(b) by 922 days.

This patent is subject to a terminal disclaimer.

(21) Appl. No.: 12/478,266

(22) Filed: Jun. 4, 2009

(65) Prior Publication Data

US 2009/0305935 A1    Dec. 10, 2009

Related U.S. Application Data

(60) Provisional application No. 61/059,535, filed on Jun. 6, 2008.

(51) Int. Cl.
| | | |
|---|---|---|
| C12N 9/28 | (2006.01) |
| C12P 19/14 | (2006.01) |
| C12P 7/06 | (2006.01) |
| C08B 37/00 | (2006.01) |
| C07H 21/04 | (2006.01) |
| C12P 19/02 | (2006.01) |
| C11D 3/22 | (2006.01) |
| D06L 1/14 | (2006.01) |
| C11D 3/386 | (2006.01) |

(52) U.S. Cl.
CPC ............... *C12P 19/02* (2013.01); *C11D 3/221* (2013.01); *C12N 9/2417* (2013.01); *D06L 1/14* (2013.01); *Y02E 50/17* (2013.01); *C11D 3/386* (2013.01)

(58) Field of Classification Search
None
See application file for complete search history.

(56) References Cited

U.S. PATENT DOCUMENTS

| | | |
|---|---|---|
| 4,106,991 A | 8/1978 | Markussen et al. |
| 4,435,307 A | 3/1984 | Barbesgaard et al. |
| RE32,153 E | 5/1986 | Tamura et al. |
| 4,587,215 A | 5/1986 | Hirsh |
| 4,661,452 A | 4/1987 | Markussen et al. |
| 5,024,943 A | 6/1991 | Van Ee |
| 5,112,518 A | 5/1992 | Klugkist et al. |
| 5,141,664 A | 8/1992 | Corring et al. |
| 5,240,632 A | 8/1993 | Brumbaugh |
| 5,281,526 A | 1/1994 | Good et al. |
| 5,457,046 A | 10/1995 | Woldike et al. |
| 5,648,263 A | 7/1997 | Schulein et al. |
| 5,686,593 A | 11/1997 | Woldike et al. |
| 5,691,178 A | 11/1997 | Schulein et al. |
| 5,763,254 A | 6/1998 | Woldike et al. |
| 5,776,757 A | 7/1998 | Schulein et al. |
| 5,827,718 A | 10/1998 | Ishida et al. |
| 5,879,920 A | 3/1999 | Dale et al. |
| 5,942,431 A | 8/1999 | Yoneda et al. |
| 6,077,316 A | 6/2000 | Lund et al. |
| 6,287,841 B1 | 9/2001 | Mulleners et al. |
| 6,440,716 B1 | 8/2002 | Svendsen et al. |
| 6,475,762 B1 | 11/2002 | Stafford et al. |
| 7,037,704 B2 | 5/2006 | Dunn-Coleman |
| 7,332,319 B2 | 2/2008 | Baldwin et al. |
| 2004/0018607 A1* | 1/2004 | Callen et al. .................. 435/201 |
| 2006/0014265 A1 | 1/2006 | Ferrari et al. |
| 2006/0134747 A1* | 6/2006 | Baldwin et al. .............. 435/69.1 |
| 2008/0220498 A1 | 9/2008 | Cervin et al. |
| 2009/0305360 A1 | 12/2009 | Breneman et al. |
| 2009/0305935 A1 | 12/2009 | Cascao-Pereira et al. |
| 2010/0003366 A1 | 1/2010 | Cuevas et al. |
| 2010/0015686 A1 | 1/2010 | Cascao-Pereira et al. |

FOREIGN PATENT DOCUMENTS

| | | |
|---|---|---|
| AU | 198776638 A | 3/1988 |
| AU | 198782147 A | 6/1988 |
| CA | 2023529 | 2/1991 |

(Continued)

OTHER PUBLICATIONS

Boel, E. et al. "Glucoamylases G1 and G2 from *Aspergillus niger* are synthesized from two different but closely related mRNAs." *The EMBO Journal* 3(5):1097-1102, 1984.

Cayot, P. et al. "The Quantification of Protein Amino Groups by the Trinitrobenzenesulfonic Acid Method: A Reexamination." *Analytical Biochemistry* 249(2):184-200, 1997.

Chen, H-M et al. "Substitution of asparagine residues in *Aspergillus awamori* glucoamylase by site-directed mutagenesis to eliminate N-glycosylation and inactivation by deamidation." *Biochem. J.* 301(Pt 1):275-281, 1994.

Chen, H.-M et al. "Identification and elimination by site-directed mutagenesis of thermolabile aspartyl bonds in *Aspergillus awamori* glucoamylase." *Protein Eng.* 8(6):575-582, 1995.

(Continued)

*Primary Examiner* — Iqbal H Chowdhury
(74) *Attorney, Agent, or Firm* — Danisco US Inc.

(57) ABSTRACT

An α-amylase from *Bacillus subtilis* (AmyE) produces significant amounts of glucose from various carbohydrate substrates, including vegetable starch, maltoheptaose, and maltotriose. Among other things, this advantageous property allows AmyE or variants thereof to be used in a saccharification reaction having a reduced or eliminated requirement for glucoamylase. The reduction or elimination of the glucoamylase requirement significantly improves the efficiency of the production of ethanol or high fructose corn syrup, for example.

16 Claims, 9 Drawing Sheets

(56) References Cited

FOREIGN PATENT DOCUMENTS

| | | |
|---|---|---|
| CA | 2006687 C | 12/1994 |
| CA | 2202553 A1 | 4/1996 |
| DE | 37 27 911 A1 | 3/1988 |
| DE | 37 41 617 A1 | 7/1988 |
| DE | 38 33 047 A1 | 4/1990 |
| DE | 41 37 470 A1 | 5/1993 |
| DE | 42 05 071 A1 | 8/1993 |
| DE | 42 12 166 A1 | 10/1993 |
| EP | 0 135 138 A2 | 3/1985 |
| EP | 0 214 761 A2 | 3/1987 |
| EP | 0 218 272 A1 | 4/1987 |
| EP | 0 238 023 A2 | 9/1987 |
| EP | 0 238 216 A1 | 9/1987 |
| EP | 0 258 068 A2 | 3/1988 |
| EP | 0 260 105 A2 | 3/1988 |
| EP | 0 271 155 A2 | 6/1988 |
| EP | 0 271 156 A2 | 6/1988 |
| EP | 0 305 216 A1 | 3/1989 |
| EP | 0 318 204 A1 | 5/1989 |
| EP | 0 318 279 A2 | 5/1989 |
| EP | 0 331 376 A2 | 9/1989 |
| EP | 0 346 136 A1 | 12/1989 |
| EP | 0 346 137 A1 | 12/1989 |
| EP | 0 407 225 A1 | 1/1991 |
| EP | 0 414 197 A2 | 2/1991 |
| EP | 0 429 124 A1 | 5/1991 |
| EP | 0 481 547 A1 | 4/1992 |
| EP | 0 495 257 A1 | 7/1992 |
| EP | 0 516 553 A2 | 12/1992 |
| EP | 0 516 554 A2 | 12/1992 |
| EP | 0 516 555 A2 | 12/1992 |
| EP | 0 518 719 A1 | 12/1992 |
| EP | 0 518 720 A1 | 12/1992 |
| EP | 0 518 721 A1 | 12/1992 |
| EP | 0 530 635 A2 | 3/1993 |
| EP | 0 530 870 A1 | 3/1993 |
| EP | 0 533 239 A2 | 3/1993 |
| EP | 0 554 943 A2 | 8/1993 |
| EP | 0 561 446 A2 | 9/1993 |
| EP | 0 561 452 A1 | 9/1993 |
| GB | 1372034 A | 10/1974 |
| GB | 1483591 A | 8/1977 |
| GB | 2200132 A | 7/1988 |
| GB | 2228945 A | 9/1990 |
| GB | 2234980 A | 2/1991 |
| IE | 911797 A1 | 12/1991 |
| JP | 64-074992 | 3/1989 |
| WO | WO 84/02921 A2 | 8/1984 |
| WO | WO 86/01831 A1 | 3/1986 |
| WO | WO 88/02775 A1 | 4/1988 |
| WO | WO 89/01032 A1 | 2/1989 |
| WO | WO 89/06270 A1 | 7/1989 |
| WO | WO 89/06279 A1 | 7/1989 |
| WO | WO 89/09259 A1 | 10/1989 |
| WO | WO 91/16422 A1 | 10/1991 |
| WO | WO 91/17243 A1 | 11/1991 |
| WO | WO 91/17244 A1 | 11/1991 |
| WO | WO 91/18977 A1 | 12/1991 |
| WO | WO 91/19782 A1 | 12/1991 |
| WO | WO 92/00381 A1 | 1/1992 |
| WO | WO 92/01793 A1 | 2/1992 |
| WO | WO 92/05249 A1 | 4/1992 |
| WO | WO 92/06154 A1 | 4/1992 |
| WO | WO 92/06157 A1 | 4/1992 |
| WO | WO 92/08777 A1 | 5/1992 |
| WO | WO 92/17573 A1 | 10/1992 |
| WO | WO 92/19708 A1 | 11/1992 |
| WO | WO 92/19709 A1 | 11/1992 |
| WO | WO 92/19729 A1 | 11/1992 |
| WO | WO 93/04153 A1 | 3/1993 |
| WO | WO93/10210 A1 | 5/1993 |
| WO | WO 93/17089 A1 | 9/1993 |
| WO | WO 93/18129 A1 | 9/1993 |
| WO | WO 93/21297 A1 | 10/1993 |
| WO | WO 93/21299 A1 | 10/1993 |
| WO | WO 93/24618 A1 | 12/1993 |
| WO | WO 93/25651 A1 | 12/1993 |
| WO | WO 94/01541 A1 | 1/1994 |
| WO | WO 94/07998 A1 | 4/1994 |
| WO | WO 94/25578 A1 | 11/1994 |
| WO | WO 94/25583 A1 | 11/1994 |
| WO | WO 95/00636 A1 | 1/1995 |
| WO | WO 95/06720 A1 | 3/1995 |
| WO | WO 95/10602 A1 | 4/1995 |
| WO | WO 95/14783 A1 | 6/1995 |
| WO | WO 95/22615 A1 | 8/1995 |
| WO | WO 95/24471 A1 | 9/1995 |
| WO | WO 95/26397 A1 | 10/1995 |
| WO | WO 95/30744 A2 | 11/1995 |
| WO | WO 95/35381 A1 | 12/1995 |
| WO | WO 96/00292 A1 | 1/1996 |
| WO | WO 96/11262 A1 | 4/1996 |
| WO | WO 96/12012 A1 | 4/1996 |
| WO | WO 96/13580 A1 | 5/1996 |
| WO | WO 96/27002 A1 | 9/1996 |
| WO | WO 96/29397 A1 | 9/1996 |
| WO | WO 96/34108 A2 | 10/1996 |
| WO | WO 97/04079 A1 | 2/1997 |
| WO | WO 97/07202 A1 | 2/1997 |
| WO | WO 98/08940 A1 | 3/1998 |
| WO | WO 98/12307 A1 | 3/1998 |
| WO | WO 98/15257 A1 | 4/1998 |
| WO | WO 98/20115 A1 | 5/1998 |
| WO | WO 98/22613 A1 | 5/1998 |
| WO | WO 99/01544 A1 | 1/1999 |
| WO | WO 99/25846 A2 | 5/1999 |
| WO | WO 99/28448 A1 | 6/1999 |
| WO | WO 99/49740 A1 | 10/1999 |
| WO | WO 00/04136 A1 | 1/2000 |
| WO | WO 01/14629 A1 | 3/2001 |
| WO | WO 01/34899 A1 | 5/2001 |
| WO | WO 02/068589 | 9/2002 |
| WO | WO 2004/091544 | 10/2004 |
| WO | WO 2005/056783 A1 | 6/2005 |
| WO | WO 2005/069849 | 8/2005 |
| WO | WO 2005/111203 A2 | 11/2005 |
| WO | WO 2006/043178 A2 | 4/2006 |
| WO | WO 2006/060062 A2 | 6/2006 |
| WO | 2007145912 A1 | 12/2007 |
| WO | WO 2009/108941 A1 | 9/2009 |
| WO | WO 2009/149395 | 12/2009 |
| WO | WO 2009/149419 | 12/2009 |

OTHER PUBLICATIONS

Chen, H.-M et al. "Effect of replacing helical glycine residues with alanines on reversible and irreversible stability and production of *Aspergillus awamori* glucoamylase." *Protein Eng.* 9(6):499-505, 1996.

Cho, H.-Y. et al. "Molecular characterization of a dimeric intracellular maltogenic amylase of *Bacillus subtilis* SUH4-2." *Biochimica et Biophysica Acta (BBA)—Protein Structure and Molecular Enzymology* 1478(2):333-340, 2000.

Christophersen, C. et al. "Enzymatic Characterisation of Novamyl® a Thermostable α-Amylase." *Starch/Stärke* 50(1):39-45, 1998.

Cleland, J. et al. "Baumé-Dry Substance Tables for Starch Suspensions." *Industrial & Engineering Chemistry Analytical Edition* 15(5):334-336, 1943.

Conti, M. et al. "Capillary isoelectric focusing: the problem of protein solubility." *Journal of Chromatography A* 757(1-2):237-245, 1997.

Dartois, V. et al. "Cloning, nucleotide sequence and expression in *Escherichia coli* of a lipase gene from *Bacillus subtilis* 168." *Biochimica et Biophysica Acta* 1131(3):253-260, 1992.

Engelen, A.J. et al. "Simple and rapid determination of phytase activity." *Journal of AOAC International* 77(3):760-764, 1994.

Fierobe, H-P et al. "Mutational Modulation of Substrate Bond-Type Specificity and Thermostability of Glucoamylase from *Aspergillus awamori* by Replacement with Short Homologue Active Site Sequences and Thiol/Disulfide Engineering." *Biochemistry* 35(26):8696-8704, 1996.

(56) References Cited

OTHER PUBLICATIONS

Fogarty, W.M. et al. "Starch degrading enzymes of microbial origin." *Progress in Industrial Microbiology* 15:87-150, particularly 112-115, 1979.

Fujimoto, Z. et al. "Crystal structure of a catalytic-site mutant [alpha]-amylase from *Bacillus subtilis* complexed with maltopentaose." *Journal of Molecular Biology* 277(2):393-407, 1998.

Hata, Y. et al. "The glucoamylase cDNA from *Aspergillus oryzae*: its cloning, nucleotide sequence, and expression in *Saccharomyces cerevisiae*." *Agric. Biol. Chem.* 55(4):941-949, 1991.

Kagawa, M. et al. "Crystal Structure of *Bacillus subtilis* alpha-Amylase in Complex with Acarbose." *J. Bacteriol.* 185(23):6981-6984, 2003.

Kaushik, J.K. et al. "Why Is Trehalose an Exceptional Protein Stabilizer?: An analysis of the thermal stability of proteins in the presence of the compatible osmolyte trehalose." *J. Biol. Chem.* 278(29):26458-26465, 2003.

Lassmann, T. et al. "Kalign—an accurate and fast multiple sequence alignment algorithm." *BMC Bioinformatics* 6(1):298, 2005.

Li, Y. et al. "Effect of introducing proline residues on the stability of *Aspergillus awamori*." *Protein Eng.* 10(10):1199-1204, 1997.

MacGregor, E.A. et al. "Relationship of sequence and structure to specificity in the alpha-amylase family of enzymes." *Biochimica et Biophysica Acta (BBA)—Protein Structure and Molecular Enzymology* 1546(1):1-20, 2001.

McKenzie, T. et al. "The nucleotide sequence of pUB110: some salient features in relation to replication and its regulation." *Plasmid* 15(2):93-103, 1986.

Morris, M.A. et al. "The Effect of Wash Temperature on Removal of Particulate and Oily Soil from Fabrics of Varying Fiber Content." *Textile Research Journal* 52(4):280-286, 1982.

Ohdan, K. et al. "Characteristics of Two Forms of alpha-Amylases and Structural Implication." *Appl. Environ. Microbiol.* 65(10):4652-4658, 1999.

Yang, M. et al. "Nucleotide sequence of the amylase gene from *Bacillus subtilis*." *Nucl. Acids Res.* 11(2):237-249, 1983.

Database UnitPort p. 1 1998, Ohdan et al: "Characteristic of two of alpha-amylases and structural implication", Database accession No. 082953.

Database UnitProt pp. 1-5 1986, Various Authors: "various titles". Database accession No. P00691.

Database UnitProt p. 1, Jan. 2008 Xin et al: "Cloning and expression of *Bacillus subtilis* FS321 alpha-amylase gene", Database accession No. A8W7J1.

De Moraes et al. "development of yeast strains for the efficient utilization of starch: evaluation of constructs that express alpha-amylase and glucoamylase separately or bifunctional fusion proteins", Applied Microbiology and Biotechnology, vol. 43, 1995, pp. 1067-1076.

Fujimoto et al. "Crystal structure of a catalytic-site mutant alpha-amylase from *Bacillus subtilis* complexed with maltopentaose", Journal of Molecular Biology, vol. 277, 1998, pp. 393-407.

Hayashida et al. "Production and characteristics of raw-potato-starch-digesting alpha-amylase from *Bacillus subtilis* 65", Applied and Environmental Microbiology, vol. 54, 1988, pp. 1516-1522.

Konsoula et al. "Alpha-amylases and glucoamylases free or immobilized in calcium alginate gel capsules for synergistic hydrolysis of crude starches", Amino Acids, vol. 33, 2007, pp. XIII.

Liu et al. "A novel raw starch digesting alpha-amylase from a newly isolated *Bacillus* sp. YX-1: Purification and characterization", Bioresource Technology, vol. 99, Oct. 24, 2007 pp. 4315-4320.

Sodhi et al. "Production of a thermostable alpha-amylase from *Bacillus* sp. PS-7 by solid state fermentation and its synergistic use in the hydrolysis of malt starch for alcohol production", Process Biochemistry, vol. 40, 2005.

Yeesang et al. "Sago starch as a low-cost carbon source for exopolysaccharide production by *Lactobacillus kefiranofaciens*" World Journal of Microbiology and Biotechnology, vol. 24, Nov. 15, 2007, pp. 1195-1201.

PCT Search Report for PCT Application No. PCT/US2009/046296, mailed Nov. 10, 2009.

PCT Search Report for PCT Application No. PCT/US2009/046279, 3 pages.

& Database UniProt [Online] Jul. 21, 1986, "RecName: Full=Alpha-amylase; EC=<AHREF="http://srs.ebi.ac.uk/srsbin/cgi-bin/wgetz?[enzyme-ECNumber:3.2.1.1]+-e">3.2.1.1</A>; AltName: Full=1,4-alpha-D-glucan glucanohydrolase; Flags: Precursor;" retrieved from EBI accession No. UNIPROT:P00691 Database accession No. P00691 compound.

& Database UniProt [Online] May 1, 2000, "SubName: Full=Alpha-amylase;" retrieved from EBI accession No. UNIPROT:Q9R9H7.

Barbe et al. "From a consortium sequence to a unified sequence: the *Bacillus subtillis* 168 reference genome a decade later," Microbiology 2009, 155 (PT 6), pp. 1758-1775.

Broun et al, Catalytic plasticity of fatty acid modification enzymes underlying chemical diversity of plant lipids. Science, 1998, vol. 282: 1315-1317.

Chica et al., Semi-rational approaches to engineering enzyme activity: combining the benefits of directed evolution and rational design. Curro Opi. Biotechnol., 2005, vol. 16: 378-384.

Cho et al., "Molecular characterization of a dimeric intracellular maltogenic amylase of *Bacillus subtilis* SUH4-2", Biochemica et Biophysica Acta 1478 (2000), pp. 333-340.

Devos et al., Practical limits of function prediction. Proteins: Structure, Function, and Genetics. 2000, vol. 41: 98-107.

Eichenberger et al, "The program of gene transcription for a single differentiating cell type during sporulation in *Bacillus subtillis*" PLoS biol. 2(10), E328 (2004).

Emori et al., "Molecular Cloning, Nucleotide Sequencing, and Expression of the *Bacillus subtilis* (*natto*) IAM1212 α-Amylase Gene, Which Encodes an α-Amylase Structurally Similar to but Enzymatically Distinct from That of *B. subtilis* 2633," *J. Bacteriol.* (1990) 172(9): 4901-08.

Freire, E. (1995) Differential Scanning Calorimetry Methods. Mol. Biol. 41:191-218.

GenBank: ABK54355.1. Printed Jan. 27, 2012. http://www.ncbi.nlm.nih.gov/protein/117650733?report=genbank&log$=protalign&blast_rank=5&RID=HHEG2BRJ01N.

GenBank: ABS72727.1. Printed Jan. 27, 2012. http://www.ncbi.nlm.nih.gov/protein/154350648?report=genbank&log$=protalign&blast_rank=17&RID=HHEG2BRJ01N.

GenBank: ABW34932.1. Printed Jan. 27, 2012. http://www.ncbi.nlm.nih.gov/protein/158342342?report=genbank&log$=protalign&blast_rank=33&RID=HHEG2BRJ01N.

GenBank: ABW75769.1. Printed Jan. 27, 2012. http://www.ncbi.nlm.nih.gov/protein/158633403?report=genbank&log$=protalign&blast_rank=7&RID=HHEG2BRJ01N.

GenBank: ABY73736.1. Printed Jan. 27, 2012. http://www.ncbi.nlm.nih.gov/protein/165909652?report=genbank&log$=protalign&blast_rank=21&RID=HHEG2BRJ01N.

GenBank: ACD93218.3. Printed Jan. 27, 2012. http://www.ncbi.nlm.nih.gov/protein/288915565?report=genbank&log$=protalign&blast_rank=15&RID=HHEG2BRJ01N.

GenBank: ACK37366.1. Printed Jan. 27, 2012. http://www.ncbi.nlm.nih.gov/protein/217315807?report=genbank&log$=protalign&blast_rank=30&RID=HHEG2BRJ01N.

GenBank: ACM91731.1. Printed Jan. 27, 2012.

GenBank: ACU57501.1. Printed Jan. 27, 2012. http://www.ncbi.nlm.nih.gov/protein/256033945?report=genbank&log$=protalign&blast_rank=36&RID=HHEG2BRJ01N.

GenBank: ADB81848.1. Printed Jan. 27, 2012. http://www.ncbi.nlm.nih.gov/protein/284178231?report=genbank&log$=protalign&blast_rank=19&RID=HHEG2BRJ01N.

GenBank: ADF47479.1. Printed Jan. 27, 2012. http://www.ncbi.nlm.nih.gov/protein/294906521?report=genbank&log$=protalign&blast_rank=18&RID=HHEG2BRJ01N.

GenBank: ADH93703.1. Printed Jan. 27, 2012. http://www.ncbi.nlm.nih.gov/protein/296933182?report=genbank&log$=protalign&blast_rank=4&RID=HHEG2BRJ01N.

GenBank: ADH93704.1. Printed Jan. 27, 2012. http://www.ncbi.nlm.nih.gov/protein/296933184?report=genbank&log$=protalign&blast_rank=2&RID=HHEG2BRJ01N.

(56) References Cited

OTHER PUBLICATIONS

GenBank: ADH93705.1. Printed Jan. 27, 2012. http://www.ncbi.nlm.nih.gov/protein/296933186?report=genbank&log$=protalign&blast_rank=3&RID=HHEG2BRJ01N.
GenBank: ADH93706.1. Printed Jan. 27, 2012. http://www.ncbi.nlm.nih.gov/protein/296933188?report=genbank&log$=protalign&blast_rank=10&RID=HHEG2BRJ01N.
GenBank: ADH93707.1. Printed Jan. 27, 2012. http://www.ncbi.nlm.nih.gov/protein/296933190?report=genbank&log$=protalign&blast_rank=24&RID=HHEG2BRJ01N.
GenBank: ADM36368.1. Printed Jan. 27, 2012. http://www.ncbi.nlm.nih.gov/protein/305411249?report=genbank&log$=protalign&blast_rank=14&RID=HHEG2BRJ01N.
GenBank: ADV95234.1. Printed Jan. 27, 2012. http://www.ncbi.nlm.nih.gov/protein/320020248?report=genbank&log$=protalign&blast_rank=1&RID=HHEG2BRJ01N.
GenBank: AEP85220.1. Printed Jan. 27, 2012. http://www.ncbi.nlm.nih.gov/protein/349597432?report=genbank&log$=protalign&blast_rank=13&RID=HHEG2BRJ01N.
GenBank: AEP89368.1. Printed Jan. 27, 2012. http://www.ncbi.nlm.nih.gov/protein/349593181?report=genbank&log$=protalign&blast_rank=9&RID=HHEG2BRJ01N.
GenBank: AL009126.3 region 90537-92086. Printed Jan. 27, 2012.
GenBank: BAA08938.1. Printed Jan. 27, 2012. http://www.ncbi.nlm.nih.gov/protein/1805376?report=genbank&log$=protalign&blast_rank=12&RID=HHEG2BRJ01N.
GenBank: BAA31528.1. Printed Jan. 27, 2012. http://www.ncbi.nlm.nih.gov/protein/3298505?report=genbank&log$=protalign&blast_rank=23&RID=HHEG2BRJ01N.
GenBank: BAI83766.1. Printed Jan. 27, 2012. http://www.ncbi.nlm.nih.gov/protein/291482691?report=genbank&log$=protalign&blast_rank=31&RID=HHEG2BRJ01N.
GenBank: CAA23437.1. Printed Jan. 27, 2012. http://www.ncbi.nlm.nih.gov/protein/39794?report=genbank&log$=protalign&blast_rank=12&RID=HHEG2BRJ01N.
GenBank: CAA26086.1. Printed Jan. 27, 2012. http://www.ncbi.nlm.nih.gov/protein/39796?report=genbank&log$=protalign&blast_rank=29&RID=HHEG2BRJ01N.
GenBank: CAA30643.1. Printed Jan. 27, 2012. http://www.ncbi.nlm.nih.gov/protein/39790?report=genbank&log$=protalign&blast_rank=28&RID=HHEG2BRJ01N.
GenBank: CAB12098.2. Printed Jan. 27, 2012. http://www.ncbi.nlm.nih.gov/protein/225184709?report=genbank&log$=protalign&blast_rank=1&RID=HHEG2BRJ01N.
GenBank: CAJ01439.1. Printed Jan. 27, 2012. http://www.ncbi.nlm.nih.gov/protein/67624833?report=genbank&log$=protalign&blast_rank=38&RID=HHEG2BRJ01N.
GenBank: CCF03805.1. Printed Jan. 27, 2012. http://www.ncbi.nlm.nih.gov/protein/371566955?report=genbank&log$=protalign&blast_rank=20&RID=HHEG2BRJ01N.
GenBank: EFG90830.1. Printed Jan. 27, 2012. http://www.ncbi.nlm.nih.gov/protein/296149941?report=genbank&log$=protalign&blast_rank=14&RID=HHEG2BRJ01N.
GenBank: EHA28753.1. Printed Jan. 27, 2012. http://www.ncbi.nlm.nih.gov/protein/351468537?report=genbank&log$=protalign&blast_rank=1&RID=HHEG2BRJ01N.
GenBank: EHM06463.1. Printed Jan. 27, 2012. http://www.ncbi.nlm.nih.gov/protein/363726325?report=genbank&log$=protalign&blast_rank=22&RID=HHEG2BRJ01N.
Gene ID: 11238201. Printed Jan. 27, 2012. http://www.ncbi.nlm.nih.gov/sites/entrez?db=gene&cmd=search&term=11238201&RID=HHEG2BRJ01N&log$=geneexplicitprot&blast_rank=13.
Gene ID: 5462160. Printed Jan. 27, 2012. http://www.ncbi.nlm.nih.gov/sites/entrez?db=gene&cmd=search&term=5462160&RID=HHEG2BRJ01N&log$=geneexplicitprot&blast_rank=17.
Kunamneni, A., et al. "Response surface optimizationof enzymatic hydrolysis of maize starch for higher glucose production" *Bichem Eng J*:27 (2005) pp. 179-190.
Kunst et al, "The complete genome sequence of the gram-positive bacterium *Bacillius subtillis*" Nature 390(6667), pp. 249-256 (1997).

Mäntsälä et al., "Membrane-bound and Soluble Extracellular α-Amylase from *Bacillus subtilis*," *J. Biol. Chem.* (1979) 254(17): 8540-47.
Mizuno et al., "Systematic sequence olthe 263 kb 210 degrees-232 degrees region of the *Bacillus subtilis* genome containing ihe skin element and many sporulation genes",iMicrobiology 142 (PT 111), pp. 3103-3111 (1996); NCBI Genome Projeci, "Oirect Submission", submitted (Aug. 12, 2009) Nationai Ceriterfor Biotechnology Information, NIH,Bethesda, MD 20894, USA.
Mizuno H. et al,. "Crystallization and preliminary X-ray studies of wild type and catalytic-site mutant alpha-amylase from *Bacillus subtillis*," J Mol Biol. Dec. 20, 1993 234(4). pp. 1282-1283.
NCBI Reference Sequence: NP_388186.2. Printed Jan. 27, 2012. http://www.ncbi.nlm.nih.gov/protein/255767082?report=genbank&log$=protalign&blast_rank=1&RID=HHEG2BRJ01N.
NCBI Reference Sequence: YP_001419958.1. Printed Jan. 27, 2012. http://www.ncbi.nlm.nih.gov/protein/154684797?report=genbank&log$=protalign&blast_rank=17&RID=HHEG2BRJ01N.
NCBI Reference Sequence: YP_003864677.1. Printed Jan. 27, 2012. http://www.ncbi.nlm.nih.gov/protein/305673005?report=genbank&log$=protalign&blast_rank=14&RID=HHEG2BRJ01N.
NCBI Reference Sequence: YP_004206261.1. Printed Jan. 27, 2012. http://www.ncbi.nlm.nih.gov/protein/321313974?report=genbank&log$=protalign&blast_rank=1&RID=HHEG2BRJ01N.
NCBI Reference Sequence: YP_004875852.1. Printed Jan. 27, 2012. http://www.ncbi.nlm.nih.gov/protein/350264545?report=genbank&log$=protalign&blast_rank=13&RID=HHEG2BRJ01N.
NCBI Reference Sequence: ZP_03598671.1. Printed Jan. 27, 2012. http://www.ncbi.nlm.nih.gov/protein/221317377?report=genbank&log$=protalign&blast_rank=11&RID=HHEG2BRJ01N.
NCBI Reference Sequence: ZP_06875121.1. Printed Jan. 27, 2012. http://www.ncbi.nlm.nih.gov/protein/296332661?report=genbank&log$=protalign&blast_rank=14&RID=HHEG2BRJ01N.
Orlando et al., "The purification of a novel amylase from *Bacillus subtilis* and its inhibition by wheat proteins," *Biochem. J.* (1983) 209: 561-64.
PDB: 1BAG_A. Printed Jan. 27, 2012. http://www.ncbi.nlm.nih.gov/protein/157830193?report=genbank&log$=protalign&blast_rank=35&RID=HHEG2BRJ01N.
PDB: 1 UA7_A. Printed Jan. 27, 2012. http://www.ncbi.nlm.nih.gov/protein/49259314?report=genbank&log$=protalign&blast_rank=37&RID=HHEG2BRJ01N.
PDB: 3DCO_A. Printed Jan. 27, 2012. http://www.ncbi.nlm.nih.gov/protein/190613740?report=genbank&log$=protalign&blast_rank=39&RID=HHEG2BRJ01N.
PRF: 226106. Printed Jan. 27, 2012. http://www.ncbi.nlm.nih.gov/protein/226106?report=genbank&log$=protalign&blast_rank=28&RID=HHEG2BRJ01N.
PRF: 352984. Printed Jan. 27, 2012. http://www.ncbi.nlm.nih.gov/protein/352984?report=genbank&log$=protalign&blast_rank=32&RID=HHEG2BRJ01N.
Rumbak et al. (J. Bacteriology, vol. 173, pp. 4203-4211, 1991).
Seffernick et al., Melamine deaminase and Atrazine chlorohydrolase: 98 percent identical but functionally different. J. Bacteriol., 2001, vol. 183 (8): 2405-2410.
Sen et al., Developments in directed evolution for improving enzyme functions. Appl. Biochem. Biotechnol., 2007, vol. 143: 212-223.
Swiss-Prot: P00691.2. Printed Jan. 27, 2012. http://www.ncbi.nlm.nih.gov/protein/239938593?report=genbank&log$=protalign&blast_rank=1&RID=HHEG2BRJ01N.
Whisstock et al., Prediction of protein function from protein sequence. Q. Rev. Biophysics., 2003, vol. 36 (3): 307-340.
Witkowski et al., Conversion of b-ketoacyl synthase to a Malonyl Decarboxylase by replacement of the active cysteine with glutamine. Biochemistry, 1999, vol. 38: 11643-11650.

(56) References Cited

OTHER PUBLICATIONS

Written Opinion of the International Search Authority for PCT/US2009/046506 dated Dec. 6, 2010.

Yamazaki et al., "α-Amylase Genes (*amyR2 and amyE*+) from an α-Amylase-Hyperproducing *Bacillus subtilis* Strain: Molecular Cloning and Nucleotide Sequences", Journal of Bacteriology, Oct. 1983, pp. 327-337.

\* cited by examiner

FIG. 1

```
AmyE_FL     1   LTAPSIKSGTILHAWNWSFNTLKHNMKDIHDAGYTAIQTSPINQVKEGNQGDKSMSNWYW
Amy31A     42   VTASSVKNGTILHAWNWSFNTLTQNMKDIRDAGYAAIQTSPINQVKEGNQGDKSMSNWYW

AmyE_FL    61   LYQPTSYQIGNRYLGTEQEFKEMCAAAEEYGIKVIVDAVINHTTSDYAAISNEVKSIPNW
Amy31A    102   LYQPTSYQIGNRYLGTEQEFKDMCAAAEKYGVKVIVDAVVNHTTSDYGAISDEIKRIPNW

AmyE_FL   121   THGNTQIKNWSDRWDVTQNSLLGLYDWNTQNTQVQSYLKRFLDRALNDGADGFRFDAAKH
Amy31A    162   THGNTQIKNWSDRWDITQNALLGLYDWNTQNTEVQAYLKGFLERALNDGADGFRYDAAKH

AmyE_FL   181   IELPDDGSYGSQFWPNITNTSAEFQYGEILQDSASRDAAYANYMDVTASNYGHSIRSALK
Amy31A    222   IELPDDGNYGSQFWPNITNTSAEFQYGEILQDSASRDTAYANYMNVTASNYGHSIRSALK

AmyE_FL   241   NRNLGVSNISHYASDVSADKLVTWVESHDTYANDDEESTWMSDDDIRLGWAVIASRSGST
Amy31A    282   NRILSVSNISHYASDVSADKLVTWVESHDTYANDDEESTWMSDDDIRLGWAVIGSRSGST

AmyE_FL   301   PLFFSRPEGGGNGVRFPGKSQIGDRGSALFEDQAITAVNRFHNVMAGQPEELSNPNGNNQ
Amy31A    342   PLFFSRPEGGGNGVRFPGKSQIGDRGSALFKDQAITAVNQFHNEMAGQPEELSNPNGNNQ

AmyE_FL   361   IFMNQRGSHGVVLANAGSSSVSINTATKLPDGRYDNKAGAGSFQVNDGKLTGTINARSVA
Amy31A    402   IFMNQRGSKGVVLANAGSSSVTINTSTKLPDGRYDNRAGAGSFQVANGKLTGTINARSAA

AmyE_FL   421   VLYPDDIAKAPHVFLENYKTGVTHSFNDQLTITLRADANTTKAVYQINNGPETAFKDGDQ
Amy31A    462   VLYPDDIGNAPHVFLENYQTEAVHSFNDQLTVTLRANAKTTKAVYQINNGQETAFKDGDR

AmyE_FL   481   FTIGKGDPFGKTYTIMLKGTNSDGVTRTEKYSFVKRDPASAKTIGYQNPNHWSQVNAYIY
Amy31A    522   LTIGKEDPIGTTYNVKLTGTNGEGASRTQEYTFVKKDPSQTNIIGYQNPDHWGNVNAYIY

AmyE_FL   541   KHDGSRVIELTGSWPGKPMTKNADGIYTLTLPADTDTTNAKVIFNNGSAQVPGQNQPGFD
Amy31A    582   KHDGGGAIELTGSWPGKAMTKNADGIYTLTLPANADTADAKVIFNNGSAQVPGQNHPGFD

AmyE_FL   601   YVLNGLYNDSGLSGSLPH (SEQ ID NO: 1)
Amy31A    642   YVQNGLYNNSGLNGYLPH (SEQ ID NO: 25; note that this is
equivalent to SEQ ID NO: 3 without the signal sequence)
```

PRODUCTION OF GLUCOSE FROM STARCH USING ALPHA-AMYLASES FROM *BACILLUS SUBTILIS*

CROSS-REFERENCE

This application claims priority to U.S. Provisional Patent Application Ser. No. 61/059,535 filed Jun. 6, 2008, which is incorporated herein by reference.

SEQUENCE LISTING

A sequence listing comprising SEQ ID NOS: 1-24 is attached and incorporated herein by reference in its entirety.

FIELD OF THE INVENTION

Alpha-amylases from *Bacillus subtilis* (AmyE), variants thereof, nucleic acids encoding the same, and host cells comprising the nucleic acids are provided. Methods of using AmyE or variants thereof are disclosed, including liquefaction and/or saccharification of starch, among others. Such methods may yield sugars useful for ethanol production or high fructose corn syrup production, for example.

BACKGROUND

Vegetable starches, e.g., cornstarch, are widely used in the industrial manufacture of products such as syrups and biofuels. For example, high fructose corn syrup (HFCS) is a processed form of corn syrup having high fructose content and a sweetness comparable to sugar, making HFCS useful as a sugar substitute in soft drinks and other processed foods. HFCS production currently represents a billion dollar industry. The production of ethanol as a biofuel is also a growing industry.

Syrups and biofuels can be produced from starch by an enzymatic process that catalyzes the breakdown of starch into glucose. This enzymatic process typically involves a sequence of enzyme-catalyzed reactions:

(1) Liquefaction: α-Amylases (EC 3.2.1.1) first catalyze the degradation of a starch suspension, which may contain 30-40% w/w dry solids (ds), to maltodextrans. α-Amylases are endohydrolases that catalyze the random cleavage of internal α-1,4-D-glucosidic bonds. Because liquefaction typically is conducted at high temperatures, e.g., 90-100° C., thermostable α-amylases, such as an α-amylase from *Bacillus* sp., are preferred for this step. α-Amylases currently used for this step, e.g., α-amylases from *B. licheniformis*, *B. amyloliquefaciens*, and *B. stearothermophilus* (AmyS), do not produce significant amounts of glucose. Instead, the resulting liquefact has a low dextrose equivalent (DE) and contains maltose and sugars with high degrees of polymerization (DPn).

(2) Saccharification: Glucoamylases and/or maltogenic α-amylases catalyze the hydrolysis of non-reducing ends of the maltodextrans formed after liquefaction, releasing D-glucose, maltose and isomaltose. Saccharification produces either glucose-rich or high-maltose syrups. In the former case, glucoamylases typically catalyze saccharification under acidic conditions at elevated temperatures, e.g., 60° C., pH 4.3. Glucoamylases used in this process typically are obtained from fungi, e.g., *Aspergillus niger* glucoamylase used in Optidex® L400 or *Humincola grisea* glucoamylase. De-branching enzymes, such as pullulanases, can aid saccharification.

Maltogenic α-amylases alternatively may catalyze saccharification to form high-maltose syrups. Maltogenic α-amylases typically have a higher optimal pH and a lower optimal temperature than glucoamylase, and maltogenic amylases typically require $Ca^{2+}$. Maltogenic α-amylases currently used for this application include *B. subtilis* α-amylases, plant amylases, and the α-amylase from *Aspergillus oryzae*, the active ingredient of Clarase® L. Exemplary saccharification reactions used to produce various products are depicted below:

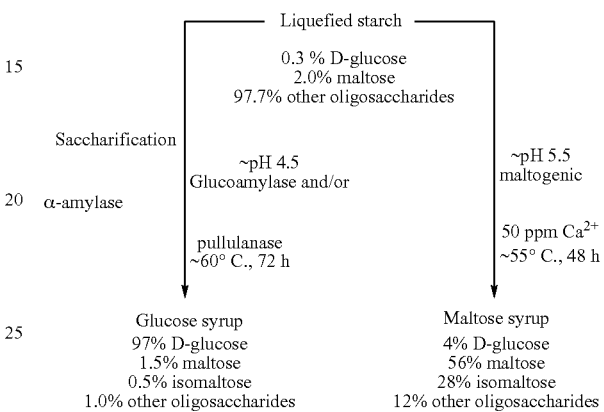

(3) Further processing: A branch point in the process occurs after the production of a glucose-rich syrup, shown on the left side of the reaction pathways above. If the final desired product is a biofuel, yeast can ferment the glucose-rich syrup to ethanol. On the other hand, if the final desired product is a fructose-rich syrup, glucose isomerase can catalyze the conversion of the glucose-rich syrup to fructose.

Saccharification is the rate-limiting step in the production of a glucose-rich syrup. Saccharification typically occurs over 48-72 hours, by which time many fungal glucoamylases lose significant activity. Further, although maltogenic α-amylases and glucoamylases both can catalyze saccharification, the enzymes typically operate at different optimal pH and temperatures, as shown above. If both enzymes are used sequentially, the difference in reaction conditions between the two enzymes necessitates adjusting the pH and temperature, which slows down the overall the process and may give rise to the formation of insoluble amylose aggregates.

Accordingly, there is a need in the art for an improved process of making industrial products from starch. In particular, there is a need for improved efficiencies in a saccharification step.

SUMMARY

An α-amylase from *Bacillus subtilis* (AmyE) produces significant amounts of glucose from various carbohydrate substrates, including vegetable starch, maltoheptaose, and maltotriose. Among other things, this advantageous property allows AmyE or variants thereof to be used in a saccharification reaction having a reduced or eliminated requirement for glucoamylase. The reduction or elimination of the glucoamylase requirement significantly improves the efficiency of the production of high fructose corn syrup (HFCS) or ethanol, for example.

To that end, a method of using a *Bacillus subtilis* α-amylase (AmyE) or a variant thereof to produce a solution comprising a significant amount of glucose can comprise: (i)

contacting AmyE or variant thereof with a substrate solution comprising maltose, maltoheptaose, or maltotriose; and (ii) converting the substrate solution to a significant amount of glucose, wherein the AmyE or variant thereof has the amino acid sequence of SEQ ID NO: 1 or an amino acid sequence with at least about 85% sequence identity to SEQ ID NO: 1 and with α-amylase activity. The final concentration of glucose in the solution may be 20% w/w or more. The substrate solution advantageously may be contacted with AmyE or a variant thereof in the absence of an added glucoamylase. In one embodiment, the substrate solution is contacted with AmyE or a variant thereof in the presence of a glucoamylase, where the pH of the solution is at about pH 4.0 to pH 4.5, optionally in the absence of added $Ca^{2+}$.

In one embodiment the oligosaccharide solution comprises predominantly maltoheptaose (DP7) or higher oligosaccharides. In another embodiment the starch solution is uncooked corn starch.

In yet another embodiment the pH of the substrate solution during the converting of the substrate solution is about pH 5.6 to about pH 5.8. In one embodiment the converting of the substrate solution does not comprise contacting the substrate solution with a glucoamylase.

In one embodiment step (i) further comprises contacting the starch substrate with a glucoamylase. In a particular embodiment the glucoamylase is added to a concentration of less than about 0.5 GAU/g ds. In an additional embodiment the glucoamylase is added to a concentration of less than about 0.02 GAU/g ds.

In one embodiment the solution comprising glucose contains at least about 0.2 g/L glucose. In an alternative embodiment the solution comprising glucose contains at least about 0.4 g/L glucose. In a further embodiment the solution comprising glucose contains at least about 1.4 g/L glucose.

Any naturally occurring AmyE is suitable for the present methods. For example, the AmyE may have the amino acid sequence of SEQ ID NO: 1 or an amino acid sequence with at least about 85%, 90%, or 95% sequence identity to SEQ ID NO: 1, measured with the BLAST sequence alignment algorithm with default matching parameters, such as the AmyE having the amino acid sequence of SEQ ID NO: 3 (Amy31A). Amy31A is disclosed in Ohdan et al., "Characteristics of two forms of alpha-amylases and structural implication," *Appl. Environ. Microbiol.* 65(10): 4652-58 (1999). Amy31A has about 86% sequence identity to the AmyE of SEQ ID NO: 1, using the BLAST algorithm. AmyE variants also are useful, which have amino acid sequences that differ from the sequence of a naturally occurring AmyE. Variants include an AmyE having a deletion of the C-terminal starch binding domain, such as the truncated AmyE having the amino acid sequence of SEQ ID NO: 2 (AmyE-tr), which is the AmyE truncated from residue D425 of SEQ ID NO: 1. Polynucleotides encoding the AmyE and AmyE variants also are provided. Vectors and host cells useful for expressing the polynucleotides are provided, as well.

In one embodiment the AmyE is selected from the group consisting of the AmyE comprising the amino acid sequence set forth in SEQ ID NO: 1, SEQ ID NO: 2, SEQ ID NO: 3, NCBI Accession No. ABW75769, NCBI Accession No. ABK54355, NCBI Accession No. AAF14358, NCBI Accession No. AAT01440, NCBI Accession No. AAZ30064, NCBI Accession No. NP_388186, NCBI Accession No. AAQ83841, and NCBI Accession No. BAA31528.

The method of saccharifying starch may further comprise fermenting the saccharified starch solution to produce a biofuel such as ethanol. In one embodiment, a batch fermentation process is used in a closed system, where the composition of the medium is set at the beginning of the fermentation and is not altered during the fermentation. In another embodiment, a "fed-batch fermentation" system is used, where the substrate is added in increments as the fermentation progresses. In yet another embodiment, a continuous fermentation system is used, where a defined fermentation medium is added continuously to a bioreactor, and an equal amount of conditioned medium is removed simultaneously for processing.

In one embodiment a further step includes (iii) fermenting the solution comprising glucose to produce ethanol. In a particular embodiment the ethanol concentration is at least about 6% v/v ethanol. In another embodiment the ethanol concentration is at least about 14% v/v ethanol.

A method is also provided that further comprises contacting the saccharified starch solution with a glucose isomerase. Accordingly, in a particular embodiment a further step comprises (iii) contacting the solution comprising glucose with a glucose isomerase to produce high fructose corn syrup. In one embodiment, the saccharified starch solution contains no exogenously added $Ca^{2+}$. The saccharified starch solution may be converted to fructose-starch based syrup (HFSS), such as HFCS. The conversion of saccharified starch to HFSS may be catalyzed at a pH of about 6.0 to about 8.0, e.g., pH 7.5. In one embodiment, the product contains about 40-45% fructose.

Also provided is a starch processing composition comprising an AmyE or variant thereof and optionally a glucoamylase, a pullulanase, a β-amylase, a fungal α-amylase, a protease, a cellulase, a hemicellulase, a lipase, a cutinase, an isoamylase, or a combination thereof.

Also provided is a baking composition comprising an AmyE or variant thereof in a solution or in a gel. A method of baking comprises adding the baking composition to a substance to be baked, and baking the substance.

Also provided is a textile desizing composition comprising an AmyE or variant thereof in an aqueous solution, and optionally with another enzyme. A method of desizing a textile comprises contacting the desizing composition with a textile for a time sufficient to desize the textile. In one embodiment a method of desizing textiles comprises (i) contacting a textile with AmyE and (ii) desizing the textile, wherein the AmyE comprises an amino acid sequence with at least about 85% sequence identity to the AmyE of SEQ ID NO: 1.

Also provided is a cleaning composition comprising an AmyE or variant thereof in an aqueous solution, and optionally another enzyme, detergent and/or bleach. The cleaning solution is used for laundering or washing dishes, for example. A method is provided that comprises contacting the cleaning composition with an article to be cleaned, e.g., dishes or laundry, for a sufficient time for the article to be cleaned.

In one embodiment a method of washing an item is provided, comprising (i) contacting an item to be washed with a detergent composition comprising AmyE and (ii) washing the item, wherein the AmyE comprises an amino acid sequence with at least about 85% sequence identity to the AmyE of SEQ ID NO: 1.

In a particular embodiment the item to be washed is dishware or clothing. In another embodiment the detergent composition is a non-dusting granulate or a stabilized liquid. In a further embodiment the detergent composition further comprises a cellulase, a protease, an amylase, or a combination thereof. In one embodiment the amylase is an α-amylase, a β-amylase, or a glucoamylase. In a further embodiment the detergent composition further comprises a lipase, a peroxidase, a mannanase, a pectate lyase, or a combination thereof. In one embodiment the detergent composition is a manual or automatic dishwashing detergent composition. In another embodiment the detergent composition further comprises a protease, a lipase, a peroxidase, an amylase, a cellulase, a mannanase, a pectate lyase, or a combination thereof.

BRIEF DESCRIPTION OF THE DRAWINGS

The accompanying drawings are incorporated into the specification and provide non-limiting illustrations of various embodiments. In the drawings:

FIG. 1 depicts a sequence alignment between the AmyE having the amino acid sequence of SEQ ID NO: 1 ("AmyE full length") and the AmyE having the amino acid sequence of SEQ ID NO: 25 (mature "Amy31A"). Differences in the amino acid sequences are shown in bold font. Residues are numbered from the first amino acid in the mature form of the enzymes.

DETAILED DESCRIPTION

Figure 2:
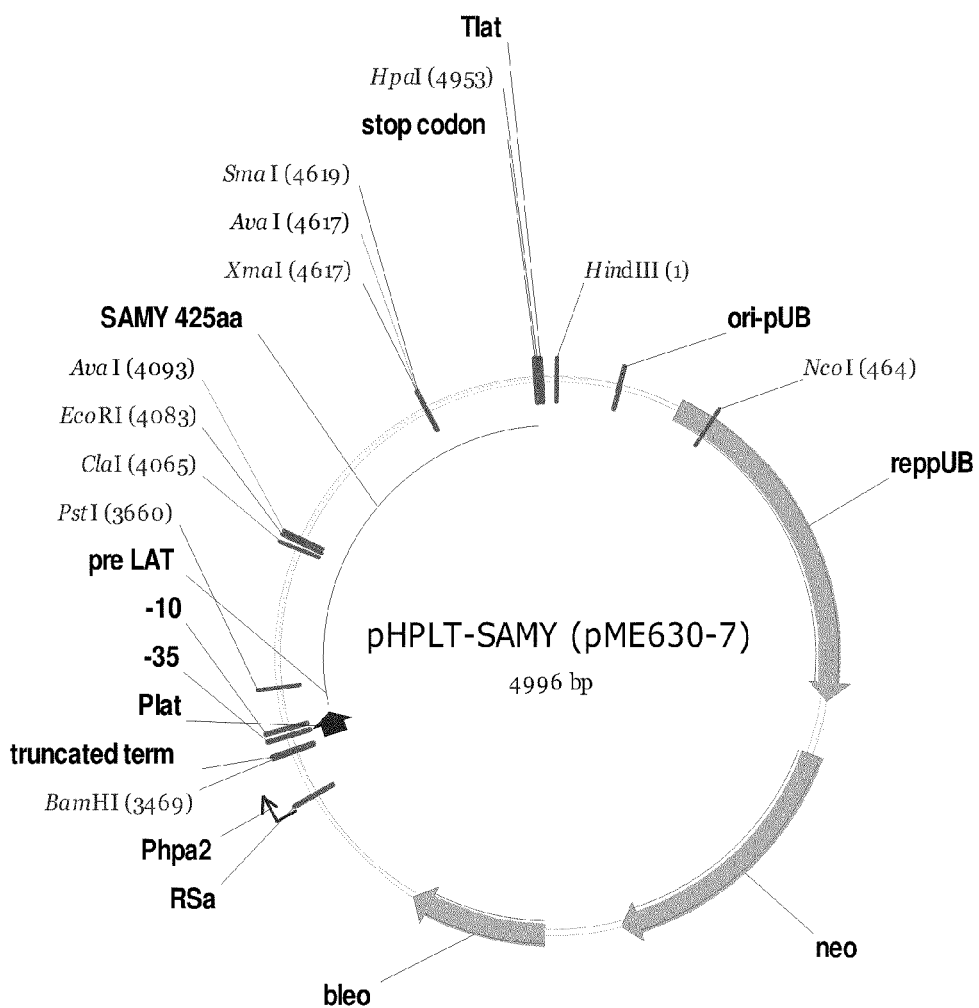
FIG. 2 depicts plasmid pME630-7, which comprises a polynucleotide (labeled "SAMY 425aa") that encodes AmyE-tr (SEQ ID NO: 2). The plasmid comprises a polynucleotide in-frame with the SAMY gene that encodes a signal sequence from *B. licheniformis* α-amylase (labeled "pre LAT").

An α-amylase from *Bacillus subtilis* (AmyE) produces significant amounts of glucose from various carbohydrate substrates, including vegetable starch, maltoheptaose, and maltotriose. Among other things, this advantageous property allows AmyE or variants thereof to be used in a saccharification reaction having a reduced or eliminated requirement for glucoamylase. The reduction or elimination of the glucoamylase requirement significantly improves the efficiency of the production of ethanol or high fructose corn syrup, for example.

1. Definitions and Abbreviations

In accordance with this detailed description, the following abbreviations and definitions apply. It should be noted that as used herein, the singular forms "a," "an," and "the" include plural referents unless the context clearly dictates otherwise. Thus, for example, reference to "an enzyme" includes a plurality of such enzymes and reference to "the formulation" includes reference to one or more formulations and equivalents thereof known to those skilled in the art, and so forth.

Unless defined otherwise, all technical and scientific terms used herein have the same meaning as commonly understood by one of ordinary skill in the art. The following terms are provided below.

1.1. Definitions

As used herein, "amino acid sequence" is synonymous with the term "polypeptide" and/or the term "protein." In some instances, the term "amino acid sequence" is synonymous with the term "peptide"; in some instances, the term "amino acid sequence" is synonymous with the term "enzyme."

As used herein, "hybridization" includes the process by which a strand of nucleic acid joins with a complementary strand through base pairing, as well as the process of amplification as carried out in polymerase chain reaction (PCR) technologies. Hybridized nucleic acid may exist as single- or double-stranded DNA or RNA, an RNA/DNA heteroduplex, or an RNA/DNA copolymer. As used herein, "copolymer" refers to a single nucleic acid strand that comprises both ribonucleotides and deoxyribonucleotides. Nucleic acids include those that hybridize under "highly stringent conditions" to a nucleic acid disclosed herein. Highly stringent conditions are defined as hybridization at 50° C. in 0.2×SSC or at 65° C. in 0.1×SSC (1×SSC=0.15 M NaCl, 0.015 M sodium citrate, pH 7.0).

As used herein, "nucleotide sequence" or "nucleic acid sequence" refer to a sequence of genomic, synthetic, or recombinant origin and may be double-stranded or single-stranded, whether representing the sense or anti-sense strand. As used herein, the term "nucleic acid" may refer to genomic DNA, cDNA, synthetic DNA, or RNA. The residues of a nucleic acid may contain any of the chemically modifications commonly known and used in the art.

"Isolated" means that the material is at least substantially free from at least one other component that the material is naturally associated and found in nature.

"Purified" means that the material is in a relatively pure state, e.g., at least about 90% pure, at least about 95% pure, or at least about 98% pure.

"Thermostable" means the enzyme retains activity after exposure to elevated temperatures. The thermostability of an AmyE is measured by its half-life ($t_{1/2}$), where half of the enzyme activity is lost by the half-life. The half-life is measured by determining the specific α-amylase activity of the enzyme remaining over time at a given temperature, particularly at a temperature used for a specific application.

As used herein, "food" includes both prepared food, as well as an ingredient for a food, such as flour, that is capable of providing any beneficial effect to the consumer. "Food ingredient" includes a formulation that is or can be added to a food or foodstuff and includes formulations used at low levels in a wide variety of products that require, for example, acidifying or emulsifying. The food ingredient may be in the form of a solution or as a solid, depending on the use and/or the mode of application and/or the mode of administration.

"Oligosaccharide" means a carbohydrate molecule composed of 3-20 monosaccharides.

"Homologue" means an entity having a certain degree of identity or "homology" with the subject amino acid sequences and the subject nucleotide sequences. A "homologous sequence" includes an amino acid sequence having at least 85% sequence identity to the subject sequence, e.g., at least 85%, 90%, 95%, 96%, 97%, 98% or 99% identity to the subject sequence. Typically, homologues will comprise the same active site residues as the subject amino acid sequence.

As used herein, "transformed cell" includes cells that have been transformed by use of recombinant DNA techniques. Transformation typically occurs by insertion of one or more nucleotide sequences into a cell. The inserted nucleotide sequence may be a heterologous nucleotide sequence, i.e., is a sequence that is not natural to the cell that is to be transformed, such as a fusion protein.

As used herein, "operably linked" means that the described components are in a relationship permitting them to function in their intended manner. For example, a regulatory sequence operably linked to a coding sequence is ligated in such a way that expression of the coding sequence is achieved under condition compatible with the control sequences.

As used herein, "biologically active" refers to a sequence having a similar structural, regulatory, or biochemical function as the naturally occurring sequence, although not necessarily to the same degree.

1.2. Abbreviations

The following abbreviations apply unless indicated otherwise:

AE alcohol ethoxylate
AEO alcohol ethoxylate
AEOS alcohol ethoxysulfate
AES alcohol ethoxysulfate
AGU glucoamylase activity unit
AkAA *Aspergillus kawachii* α-amylase
AmyE *Bacillus subtilis* α-amylase
AmyR Spezyme® Xtra amylase
AmyS *Geobacillus stearothermophilus* α-amylase
AS alcohol sulfate
BAA bacterial α-amylase
cDNA complementary DNA
CMC carboxymethylcellulose
DE Dextrose Equivalent
DI distilled, deionzed
DNA deoxyribonucleic acid
DP3 degree of polymerization with three subunits
DPn degree of polymerization with n subunits
DS or ds dry solid
DTMPA diethyltriaminepentaacetic acid
EC enzyme commission for enzyme classification
EDTA ethylenediaminetetraacetic acid
EDTMPA ethylenediaminetetramethylene phosphonic acid
EO ethylene oxide
F&HC fabric and household care
GAU glucoamylase units
HFCS high fructose corn syrup
HFSS high fructose starch based syrup
IPTG isopropyl β-D-thiogalactoside
LA Lauria agar
LB Lauria broth
LU Lipase Units
LIT leucine (L) residue at position 1 is replaced with a threonine (T) residue, where amino acids are designated by single letter abbreviations commonly known in the art
MW molecular weight
NCBI National Center for Biotechnology Information
nm nanometer
NOBS nonanoyloxybenzenesulfonate
NTA nitrilotriacetic acid
OD optical density
PCR polymerase chain reaction
PEG polyethylene glycol
pI isoelectric point
ppm parts per million
PVA poly(vinyl alcohol)
PVP poly(vinylpyrrolidone)
RAU Reference Amylase Units
RNA ribonucleic acid
SAS secondary alkane sulfonates
1×SSC 0.15 M NaCl, 0.015 M sodium citrate, pH 7.0
SSF simultaneous saccharification and fermentation
SSU soluble starch unit, equivalent to the reducing power of 1 mg of glucose released per minute
TAED tetraacetylethylenediamine
TNBS trinitrobenzenesulfonic acid
TrGA *Trichoderma reesei* glucoamylase
w/v weight/volume
w/w weight/weight
wt wild-type
μL microliter
μNm microNewton×meter

2. AmyE and Variants Thereof

Amy E enzymes and variants thereof are provided, which are useful for carrying out the methods disclosed herein. Nucleic acids encoding AmyE and variants thereof also are provided, as are vectors and host cells comprising the nucleic acids.

"AmyE" for the purpose of this disclosure means a naturally occurring α-amylase (EC 3.2.1.1; 1,4-α-D-glucan glucanohydrolase) from *B. subtilis*. A representative AmyE sequence is set forth in SEQ ID NO: 1. The amino acid sequence of AmyE shown in SEQ ID NO: 1 is that of the mature form, without the native signal sequence. The amino acid sequence of the native signal sequence of this AmyE is shown in SEQ ID NO: 17. The mature form of this AmyE is referred to elsewhere in the present disclosure as "AmyE full-length." Other AmyE sequences have at least about 85% sequence identity to the AmyE of SEQ ID NO: 1, using the BLAST sequence alignment algorithm with default alignment parameters. For example, an AmyE known as Amy31A, disclosed in UniProtKB/TrEMBL Accession No. 082953 (SEQ ID NO: 3), has an 86% sequence identity to the AmyE of SEQ ID NO: 1. The N-terminal 45 amino acid residues of SEQ ID NO: 3 are the signal sequence of Amy31A. A sequence alignment between AmyE (SEQ ID NO: 1) and Amy31A (without the signal sequence) is depicted in FIG. 1. AmyE enzymes include, but are not limited to, the AmyE having the amino acid sequence disclosed in NCBI Accession No. ABW75769. Further AmyE protein sequences include those disclosed in NCBI Accession Nos. ABK54355, AAF14358, AAT01440, AAZ30064, NP_388186, AAQ83841, and BAA31528, the contents of which are incorporated here by reference.

An AmyE "variant" comprises an amino acid sequence modification of a naturally occurring AmyE sequence. As used herein, a naturally occurring AmyE is also a "parent enzyme," "parent sequence," "parent polypeptide," or "wild-type AmyE." The amino acid modification may comprise an amino acid substitution, addition, or deletion. The amino acid modification in the AmyE variant may be the result of a naturally occurring mutation or the result of deliberate modification of the amino sequence using one of the well known methods in the art for this purpose, described further below. Representative AmyE variants are disclosed in co-pending application, which is incorporated herein in its entirety.

An AmyE variant, unless otherwise specified, has at least one amino acid modification, but the variant retains at least 85% sequence identity with the AmyE of SEQ ID NO: 1, measured by a BLAST alignment of the protein sequences with default alignment parameters. The AmyE variant may have at least 85%, 90%, 95%, 97%, 98%, or 99% amino acid sequence identity to the AmyE of SEQ ID NO: 1. For example, the variant may have one, two, three, up to five, up to ten, or up to 20 amino acid substitutions compared to the amino acid sequence of SEQ ID NO: 1. Typically, modifications are made to amino acid residues that are not required for biological function. The selection of amino acid residues to be modified may be guided by sequence homology among AmyE sequences. Generally, amino acids that are well conserved in AmyE sequences are more likely to be required for biological activity. Conversely, amino acid positions that vary among AmyE sequences are less likely to be required for biological activity. For example, amino acid residues that differ in the alignment between AmyE and Amy31A, shown in bold font in FIG. 1, likely can be modified in an AmyE variant without loss of biological activity.

AmyE or variants thereof may be expressed as a fusion protein that comprises sequences at the N- and/or C-terminus of the mature form of AmyE that facilitate expression, detection, and/or purification, e.g., a signal sequence or a His-tag. Such a sequence includes a signal sequence, which facilitates secretion and expression of the AmyE in a host organism. Additional amino acid residues may be cleaved from the N-terminus of an AmyE, following cleavage of the signal sequence, as discussed in Yang et al., "Nucleotide sequence of the amylase gene from *Bacillus subtilis*," *Nucleic Acids Res*. 11: 237-49 (1983). A "mature form" of an AmyE is defined as the product of all such post-translational modifications of the expressed AmyE sequence. Sequences found at the N-terminus of the primary translation product that are cleaved to form the mature AmyE may be designated alternatively as a "signal sequence," "leader sequence," or "pro-sequence."

The signal sequence may encoded by the same gene as the AmyE. For example, the AmyE set forth in SEQ ID NO: 1 is expressed naturally with a signal sequence and additional N-terminal amino acids having the sequence (SEQ ID NO: 17)
MFAKRFKTSLLPLFAGFLLLFHLVLAGPAAASAETANKSNE.

The signal sequence alternatively may be a *B. subtilis* sp. signal sequence from a different AmyE or even a different protein. Further, the signal sequence may be from a different species, e.g., *B. licheniformis*. The signal sequence may be chosen to provide optimal expression of the AmyE or variant thereof in a particular host cell, for example. The mature AmyE may be produced as a result of proteolytic cleavage of additional sequences from the N-terminus that are not signal sequences. For example, a 31-amino acid residue signal sequence from *B. licheniformis* ("LAT leader sequence") may be fused in frame with an AmyE sequence.

An AmyE variant for the purpose of this disclosure has at least partial 1,4-α-D-glucan glucanohydrolase activity, compared to a naturally occurring AmyE. Variants may have the same activity and properties as a wild-type AmyE, or variants may have an altered property, compared to a wild-type AmyE. The altered property may be an altered, e.g., two- or three-fold higher, specific activity toward maltoheptaose and/or maltotriose substrates. The thermostability of the protein alternatively or additionally may be altered. For example, the variant may be more thermostable than AmyE. The altered property alternatively or additionally may be the optimal pH for enzymatic activity. For example, the variant may have a more acidic or alkaline optimum pH.

A "truncated" AmyE ("AmyE-tr") means an AmyE with a sequence deletion of all or part of the C-terminal starch binding domain. In the AmyE-tr of SEQ ID NO: 2, for example, the AmyE of SEQ ID NO: 1 is truncated at residue D425. A 2.5 Å resolution crystal structure of this AmyE-tr is available at Protein Databank Accession No. 1BAG, which is disclosed in Fujimoto et al., "Crystal structure of a catalytic-site mutant alpha-amylase from *B. subtilis* complexed with maltopentaose," *J. Mol. Biol.* 277: 393-407 (1998). AmyE-tr may be truncated at other positions, e.g., Y423, P424, D426 or I427 of the AmyE of SEQ ID NO: 1, provided all or part of the C-terminal starch binding domain is removed.

Nucleic acids encoding AmyE or a variant thereof include, but are not limited to, the polynucleotide disclosed in SEQ ID NO: 9 and NO: 10, which encode the AmyE of SEQ ID NO: 1 and AmyE-tr (SEQ ID NO: 2), respectively. Further representative polynucleotides include that disclosed in SEQ ID NO: 11, which encodes Amy31A (SEQ ID NO: 3). The AmyE disclosed in NCBI Accession Nos. ABK54355, AAF14358, AAT01440, AAZ30064, NP_388186, AAQ83841, and BAA31528 likewise are encoded by polynucleotides disclosed in publicly accessible databases, which sequences are incorporated herein by reference. Nucleic acids may be DNA, mRNA, or cDNA sequences. Nucleic acids further include "degenerate sequences" of any of the aforementioned nucleic acids. A degenerate sequence contains at least one codon that encodes the same amino acid residue but has a different nucleotide sequence from the aforementioned nucleic acid sequences. For example, nucleic acids include any nucleic acid sequence that encodes an AmyE or variant thereof. Degenerate sequences may be designed for optimal expression by using codons preferred by a particular host organism.

Vectors comprising the nucleic acids encoding AmyE or variants thereof also are provided. Host cells comprising the vectors are provided. The host cell may express the polynucleotide encoding the AmyE variant. The host may be a *Bacillus* sp., e.g., *B. subtilis*.

2.1. Characterization of AmyE Variants

AmyE variants can be characterized by their nucleic acid and primary polypeptide sequences, by 3D structural modeling, and/or by their specific activity. Additional characteristics of the AmyE variant include stability, $Ca^{2+}$ dependence, pH range, oxidation stability, and thermostability. In one aspect, the AmyE variants are expressed at higher levels than the wild-type AmyE, while retaining the performance characteristics of the wild-type AmyE. Levels of expression and enzyme activity can be assessed using standard assays known to the artisan skilled in this field. In another aspect, variants demonstrate improved performance characteristics relative to the wild-type enzyme, such as improved stability at high temperatures or improved activity at various pH values, e.g., pH 4.0 to 6.0 or pH 8.0 to 11.0.

The AmyE variant may be expressed at an altered level in a host cell compared to AmyE. Expression generally relates to the amount of active variant that is recoverable from a fermentation broth using standard techniques known in this art over a given amount of time. Expression also can relate to the amount or rate of variant produced within the host cell or secreted by the host cell. Expression also can relate to the rate of translation of the mRNA encoding the variant enzyme.

In a further aspect, important mutations exhibit altered stability or specific activity, especially at temperatures around 60° C., e.g., 50-70° C., for use in saccharification, for example. Variants may have altered stability or specific activity at other temperatures, depending on whether the variant is to used in other applications or compositions. For example, in baking products, variant may exhibit altered specific activity at higher temperature ranges.

AmyE variants also may have altered oxidation stability, in particular higher oxidation stability, in comparison to the parent AmyE. For example, increased oxidation stability is advantageous in detergent compositions, and decreased oxidation stability may be advantageous in composition for starch liquefaction.

The AmyE variants described herein can also have mutations that extend half-life relative to the parent enzyme by 10%, 20%, 30%, 40%, 50%, 60%, 70%, 80%, 90%, 100%, 200% or more, particularly at elevated temperatures of about 55° C. to about 95° C. or more, particularly at about 80° C. In one embodiment, the AmyE variant can be heated for about 1-10 minutes at 80° C. or higher.

The AmyE variants may have exo-specificity, measured by exo-specificity indices described herein, for example. AmyE variants include those having higher or increased exo-specificity compared to the parent enzymes or polypeptides from which they were derived, optionally when measured under identical conditions. Thus, for example, the AmyE variant polypeptides may have an exo-specificity index 10%, 20%, 30%, 40%, 50%, 60%, 70%, 80%, 90%, 100%, 150%, 200%, 500%, 1000%, 5000%, 10,000% or higher compared to their parent polypeptides.

In one aspect, the AmyE variant has the same pH stability as the parental sequence. In another aspect, the variant comprises a mutation that confers a greater pH stability range or shifts the pH range to a desired area for the end commercial purpose of the enzyme. For example, in one embodiment, the variant can degrade starch at about pH 5.0 to about pH 10.5. The AmyE variant polypeptide may have a longer half-life or higher activity (depending on the assay) compared to the parent polypeptide under identical conditions, or the AmyE variant may have the same activity as the parent polypeptide. The AmyE variant polypeptide also may have about 10%, 20%, 30%, 40%, 50%, 60%, 70%, 80%, 90%, 100%, 200% or longer half-life compared to their parent polypeptide under identical pH conditions. Alternatively, or in addition, the AmyE variant may have higher specific activity compared to the parent polypeptide under identical pH conditions.

In another aspect, a nucleic acid complementary to a nucleic acid encoding any of the AmyE variants set forth herein is provided. Additionally, a nucleic acid capable of hybridizing to the complement is provided. In another embodiment, the sequence for use in the methods and compositions described here is a synthetic sequence. It includes, but is not limited to, sequences made with optimal codon usage for expression in a particular host organism.

3. Production of AmyE and Variants Thereof

A DNA sequence encoding the enzyme variant produced by methods described herein, or by any alternative methods known in the art, can be expressed, in enzyme form, using an expression vector which typically includes control sequences encoding a suitable promoter, operator, ribosome binding site, translation initiation signal, and, optionally, a repressor gene or various activator genes.

3.1 Vectors

The recombinant expression vector carrying the DNA sequence encoding an AmyE or variant thereof may be any vector that may conveniently be subjected to recombinant DNA procedures, and the choice of vector will often depend on the host cell into which it is to be introduced. Thus, the vector may be an autonomously replicating vector, i.e., a vector that exists as an extrachromosomal entity, the replication of which is independent of chromosomal replication, e.g., a plasmid, a bacteriophage or an extrachromosomal element, mini-chromosome or an artificial chromosome. Alternatively, the vector may be one which, when introduced into a host cell, is integrated into the host cell genome and replicated together with the chromosome(s) into which it has been integrated. The integrated gene may also be amplified to create multiple copies of the gene in the chromosome by use of an amplifiable construct driven by antibiotic selection or other selective pressure, such as an essential regulatory gene or by complementation of an essential metabolic pathway gene.

An expression vector typically includes the components of a cloning vector, e.g., an element that permits autonomous replication of the vector in the selected host organism and one or more phenotypically detectable markers for selection purposes. The expression vector normally comprises control nucleotide sequences encoding a promoter, operator, ribosome binding site, translation initiation signal and optionally, a repressor gene or one or more activator genes. In one aspect, all the signal sequences used target the material to the cell culture media for easier enzyme collection and optionally purification. The procedures used to ligate the DNA construct encoding an AmyE or variant thereof, the promoter, terminator and other elements, respectively, and to insert them into suitable vectors containing the information necessary for replication, are well known to persons skilled in the art (see e.g., Sambrook et al., MOLECULAR CLONING: A LABORATORY MANUAL, $2^{nd}$ ed., Cold Spring Harbor, 1989 and $3^{rd}$ ed., 2001).

In the vector, the DNA sequence should be operably connected to a suitable promoter sequence. The promoter may be any DNA sequence that shows transcriptional activity in the host cell of choice and may be derived from genes encoding proteins either homologous or heterologous to the host cell. Suitable promoters for directing the transcription of the DNA sequence encoding an AmyE or variant thereof, especially in a bacterial host, include various *Bacillus*-derived promoters, such as an α-amylase promoter derived from *B. subtilis*, *B. licheniformis*, *B. stearothermophilus*, or *B. amyloliquefaciens*, the promoter of the lac operon of *E. coli*, the *Streptomyces coelicolor* agarase gene dagA or celA promoters, and the promoters of the *Bacillus subtilis* xylA and xylB genes, etc. For transcription in a fungal host, examples of useful promoters are those derived from the gene encoding *Aspergillus oryzae* TAKA amylase, *Rhizomucor miehei* aspartic proteinase, *Aspergillus niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase, or *A. nidulans* acetamidase. When the gene encoding the AmyE or variant thereof is expressed in a bacterial species such as *E. coli*, a suitable promoter can be selected, for example, from a bacteriophage promoter including a T7 promoter and a phage lambda promoter. Examples of suitable promoters for the expression in a yeast species include but are not limited to the Gal 1 and Gal 10 promoters of *Saccharomyces cerevisiae* and the *Pichia pastoris* AOX1 or AOX2 promoters.

The expression vector may also comprise a suitable transcription terminator and, in eukaryotes, polyadenylation sequences operably connected to the DNA sequence encoding the α-amylase variant. Termination and polyadenylation sequences may suitably be derived from the same sources as the promoter. The vector may further comprise a DNA sequence enabling the vector to replicate in the host cell in question. Examples of such sequences are the origins of replication of plasmids pUC19, pACYC177, pUB110, pE194, pAMB1, pICatH, and pIJ702.

The vector may also comprise a selectable marker, e.g., a gene the product of which complements a defect in the host cell, such as the dal genes from *B. subtilis* or *B. licheniformis*, or a gene which confers antibiotic resistance, e.g., ampicillin, kanamycin, chloramphenicol or tetracyclin resistance. Furthermore, the vector may comprise *Aspergillus* selection markers such as amdS, argB, niaD, and xxsC, a marker giving rise to hygromycin resistance, or the selection may be accomplished by co-transformation as known in the art. See, e.g., WO 91/17243.

3.2 Variant Expression and Host Organisms

It is generally advantageous if the AmyE or variant thereof is secreted into the culture medium, when expressed in a host cell. To this end, the AmyE or variants thereof may comprise a signal sequence that permits secretion of the expressed enzyme into the culture medium. If desirable, this original signal sequence may be replaced by a different signal sequence, which is conveniently accomplished by substitution of the DNA sequences encoding the respective signal sequence. For example, a nucleic acid encoding AmyE is operably linked to a *B. licheniformis* signal sequence in the expression vector shown in FIG. 2. Signal sequences are discussed in more detail above.

An isolated cell, either comprising a DNA construct or an expression vector, is advantageously used as a host cell in the recombinant production of an AmyE or variant thereof. The cell may be transformed with the DNA construct encoding the AmyE or variant thereof, optionally by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

Examples of suitable bacterial host organisms are Gram positive bacterial species such as Bacillaceae, including *B. subtilis, B. licheniformis, B. lentus, B. brevis, B. stearothermophilus, B. alkalophilus, B. amyloliquefaciens, B. coagulans, B. lautus, B. megaterium*, and *B. thuringiensis; Streptomyces* sp., such as *S. murinus*; lactic acid bacterial species including *Lactococcus* sp., such as *L. lactis; Lactobacillus* sp., including *L. reuteri; Leuconostoc* sp.; *Pediococcus sp.*; and *Streptococcus* sp. Still other useful hosts include *Bacillus* sp. A 7-7, for example. Alternatively, strains of a Gram negative bacterial species belonging to Enterobacteriaceae, including *E. coli*, or to Pseudomonadaceae can be selected as the host organism.

A suitable yeast host organism can be selected from biotechnologically relevant yeasts species, such as, but not limited to, *Pichia* sp., *Hansenula* sp., *Kluyveromyces* sp., *Yarrowinia* sp., *Saccharomyces* sp., including *S. cerevisiae*, or a species belonging to *Schizosaccharomyces*, such as *S. pombe*. A strain of the methylotrophic yeast species *Pichia pastoris* can be used as the host organism. Alternatively, the host organism can be a *Hansenula* species. Suitable host organisms among filamentous fungi include species of *Aspergillus*, e.g., *A. niger, A. oryzae, A. tubigensis, A. awamori*, or *A. nidulans*. Alternatively, a strain of *Fusarium* sp., e.g., *Fusarium oxysporum* or *Rhizomucor* sp., such as *R. miehei*, can be used as the host organism. Other suitable yeasts include *Thermomyces* sp. and *Mucor* sp. Fungal cells may be transformed by a process involving protoplast formation and transformation of the protoplasts followed by regeneration of the cell wall in a manner known in the art. A suitable procedure for transforming *Aspergillus* host cells, for example, is described in EP 238023.

In a yet further aspect, a method of producing an AmyE or variant thereof is provided, which method comprises cultivating a host cell as described above under conditions conducive to the production of the variant and recovering the variant from the cells and/or culture medium. The medium used to cultivate the cells may be any conventional medium suitable for growing the host cell in question and obtaining expression of the AmyE or variant thereof. Suitable media and media components are available from commercial suppliers or may be prepared according to published recipes, e.g., as described in catalogues of the American Type Culture Collection (ATCC). Exemplary culture media include, but are not limited to, those for fed-batch fermentations performed in a three thousand liter (3,000 L) stirred tank fermentor. The growth medium in that case can consist of corn steep solids and soy flour as sources of organic compounds, along with inorganic salts as a source of sodium, potassium, phosphate, magnesium and sulfate, as well as trace elements. Typically, a carbohydrate source such as glucose is also part of the initial medium. Once the culture has established itself and begins growing, the carbohydrate is metered into the tank to maintain the culture as is known in the art. Samples are removed from the fermentor at regular intervals to measure enzyme titer using, for example, a calorimetric assay method. The fermentation process is halted when the enzyme production rate stops increasing according to the measurements.

An AmyE or variant thereof secreted from the host cells may conveniently be recovered from the culture medium by well-known procedures, including separating the cells from the medium by centrifugation or filtration, and precipitating proteinaceous components of the medium by means of a salt such as ammonium sulfate, followed by the use of chromatographic procedures such as ion exchange chromatography, affinity chromatography, or the like.

Host cells may be cultured under suitable conditions that allow expression of the AmyE or variant thereof. Expression of the proteins may be constitutive such that they are continually produced, or inducible, requiring a stimulus to initiate expression. In the case of inducible expression, protein production can be initiated when required by addition of an inducer substance, e.g., dexamethasone, IPTG, or Sepharose, to the culture medium, for example. Polypeptides can also be produced recombinantly in an in vitro cell-free system, such as the TnT™ (Promega) rabbit reticulocyte system.

A host for expressing AmyE or variant thereof can be cultured under aerobic conditions in the appropriate medium for the host. Shaking or a combination of agitation and aeration can be provided, with production occurring at the appropriate temperature for that host, e.g., from about 30° C. to about 75° C., depending on the needs of the host and production of the desired α-amylase variant. Culturing can occur from about 12 to about 100 hours or greater (and any hour value there between) or more particularly from 24 to 72 hours. Typically, the culture broth is at a pH of about 5.5 to about 8.0, again depending on the culture conditions needed for the host cell relative to production of the AmyE or variant thereof.

The amylolytic activity of the expressed enzyme may be determined using potato starch as substrate, for example. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

4. Purification of AmyE and Variants Thereof

Conventional methods can be used in order to prepare a purified AmyE or variant thereof. After fermentation, a fermentation broth is obtained, and the microbial cells and various suspended solids, including residual raw fermentation materials, are removed by conventional separation techniques to obtain an amylase solution. Filtration, centrifugation, microfiltration, rotary vacuum drum filtration, followed by ultra-filtration, extraction or chromatography, or the like are generally used.

It is desirable to concentrate the solution containing the expressed AmyE or variant thereof to optimize recovery, since the use of un-concentrated solutions requires increased incubation time to collect precipitates containing the purified enzyme. The solution is concentrated using conventional techniques until the desired enzyme level is obtained. Concentration of the enzyme containing solution may be achieved by any of the techniques discussed above. In one embodiment, rotary vacuum evaporation and/or ultrafiltration is used. Alternatively, ultrafiltration can be used.

By "precipitation agent" for purposes of purification is meant a compound effective to precipitate the AmyE or variant thereof from solution, whatever the nature of the precipitate may be, i.e., crystalline, amorphous, or a blend of both. Precipitation can be performed using, for example, a metal halide precipitation agent. Metal halide precipitation agents include: alkali metal chlorides, alkali metal bromides and blends of two or more of these metal halides. The metal halide may be selected from the group consisting of sodium chloride, potassium chloride, sodium bromide, potassium bromide and blends of two or more of these metal halides. Suitable metal halides include sodium chloride and potassium chloride, particularly sodium chloride, which can further be used as a preservative. The selection of conditions of the precipitation for maximum recovery, including incubation time, pH, temperature and concentration of AmyE or variant thereof, will be readily apparent to one of ordinary skill in the art after routine testing.

Generally, at least about 5% w/v (weight/volume) to about 25% w/v of metal halide is added to the concentrated enzyme variant solution, and usually at least 8% w/v. Generally, no more than about 25% w/v of metal halide is added to the concentrated enzyme variant solution and usually no more than about 20% w/v. The optimal concentration of the metal halide precipitation agent will depend, among others, on the nature of the specific AmyE or variant thereof and on its concentration in solution.

Another alternative to effect precipitation of the enzyme is to use of organic compounds, which can be added to the concentrated enzyme variant solution. The organic compound precipitating agent can include: 4-hydroxybenzoic acid, alkali metal salts of 4-hydroxybenzoic acid, alkyl esters of 4-hydroxybenzoic acid, and blends of two or more of these organic compounds. The addition of said organic compound precipitation agents can take place prior to, simultaneously with or subsequent to the addition of the metal halide precipitation agent, and the addition of both precipitation agents, organic compound and metal halide, may be carried out sequentially or simultaneously. For further descriptions, see, e.g., U.S. Pat. No. 5,281,526 to Danisco A/S, for example.

Generally, the organic compound precipitation agents are selected from the group consisting of alkali metal salts of 4-hydroxybenzoic acid, such as sodium or potassium salts, and linear or branched alkyl esters of 4-hydroxybenzoic acid, wherein the alkyl group contains from 1 to 12 carbon atoms, and blends of two or more of these organic compounds. The organic compound precipitations agents can be for example linear or branched alkyl esters of 4-hydroxybenzoic acid, wherein the alkyl group contains from 1 to 10 carbon atoms, and blends of two or more of these organic compounds. Suitable organic compounds include linear alkyl esters of 4-hydroxybenzoic acid, wherein the alkyl group contains from 1 to 6 carbon atoms, and blends of two or more of these organic compounds. Methyl esters of 4-hydroxybenzoic acid, propyl ester of 4-hydroxybenzoic acid, butyl ester of 4-hydroxybenzoic acid, ethyl ester of 4-hydroxybenzoic acid and blends of two or more of these organic compounds can also be used. Additional organic compounds also include, but are not limited to, 4-hydroxybenzoic acid methyl ester (methyl PARABEN) and 4-hydroxybenzoic acid propyl ester (propyl PARABEN), which are also amylase preservative agents. Addition of the such an organic compound precipitation agent provides the advantage of high flexibility of the precipitation conditions with respect to pH, temperature, enzyme concentration, precipitation agent concentration, and time of incubation. Generally, at least 0.01% w/v of organic compound precipitation agent is added to the concentrated enzyme variant solution and usually at least 0.02% w/v. Generally, no more than 0.3% w/v of organic compound precipitation agent is added to the concentrated enzyme variant solution and usually no more than 0.2% w/v.

The concentrated enzyme solution, containing the metal halide precipitation agent and, in one aspect, the organic compound precipitation agent, is adjusted to a pH that necessarily will depend on the enzyme variant to be purified. Generally, the pH is adjusted to a level near the isoelectric point (pI) of the amylase. For example, the pH can be adjusted within a range of about 2.5 pH units below the pI to about 2.5 pH units above the pI. The pH may be adjusted accordingly if the pI of the variant differs from the wild-type pI.

The incubation time necessary to obtain a purified enzyme precipitate depends on the nature of the specific enzyme, the concentration of enzyme, and the specific precipitation agent(s) and its (their) concentration. Generally, the time effective to precipitate the enzyme variant is between about 1 to about 30 hours; usually it does not exceed about 25 hours. In the presence of the organic compound precipitation agent, the time of incubation can still be reduced to less than about 10 hours, and in most cases even about 6 hours.

Generally, the temperature during incubation is between about 4° C. and about 50° C. Usually, the method is carried out at a temperature between about 10° C. and about 45° C., and particularly between about 20° C. and about 40° C. The optimal temperature for inducing precipitation varies according to the solution conditions and the enzyme or precipitation agent(s) used.

The overall recovery of purified enzyme precipitate, and the efficiency with which the process is conducted, is improved by agitating the solution comprising the enzyme, the added metal halide and the added organic compound. The agitation step is done both during addition of the metal halide and the organic compound, and during the subsequent incubation period. Suitable agitation methods include mechanical stirring or shaking, vigorous aeration, or any similar technique.

The purified enzyme may be further purified by conventional separation techniques, such as filtration, centrifugation, microfiltration, rotary vacuum filtration, ultrafiltration, press filtration, cross membrane microfiltration, cross flow membrane microfiltration, or the like. Cross membrane microfiltration can be one method used. Further purification of the purified enzyme precipitate can be obtained by washing the precipitate with water. For example, the purified enzyme precipitate may be washed with water containing the metal halide precipitation agent, for example, with water containing the metal halide and the organic compound precipitation agents.

During culturing, expressed enzyme may accumulate in the culture broth. For the isolation and purification of the expressed enzyme, the culture broth may be centrifuged or filtered to eliminate cells, and the resulting cell-free liquid may be used for the purification of the enzyme. In one embodiment, the cell-free broth is subjected to salting out using ammonium sulfate at about 70% saturation; the 70% saturation-precipitation fraction is then dissolved in a buffer and applied to a column such as a Sephadex G-100 column, and eluted to recover the enzyme active fraction. For further purification, a conventional procedure such as ion exchange chromatography may be used.

Purified enzymes are useful for all applications in which the enzyme are generally utilized. For example, they can be used in laundry detergents and spot removers, in the food industry, in starch processing and baking, and in pharmaceutical compositions as digestive aids. They can be made into a final product that is either liquid (solution, slurry) or solid (granular, powder).

Alternatively, the enzyme product can be recovered and a flocculating agent is added to the media in order to remove cells and cell debris by filtration or centrifugation without further purification of the enzyme.

The AmyE and variants thereof produced and purified by the methods described above can be used in a variety of useful industrial applications. The enzymes possess valuable properties facilitating applications related to fabric and household care (F&HC). For example, an AmyE or variant thereof can be used as a component in washing, dishwashing and hard-surface cleaning detergent compositions. AmyE or variants thereof also are useful in the production of sweeteners and ethanol from starch, and/or for textile desizing. AmyE or variants thereof are particularly useful in starch-conversion processes, including starch liquefaction and/or saccharification processes, as described, for example, in WO 2005/111203 and U.S. Published Application No. 2006/0014265 (Danisco A/S). These uses of AmyE or variants thereof are described in more detail below.

5. Compositions and Uses of AmyE and Variants Thereof 5.1. Starch Processing Compositions and Use In one aspect, compositions with AmyE or variants thereof can be utilized for starch liquefaction and/or saccharification. The process may comprise hydrolysis of a slurry of gelatinized or granular starch, in particular hydrolysis of granular starch into a soluble starch hydrolysate at a temperature below the initial gelatinization temperature of the granular starch. Starch processing is useful for producing sweetener, producing alcohol for fuel or drinking (i.e., potable alcohol), producing a beverage, processing cane sugar, or producing desired organic compounds, e.g., citric acid, itaconic acid, lactic acid, gluconic acid, ketones, amino acids, antibiotics, enzymes, vitamins, and hormones. Conversion of starch to fructose syrups normally consists of three consecutive enzymatic processes: a liquefaction process, a saccharification process, and an isomerization process.

As used herein, the term "liquefaction" or "liquefy" means a process by which starch is converted to less viscous and shorter chain dextrins. Generally, this process involves gelatinization of starch simultaneously with or followed by the addition of an AmyE or variant thereof. As used herein, the term "primary liquefaction" refers to a step of liquefaction when the slurry's temperature is raised to or near its gelatinization temperature. Subsequent to the raising of the temperature, the slurry is sent through a heat exchanger or jet to temperatures from about 90-150° C., e.g., 100-110° C. Subsequent to application to a heat exchange or jet temperature, the slurry is held for a period of 3-10 minutes at that temperature. This step of holding the slurry at 90-150° C. is termed primary liquefaction.

As used herein, the term "secondary liquefaction" refers the liquefaction step subsequent to primary liquefaction (heating to 90-150° C.), when the slurry is allowed to cool to room temperature. This cooling step can be 30 minutes to 180 minutes, e.g. 90 minutes to 120 minutes. As used herein, the term "minutes of secondary liquefaction" refers to the time that has elapsed from the start of secondary liquefaction to the time that the Dextrose Equivalent (DE) is measured.

After the liquefaction process, the dextrins typically may be converted into dextrose by addition of a glucoamylase (e.g., AMG™) and optionally a debranching enzyme, such as an isoamylase or a pullulanase (e.g., Promozyme®). Before this step, the pH typically is reduced to a value below about 4.5, while maintaining the temperature at 95° C. or more, so that the liquefying α-amylase variant activity is denatured. The temperature then is lowered to 60° C., and a glucoamylase and a debranching enzyme are added. The saccharification process proceeds typically for about 24 to about 72 hours.

An advantage of AmyE and variants thereof is the ability of AmyE to catalyze the breakdown of complex sugars, such as maltose, maltotriose, and maltoheptaose. For this reason, the reaction can be catalyzed by AmyE or a variant thereof alone, optionally without a glucoamylase. A further advantage of the present AmyE or variants thereof is that dextrins may be converted into dextrose by the action or one or more AmyE or variants thereof under the same reaction conditions that are optimal for glucoamylase. This advantageous property of AmyE and variants thereof is disclosed in co-pending application, incorporated by reference in its entirety herein. Because AmyE and variants thereof operate at the same pH and temperature as glucoamylase, AmyE and variants thereof may be added before or after additional catalysis with a glucoamylase, or by a cocktail of AmyE or a variant thereof and a glucoamylase. The delays necessitated by adjusting the pH and temperature of the reaction to accommodate the use of a glucoamylase thus are avoided.

Glucoamylases, when added, preferably are present in an amount of no more than, or even less than, 0.5 glucoamylase activity unit (AGU)/g DS (i.e., glucoamylase activity units per gram of dry solids). Glucoamylases may be added in an amount of 0.02-2.0 AGU/g DS or 0.1-1.0 AGU/g DS, e.g., 0.2 AGU/g DS. Glucoamylases are derived from a microorganism or a plant. For example, glucoamylases can be of fungal or bacterial origin. Exemplary bacterial glucoamylases are *Aspergillus* glucoamylases, in particular *A. niger* G1 or G2 glucoamylase (Boel et al. (1984), *EMBO J.* 3(5): 1097-1102), or variants thereof, such as disclosed in WO 92/00381 and WO 00/04136; *A. awamori* glucoamylase (WO 84/02921); *A. oryzae* glucoamylase (*Agric. Biol. Chem.* (1991), 55(4): 941-949), or variants or fragments thereof. In one embodiment, the process also comprises the use of a carbohydrate-binding domain of the type disclosed in WO 98/22613. Other contemplated *Aspergillus* glucoamylase variants include variants to enhance the thermal stability: G137A and G139A (Chen et al. (1996), *Prot. Eng.* 9: 499-505); D257E and D293E/Q (Chen et al. (1995), *Prot. Eng.* 8: 575-582); N182 (Chen et al. (1994), *Biochem. J.* 301: 275-281); disulphide bonds, A246C (Fierobe et al. (1996), *Biochemistry,* 35: 8698-8704); and introduction of Pro residues in positions A435 and S436 (Li et al. (1997) Protein Eng. 10: 1199-1204). Other contemplated glucoamylases include *Talaromyces* glucoamylases, in particular derived from *T. emersonii* (WO 99/28448), *T. leycettanus* (U.S. Pat. No. RE 32,153), *T. duponti*, or *T. thermophilus* (U.S. Pat. No. 4,587,215). Contemplated bacterial glucoamylases include glucoamylases from the genus *Clostridium*, in particular *C. thermoamylolyticum* (EP 135138) and *C. thermohydrosulfuricum* (WO 86/01831). Suitable glucoamylases include the glucoamylases derived from *Aspergillus oryzae*, such as a glucoamylase having 50%, 55%, 60%, 65%, 70%, 75%, 80%, 85%, or even 90% homology to the amino acid sequence shown in SEQ ID NO: 2 in WO 00/04136. Also suitable are commercial glucoamylases, such as AMG 200L; AMG 300 L; SAN™ SUPER and AMG™ E (Novozymes); OPTIDEX® 300 (Genencor Division, Danisco US Inc.); AMIGASE™ and AMIGASE™ PLUS (from DSM); G-ZYME® G900 (Enzyme Bio-Systems); and G-ZYME® G990 ZR (*A. niger* glucoamylase and low protease content).

The AmyE or variants thereof can be used alone or can be combined with other AmyE variants, other α- or β-amylases, or other enzymes to provide a "cocktail" with a broad spectrum of activity. For example, the starch may be contacted with one or more enzyme selected from the group consisting of a fungal α-amylase (EC 3.2.1.1), a bacterial α-amylase, e.g., a *Bacillus* α-amylase or a non-*Bacillus* α-amylase, a β-amylase (EC 3.2.1.2), and/or a glucoamylase (EC 3.2.1.3). In an embodiment further another amylolytic enzyme or a debranching enzyme, such as an isoamylase (EC 3.2.1.68), or a pullulanases (EC 3.2.1.41) may be added to the AmyE or variant thereof. Isoamylase hydrolyses α-1,6-D-glucosidic branch linkages in amylopectin and β-limit dextrins and can be distinguished from pullulanases by the inability of isoamylase to attack pullulan and by the limited action of isoamylase on a-limit dextrins. Debranching enzymes may be added in effective amounts well known to the person skilled in the art.

β-Amylases are exo-acting maltogenic amylases, which catalyze the hydrolysis of 1,4-α-glucosidic linkages into amylose, amylopectin, and related glucose polymers, thereby releasing maltose. β-amylases have been isolated from various plants and microorganisms (Fogarty et al., PROGRESS IN INDUSTRIAL MICROBIOLOGY, Vol. 15, pp. 112-115, 1979). These β-amylases are characterized by having optimum temperatures in the range from 40° C. to 65° C., and optimum pH in the range from about 4.5 to about 7.0. Contemplated β-amylases include, but are not limited to, β-amylases from barley Spezyme® BBA 1500, Spezyme® DBA, Optimalt™ ME, Optimalt™ BBA (Danisco A/S); and Novozym™ WBA (Novozymes A/S).

After the saccharification process, the dextrose syrup may be converted into high fructose syrup using an immobilized glucose isomerase (such as Sweetzyme®), for example. In one regard, the soluble starch hydrolysate of the process is subjected to conversion into high fructose starch-based syrup (HFSS), such as high fructose corn syrup (HFCS). This conversion can be achieved using a glucose isomerase, particularly a glucose isomerase immobilized on a solid support. Contemplated isomerases included the commercial products Sweetzyme®, IT (Novozymes A/S); G-zyme® IMGI, and G-zyme® G993, Ketomax®, G-zyme® G993, G-zyme® G993 liquid, and GenSweet® IGI.

While addition of 1 mM $Ca^{2+}$ or more is typically required to ensure adequately high stability of the α-amylase, the free $Ca^{2+}$ strongly inhibits the activity of the glucose isomerase. The $Ca^{2+}$ is thus typically removed prior to isomerization, by means of an expensive unit operation, so that the level of free $Ca^{2+}$ concentration is below 3-5 ppm. Cost savings could be obtained if such an operation were avoided.

AmyE or variants thereof advantageously require less or no added $Ca^{2+}$ for stability. For this reason, the $Ca^{2+}$ added to a liquefaction and/or saccharification reaction may be reduced or eliminated altogether. The removal of $Ca^{2+}$ by ion exchange prior to contacting the reaction mixture with glucose isomerase thus may be avoided, saving time and cost and increasing the efficiency of a process of producing a high fructose syrup.

The starch to be processed may be obtained from tubers, roots, stems, legumes, cereals or whole grain. More specifically, the granular starch may be obtained from corns, cobs, wheat, barley, rye, milo, sago, cassaya, tapioca, sorghum, rice, peas, bean, banana, or potatoes. Specially contemplated are both waxy and non-waxy types of corn and barley. The starch may be a highly refined starch quality, for instance, at least 90%, at least 95%, at least 97%, or at least 99.5% pure. Alternatively, the starch can be a more crude starch containing material comprising milled whole grain, including non-starch fractions such as germ residues and fibers. The raw material, such as whole grain, is milled to open up the structure and allow further processing.

Two milling processes are suitable: wet and dry milling. In dry milling, the whole kernel is milled and used. Wet milling gives a good separation of germ and meal (starch granules and protein) and is usually used in the production of syrups. Both dry and wet milling are well known in the art of starch processing and also are contemplated for use with the compositions and methods disclosed. The process may be conducted in an ultrafiltration system where the retentate is held under recirculation in presence of enzymes, raw starch and water, where the permeate is the soluble starch hydrolysate. Another method is the process conducted in a continuous membrane reactor with ultrafiltration membranes, where the retentate is held under recirculation in presence of enzymes, raw starch and water, and where the permeate is the soluble starch hydrolysate. Also contemplated is the process conducted in a continuous membrane reactor with microfiltration membranes and where the retentate is held under recirculation in presence of enzymes, raw starch and water, and where the permeate is the soluble starch hydrolysate.

Dry milled grain will comprise significant amounts of non-starch carbohydrate compounds, in addition to starch. When such a heterogeneous material is processed by jet cooking, often only a partial gelatinization of the starch is achieved. Accordingly, AmyE or variants thereof having a high activity towards ungelatinized starch are advantageously applied in a process comprising liquefaction and/or saccharification jet cooked dry milled starch.

The starch slurry to be used in any of the above aspects may have about 20% to about 55% dry solids granular starch, about 25% to about 40% dry solids granular starch, or about 30% to about 35% dry solids granular starch. The enzyme variant converts the soluble starch into a soluble starch hydrolysate of the granular starch in the amount of at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

In another embodiment, the AmyE or variant thereof is used in a process comprising fermentation to produce a fermentation product, e.g., ethanol. Such a process for producing ethanol from starch-containing material by fermentation comprises: (i) liquefying the starch-containing material with an AmyE or variant thereof; (ii) saccharifying the liquefied mash obtained; and (iii) fermenting the material obtained in step (ii) in the presence of a fermenting organism. Optionally the process further comprises recovery of the ethanol. During the fermentation, the ethanol content reaches at least about 7%, at least about 8%, at least about 9%, at least about 10% such as at least about 11%, at least about 12%, at least about 13%, at least about 14%, at least 15%, or at least 16% ethanol.

The saccharification and fermentation processes may be carried out as a simultaneous saccharification and fermentation (SSF) process. When fermentation is performed simultaneously with the hydrolysis, the temperature can be between 30° C. and 35° C., particularly between 31° C. and 34° C. The process may be conducted in an ultrafiltration system where the retentate is held under recirculation in presence of enzymes, raw starch, yeast, yeast nutrients and water and where the permeate is an ethanol containing liquid. Also contemplated is the process conducted in a continuous membrane reactor with ultrafiltration membranes and where the retentate is held under recirculation in presence of enzymes, raw starch, yeast, yeast nutrients and water and where the permeate is an ethanol containing liquid.

The soluble starch hydrolysate of the process may also be used for production of a fermentation product comprising fermenting the treated starch into a fermentation product, such as citric acid, monosodium glutamate, gluconic acid, sodium gluconate, calcium gluconate, potassium gluconate, glucono delta-lactone, or sodium erythorbate.

5.2. Cleaning and Dishwashing Compositions and Use

The AmyE or variants thereof discussed herein can be formulated in detergent compositions for use in cleaning dishes or other cleaning compositions, for example. These can be gels, powders or liquids. The compositions can comprise the α-amylase variant alone, other amylolytic enzymes, other cleaning enzymes, and other components common to cleaning compositions.

Thus, a dishwashing detergent composition can comprise a surfactant. The surfactant may be anionic, non-ionic, cationic, amphoteric or a mixture of these types. The detergent can contain 0% to about 90% by weight of a non-ionic surfactant, such as low- to non-foaming ethoxylated propoxylated straight-chain alcohols.

In the detergent applications, AmyE or variants thereof are usually used in a liquid composition containing propylene glycol. The AmyE or variants thereof can be solubilized in propylene glycol, for example, by circulating in a 25% volume/volume propylene glycol solution containing 10% calcium chloride.

The dishwashing detergent composition may contain detergent builder salts of inorganic and/or organic types. The detergent builders may be subdivided into phosphorus-containing and non-phosphorus-containing types. The detergent composition usually contains about 1% to about 90% of detergent builders. Examples of phosphorus-containing inorganic alkaline detergent builders, when present, include the water-soluble salts, especially alkali metal pyrophosphates, orthophosphates, and polyphosphates. An example of phosphorus-containing organic alkaline detergent builder, when present, includes the water-soluble salts of phosphonates. Examples of non-phosphorus-containing inorganic builders, when present, include water-soluble alkali metal carbonates, borates, and silicates, as well as the various types of water-insoluble crystalline or amorphous alumino silicates, of which zeolites are the best-known representatives.

Examples of suitable organic builders include the alkali metal; ammonium and substituted ammonium; citrates; succinates; malonates; fatty acid sulphonates; carboxymethoxy succinates; ammonium polyacetates; carboxylates; polycarboxylates; aminopolycarboxylates; polyacetyl carboxylates; and polyhydroxsulphonates.

Other suitable organic builders include the higher molecular weight polymers and co-polymers known to have builder properties, for example appropriate polyacrylic acid, polymaleic and polyacrylic/polymaleic acid copolymers, and their salts.

The cleaning composition may contain bleaching agents of the chlorine/bromine-type or the oxygen-type. Examples of inorganic chlorine/bromine-type bleaches are lithium, sodium or calcium hypochlorite, and hypobromite, as well as chlorinated trisodium phosphate. Examples of organic chlorine/bromine-type bleaches are heterocyclic N-bromo- and N-chloro-imides such as trichloroisocyanuric, tribromoisocyanuric, dibromoisocyanuric, and dichloroisocyanuric acids, and salts thereof with water-solubilizing cations such as potassium and sodium. Hydantoin compounds are also suitable.

The cleaning composition may contain oxygen bleaches, for example in the form of an inorganic persalt, optionally with a bleach precursor or as a peroxy acid compound. Typical examples of suitable peroxy bleach compounds are alkali metal perborates, both tetrahydrates and monohydrates, alkali metal percarbonates, persilicates, and perphosphates. Suitable activator materials include tetraacetylethylenediamine (TAED) and glycerol triacetate. Enzymatic bleach activation systems may also be present, such as perborate or percarbonate, glycerol triacetate and perhydrolase, as disclosed in WO 2005/056783, for example.

The cleaning composition may be stabilized using conventional stabilizing agents for the enzyme(s), e.g., a polyol such as, e.g., propylene glycol, a sugar or a sugar alcohol, lactic acid, boric acid, or a boric acid derivative (e.g., an aromatic borate ester). The cleaning composition may also contain other conventional detergent ingredients, e.g., deflocculant material, filler material, foam depressors, anti-corrosion agents, soil-suspending agents, sequestering agents, anti-soil redeposition agents, dehydrating agents, dyes, bactericides, fluorescent agents, thickeners, and perfumes.

Finally, the AmyE or variants thereof may be used in conventional dishwashing detergents, e.g., in any of the detergents described in the following patent publications, with the consideration that the AmyE or variants thereof disclosed herein are used instead of, or in addition to, any α-amylase disclosed in the listed patents and published applications: CA 2006687, GB 2200132, GB 2234980, GB 2228945, DE 3741617, DE 3727911, DE 4212166, DE 4137470, DE 3833047, DE 4205071, WO 93/25651, WO 93/18129, WO 93/04153, WO 92/06157, WO 92/08777, WO 93/21299, WO 93/17089, WO 93/03129, EP 481547, EP 530870, EP 533239, EP 554943, EP 429124, EP 346137, EP 561452, EP 318204, EP 318279, EP 271155, EP 271156, EP 346136, EP 518719, EP 518720, EP 518721, EP 516553, EP 561446, EP 516554, EP 516555, EP 530635, EP 414197, and U.S. Pat. Nos. 5,112,518; 5,141,664; and 5,240,632.

5.3. Laundry Detergent Compositions and Use

According to the embodiment, one or more AmyE or variant thereof may be a component of a detergent composition. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products; (polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB Patent No. 1,483,591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in U.S. Pat. No. 5,879,920 (Danisco A/S) or EP 238216, for example. Polyols have long been recognized as stabilizers of proteins as well as for improving the solubility of proteins. See, e.g., Kaushik et al., J. Biol. Chem. 278: 26458-65 (2003) and references cited therein; and M. Conti et al., J. Chromatography 757: 237-245 (1997).

The detergent composition may be in any convenient form, e.g., as gels, powders, granules, pastes, or liquids. A liquid detergent may be aqueous, typically containing up to about 70% of water, and 0% to about 30% of organic solvent, it may also be in the form of a compact gel type containing only about 30% water.

The detergent composition comprises one or more surfactants, each of which may be anionic, nonionic, cationic, or zwitterionic. The detergent will usually contain 0% to about 50% of anionic surfactant, such as linear alkylbenzenesulfonate; α-olefinsulfonate; alkyl sulfate (fatty alcohol sulfate) (AS); alcohol ethoxysulfate (AEOS or AES); secondary alkanesulfonates (SAS); α-sulfo fatty acid methyl esters; alkyl- or alkenylsuccinic acid; or soap. The composition may also contain 0% to about 40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide, as described in WO 92/06154, for example.

The detergent composition may additionally comprise one or more other enzymes, such as lipase, cutinase, protease, cellulase, peroxidase, and/or laccase in any combination.

The detergent may contain about 1% to about 65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst). The detergent may also be unbuilt, i.e., essentially free of detergent builder. Enzymes may be used in any composition compatible with the stability of the enzyme. Enzymes can be protected against generally deleterious components by known forms of encapsulation, as by granulation or sequestration in hydro gels, for example. Enzymes and specifically α-amylases either with or without the starch binding domains are not limited to laundry and dishwashing applications, but may bind use in surface cleaners and ethanol production from starch or biomass.

The detergent may comprise one or more polymers. Examples include carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/ acrylic acid copolymers.

The detergent may contain a bleaching system, which may comprise a $H_2O_2$ source such as perborate or percarbonate optionally combined with a peracid-forming bleach activator, such as TAED or nonanoyloxybenzenesulfonate (NOBS). Alternatively, the bleaching system may comprise peroxy acids of the amide, imide, or sulfone type, for example. The bleaching system can also be an enzymatic bleaching system where a perhydrolase activates peroxide, such as that described in WO 2005/056783.

The enzymes of the detergent composition may be stabilized using conventional stabilizing agents, e.g., a polyol such as propylene glycol or glycerol; a sugar or sugar alcohol; lactic acid; boric acid or a boric acid derivative, such as an aromatic borate ester; and the composition may be formulated as described in WO 92/19709 and WO 92/19708, for example.

The detergent may also contain other conventional detergent ingredients such as fabric conditioners including clays, foam boosters, suds suppressors, anti-corrosion agents, soil-suspending agents, anti-soil redeposition agents, dyes, bactericides, optical brighteners, or perfume, for example. The pH (measured in aqueous solution at use concentration) is usually neutral or alkaline, e.g., pH about 7.0 to about 11.0.

The α-amylase variant may be incorporated in concentrations conventionally employed in detergents. It is at present contemplated that, in the detergent composition, the α-amylase variant may be added in an amount corresponding to 0.00001-1.0 mg (calculated as pure enzyme protein) of α-amylase variant per liter of wash liquor. Particular forms of detergent compositions comprising the α-amylase variants can be formulated to include:

(1) A detergent composition formulated as a granulate having a bulk density of at least 600 g/L comprising linear alkylbenzenesulfonate (calculated as acid) about 7% to about 12%; alcohol ethoxysulfate (e.g., $C_{12-18}$ alcohol, 1-2 ethylene oxide (EO)) or alkyl sulfate (e.g., $C_{16-18}$) about 1% to about 4%; alcohol ethoxylate (e.g., $C_{14-15}$ alcohol, 7 EO) about 5% to about 9%; sodium carbonate (e.g., $Na_2CO_3$) about 14% to about 20%; soluble silicate, about 2 to about 6%; zeolite (e.g., $NaAlSiO_4$) about 15% to about 22%; sodium sulfate (e.g., $Na_2SO_4$) 0% to about 6%; sodium citrate/citric acid (e.g., $C_6H_5Na_3O_7/C_6H_8O_7$) about 0% to about 15%; sodium perborate (e.g., $NaBO_3.H_2O$) about 11% to about 18%; TAED about 2% to about 6%; carboxymethylcellulose (CMC) and 0% to about 2%; polymers (e.g., maleic/acrylic acid, copolymer, PVP, PEG) 0-3%; enzymes (calculated as pure enzyme) 0.0001-0.1% protein; and minor ingredients (e.g., suds suppressors, perfumes, optical brightener, photobleach) 0-5%.

(2) A detergent composition formulated as a granulate having a bulk density of at least 600 g/L comprising linear alkylbenzenesulfonate (calculated as acid) about 6% to about 11%; alcohol ethoxysulfate (e.g., $C_{12-18}$ alcohol, 1-2 EO) or alkyl sulfate (e.g., $C_{16-18}$) about 1% to about 3%; alcohol ethoxylate (e.g., $C_{14-15}$ alcohol, 7 EO) about 5% to about 9%; sodium carbonate (e.g., $Na_2CO_3$) about 15% to about 21%; soluble silicate, about 1% to about 4%; zeolite (e.g., $NaAlSiO_4$) about 24% to about 34%; sodium sulfate (e.g., $Na_2SO_4$) about 4% to about 10%; sodium citrate/citric acid (e.g., $C_6H_5Na_3O_7/C_6H_8O_7$) 0% to about 15%; carboxymethylcellulose (CMC) 0% to about 2%; polymers (e.g., maleic/acrylic acid copolymer, PVP, PEG) 1-6%; enzymes (calculated as pure enzyme protein) 0.0001-0.1%; minor ingredients (e.g., suds suppressors, perfume) 0-5%.

(3) A detergent composition formulated as a granulate having a bulk density of at least 600 g/L comprising linear alkylbenzenesulfonate (calculated as acid) about 5% to about 9%; alcohol ethoxylate (e.g., $C_{12-15}$ alcohol, 7 EO) about 7% to about 14%; Soap as fatty acid (e.g., $C_{16-22}$ fatty acid) about 1 to about 3%; sodium carbonate (as $Na_2CO_3$) about 10% to about 17%; soluble silicate, about 3% to about 9%; zeolite (as NaAlSiO$_4$) about 23% to about 33%; sodium sulfate (e.g., Na$_2$SO$_4$) 0% to about 4%; sodium perborate (e.g., NaBO$_3$.H$_2$O) about 8% to about 16%; TAED about 2% to about 8%; phosphonate (e.g., EDTMPA) 0% to about 1%; carboxymethylcellulose (CMC) 0% to about 2%; polymers (e.g., maleic/acrylic acid copolymer, PVP, PEG) 0-3%; enzymes (calculated as pure enzyme protein) 0.0001-0.1%; minor ingredients (e.g., suds suppressors, perfume, optical brightener) 0-5%.

(4) A detergent composition formulated as a granulate having a bulk density of at least 600 g/L comprising linear alkylbenzenesulfonate (calculated as acid) about 8% to about 12%; alcohol ethoxylate (e.g., C$_{12-15}$ alcohol, 7 EO) about 10% to about 25%; sodium carbonate (as Na$_2$CO$_3$) about 14% to about 22%; soluble silicate, about 1% to about 5%; zeolite (e.g., NaAlSiO$_4$) about 25% to about 35%; sodium sulfate (e.g., Na$_2$SO$_4$) 0% to about 10%; carboxymethylcellulose (CMC) 0% to about 2%; polymers (e.g., maleic/acrylic acid copolymer, PVP, PEG) 1-3%; enzymes (calculated as pure enzyme protein) 0.0001-0.1%; and minor ingredients (e.g., suds suppressors, perfume) 0-5%.

(5) An aqueous liquid detergent composition comprising linear alkylbenzenesulfonate (calculated as acid) about 15% to about 21%; alcohol ethoxylate (e.g., C$_{12-15}$ alcohol, 7 EO or C$_{12-15}$ alcohol, 5 EO) about 12% to about 18%; soap as fatty acid (e.g., oleic acid) about 3% to about 13%; alkenylsuccinic acid (C$_{12-14}$) 0% to about 13%; aminoethanol about 8% to about 18%; citric acid about 2% to about 8%; phosphonate 0% to about 3%; polymers (e.g., PVP, PEG) 0% to about 3%; borate (e.g., B$_4$O$_7$) 0% to about 2%; ethanol 0% to about 3%; propylene glycol about 8% to about 14%; enzymes (calculated as pure enzyme protein) 0.0001-0.1%; and minor ingredients (e.g., dispersants, suds suppressors, perfume, optical brightener) 0-5%.

(6) An aqueous structured liquid detergent composition comprising linear alkylbenzenesulfonate (calculated as acid) about 15% to about 21%; alcohol ethoxylate (e.g., C$_{12-15}$ alcohol, 7 EO, or C$_{12-15}$ alcohol, 5 EO) 3-9%; soap as fatty acid (e.g., oleic acid) about 3% to about 10%; zeolite (as NaAlSiO$_4$) about 14% to about 22%; potassium citrate about 9% to about 18%; borate (e.g., B$_4$O$_7$) 0% to about 2%; carboxymethylcellulose (CMC) 0% to about 2%; polymers (e.g., PEG, PVP) 0% to about 3%; anchoring polymers (e.g., lauryl methacrylate/acrylic acid copolymer); molar ratio 25:1, MW 3800) 0% to about 3%; glycerol 0% to about 5%; enzymes (calculated as pure enzyme protein) 0.0001-0.1%; and minor ingredients (e.g., dispersants, suds suppressors, perfume, optical brighteners) 0-5%.

(7) A detergent composition formulated as a granulate having a bulk density of at least 600 g/L comprising fatty alcohol sulfate about 5% to about 10%; ethoxylated fatty acid monoethanolamide about 3% to about 9%; soap as fatty acid 0-3%; sodium carbonate (e.g., Na$_2$CO$_3$) about 5% to about 10%; soluble silicate, about 1% to about 4%; zeolite (e.g., NaAlSiO$_4$) about 20% to about 40%; sodium sulfate (e.g., Na$_2$SO$_4$) about 2% to about 8%; sodium perborate (e.g., NaBO$_3$.H$_2$O) about 12% to about 18%; TAED about 2% to about 7%; polymers (e.g., maleic/acrylic acid copolymer, PEG) about 1% to about 5%; enzymes (calculated as pure enzyme protein) 0.0001-0.1%; and minor ingredients (e.g., optical brightener, suds suppressors, perfume) 0-5%.

(8) A detergent composition formulated as a granulate comprising linear alkylbenzenesulfonate (calculated as acid) about 8% to about 14%; ethoxylated fatty acid monoethanolamide about 5% to about 11%; soap as fatty acid 0% to about 3%; sodium carbonate (e.g., Na$_2$CO$_3$) about 4% to about 10%; soluble silicate, about 1% to about 4%; zeolite (e.g., NaAlSiO$_4$) about 30% to about 50%; sodium sulfate (e.g., Na$_2$SO$_4$) about 3% to about 11%; sodium citrate (e.g., C$_6$H$_5$Na$_3$O$_7$) about 5% to about 12%; polymers (e.g., PVP, maleic/acrylic acid copolymer, PEG) about 1% to about 5%; enzymes (calculated as pure enzyme protein) 0.0001-0.1%; and minor ingredients (e.g., suds suppressors, perfume) 0-5%.

(9) A detergent composition formulated as a granulate comprising linear alkylbenzenesulfonate (calculated as acid) about 6% to about 12%; nonionic surfactant about 1% to about 4%; soap as fatty acid about 2% to about 6%; sodium carbonate (e.g., Na$_2$CO$_3$) about 14% to about 22%; zeolite (e.g., NaAlSiO$_4$) about 18% to about 32%; sodium sulfate (e.g., Na$_2$SO$_4$) about 5% to about 20%; sodium citrate (e.g., C$_6$H$_5$Na$_3$O$_7$) about 3% to about 8%; sodium perborate (e.g., NaBO$_3$.H$_2$O) about 4% to about 9%; bleach activator (e.g., NOBS or TAED) about 1% to about 5%; carboxymethylcellulose (CMC) 0% to about 2%; polymers (e.g., polycarboxylate or PEG) about 1% to about 5%; enzymes (calculated as pure enzyme protein) 0.0001-0.1%; and minor ingredients (e.g., optical brightener, perfume) 0-5%.

(10) An aqueous liquid detergent composition comprising linear alkylbenzenesulfonate (calculated as acid) about 15% to about 23%; alcohol ethoxysulfate (e.g., C$_{12-15}$ alcohol, 2-3 EO) about 8% to about 15%; alcohol ethoxylate (e.g., C$_{12-15}$ alcohol, 7 EO, or C$_{12-15}$ alcohol, 5 EO) about 3% to about 9%; soap as fatty acid (e.g., lauric acid) 0% to about 3%; aminoethanol about 1% to about 5%; sodium citrate about 5% to about 10%; hydrotrope (e.g., sodium toluensulfonate) about 2% to about 6%; borate (e.g., B$_4$O$_7$) 0% to about 2%; carboxymethylcellulose 0% to about 1%; ethanol about 1% to about 3%; propylene glycol about 2% to about 5%; enzymes (calculated as pure enzyme protein) 0.0001-0.1%; and minor ingredients (e.g., polymers, dispersants, perfume, optical brighteners) 0-5%.

(11) An aqueous liquid detergent composition comprising linear alkylbenzenesulfonate (calculated as acid) about 20% to about 32%; alcohol ethoxylate (e.g., C$_{12-15}$ alcohol, 7 EO, or C$_{12-15}$ alcohol, 5 EO) 6-12%; aminoethanol about 2% to about 6%; citric acid about 8% to about 14%; borate (e.g., B$_4$O$_7$) about 1% to about 3%; polymer (e.g., maleic/acrylic acid copolymer, anchoring polymer, such as lauryl methacrylate/acrylic acid copolymer) 0% to about 3%; glycerol about 3% to about 8%; enzymes (calculated as pure enzyme protein) 0.0001-0.1%; and minor ingredients (e.g., hydrotropes, dispersants, perfume, optical brighteners) 0-5%.

(12) A detergent composition formulated as a granulate having a bulk density of at least 600 g/L comprising anionic surfactant (linear alkylbenzenesulfonate, alkyl sulfate, α-olefinsulfonate, a-sulfo fatty acid methyl esters, alkanesulfonates, soap) about 25% to about 40%; nonionic surfactant (e.g., alcohol ethoxylate) about 1% to about 10%; sodium carbonate (e.g., Na$_2$CO$_3$) about 8% to about 25%; soluble silicates, about 5% to about 15%; sodium sulfate (e.g., Na$_2$SO$_4$) 0% to about 5%; zeolite (NaAlSiO$_4$) about 15% to about 28%; sodium perborate (e.g., NaBO$_3$.H$_2$O) 0% to about 20%; bleach activator (TAED or NOBS) about 0% to about 5%; enzymes (calculated as pure enzyme protein) 0.0001-0.1%; minor ingredients (e.g., perfume, optical brighteners) 0-3%.

(13) Detergent compositions as described in compositions 1)-12) supra, wherein all or part of the linear alkylbenzenesulfonate is replaced by (C$_{12}$-C$_{18}$) alkyl sulfate.

(14) A detergent composition formulated as a granulate having a bulk density of at least 600 g/L comprising (C$_{12}$-C$_{18}$) alkyl sulfate about 9% to about 15%; alcohol ethoxylate about 3% to about 6%; polyhydroxy alkyl fatty acid amide about 1% to about 5%; zeolite (e.g., $NaAlSiO_4$) about 10% to about 20%; layered disilicate (e.g., SK56 from Hoechst) about 10% to about 20%; sodium carbonate (e.g., $Na_2CO_3$) about 3% to about 12%; soluble silicate, 0% to about 6%; sodium citrate about 4% to about 8%; sodium percarbonate about 13% to about 22%; TAED about 3% to about 8%; polymers (e.g., polycarboxylates and PVP) 0% to about 5%; enzymes (calculated as pure enzyme protein) 0.0001-0.1%; and minor ingredients (e.g., optical brightener, photobleach, perfume, suds suppressors) 0-5%.

(15) A detergent composition formulated as a granulate having a bulk density of at least 600 g/L comprising ($C_{12}$-$C_{18}$) alkyl sulfate about 4% to about 8%; alcohol ethoxylate about 11% to about 15%; soap about 1% to about 4%; zeolite MAP or zeolite A about 35% to about 45%; sodium carbonate (as $Na_2CO_3$) about 2% to about 8%; soluble silicate, 0% to about 4%; sodium percarbonate about 13% to about 22%; TAED 1-8%; carboxymethylcellulose (CMC) 0% to about 3%; polymers (e.g., polycarboxylates and PVP) 0% to about 3%; enzymes (calculated as pure enzyme protein) 0.0001-0.1%; and minor ingredients (e.g., optical brightener, phosphonate, perfume) 0-3%.

(16) Detergent formulations as described in 1)-15) supra, which contain a stabilized or encapsulated peracid, either as an additional component or as a substitute for already specified bleach systems.

(17) Detergent compositions as described supra in 1), 3), 7), 9), and 12), wherein perborate is replaced by percarbonate.

(18) Detergent compositions as described supra in 1), 3), 7), 9), 12), 14), and 15), which additionally contains a manganese catalyst.

(19) Detergent composition formulated as a non-aqueous detergent liquid comprising a liquid nonionic surfactant such as, e.g., linear alkoxylated primary alcohol, a builder system (e.g., phosphate), an enzyme(s), and alkali. The detergent may also comprise anionic surfactant and/or a bleach system.

In another embodiment, the 2,6-β-D-fructan hydrolase can be incorporated in detergent compositions and used for removal/cleaning of biofilm present on household and/or industrial textile/laundry.

The detergent composition may for example be formulated as a hand or machine laundry detergent composition, including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the detergent composition can comprise 2,6-β-D-fructan hydrolase, one or more α-amylase variants, and one or more other cleaning enzymes, such as a protease, a lipase, a cutinase, a carbohydrase, a cellulase, a pectinase, a mannanase, an arabinase, a galactanase, a xylanase, an oxidase, a laccase, and/or a peroxidase, and/or combinations thereof. In general the properties of the chosen enzyme(s) should be compatible with the selected detergent, (e.g., pH-optimum, compatibility with other enzymatic and non-enzymatic ingredients, etc.), and the enzyme(s) should be present in effective amounts.

Proteases: suitable proteases include those of animal, vegetable or microbial origin. Chemically modified or protein engineered mutants are also suitable. The protease may be a serine protease or a metalloprotease, e.g., an alkaline microbial protease or a trypsin-like protease. Examples of alkaline proteases are subtilisins, especially those derived from *Bacillus* sp., e.g., subtilisin Novo, subtilisin Carlsberg, subtilisin 309 (see, e.g., U.S. Pat. No. 6,287,841), subtilisin 147, and subtilisin 168 (see, e.g., WO 89/06279). Examples of trypsin-like proteases are trypsin (e.g., of porcine or bovine origin), and *Fusarium* proteases (see, e.g., WO 89/06270 and WO 94/25583). Examples of useful proteases also include but are not limited to the variants described in WO 92/19729 and WO 98/20115. Suitable commercially available protease enzymes include Alcalase®, Savinase®, Primase™, Duralase™, Esperase®, and Kannase™ (Novo Nordisk A/S); Maxatase®, Maxacal™, Maxapem™, Properase™, Purafect®, Purafect OxP™, FN2™, and FN3™ (Danisco A/S).

Lipases: suitable lipases include those of bacterial or fungal origin. Chemically modified or protein engineered mutants are included. Examples of useful lipases include, but are not limited to, lipases from *Humicola* (synonym *Thermomyces*), e.g. *H. lanuginosa* (*T. lanuginosus*) (see, e.g., EP 258068 and EP 305216) and *H. insolens* (see, e.g., WO 96/13580); a *Pseudomonas* lipase (e.g., from *P. alcaligenes* or *P. pseudoalcaligenes*; see, e.g., EP 218 272), *P. cepacia* (see, e.g., EP 331 376), *P. stutzeri* (see, e.g., GB 1,372,034), *P. fluorescens*, *Pseudomonas* sp. strain SD 705 (see, e.g., WO 95/06720 and WO 96/27002), *P. wisconsinensis* (see, e.g., WO 96/12012); a *Bacillus* lipase (e.g., from *B. subtilis*; see, e.g., Dartois et al. Biochemica Biophysica Acta, 1131: 253-360 (1993)), *B. stearothermophilus* (see, e.g., JP 64/744992), or *B. pumilus* (see, e.g., WO 91/16422). Additional lipase variants contemplated for use in the formulations include those described, for example, in: WO 92/05249, WO 94/01541, WO 95/35381, WO 96/00292, WO 95/30744, WO 94/25578, WO 95/14783, WO 95/22615, WO 97/04079, WO 97/07202, EP 407225, and EP 260105. Some commercially available lipase enzymes include Lipolase® and Lipolase® Ultra (Novo Nordisk A/S).

Polyesterases: Suitable polyesterases include, but are not limited to, those described in WO 01/34899 (Danisco A/S) and WO 01/14629 (Danisco A/S), and can be included in any combination with other enzymes discussed herein.

Amylases: The compositions can be combined with other α-amylases, such as a non-variant α-amylase. These can include commercially available amylases, such as but not limited to Duramyl®, Termamyl™, Fungamyl® and BAN™ (Novo Nordisk A/S), Rapidase®, and Purastar® (Danisco A/S).

Cellulases: Cellulases can be added to the compositions. Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307; 5,648,263; 5,691,178; 5,776,757; and WO 89/09259, for example. Exemplary cellulases contemplated for use are those having color care benefit for the textile. Examples of such cellulases are cellulases described in EP 0495257; EP 531 372; WO 99/25846 (Danisco A/S), WO 96/34108 (Danisco A/S), WO 96/11262; WO 96/29397; and WO 98/08940, for example. Other examples are cellulase variants, such as those described in WO 94/07998; WO 98/12307; WO 95/24471; PCT/DK98/00299; EP 531 315; U.S. Pat. Nos. 5,457,046; 5,686,593; and 5,763,254. Commercially available cellulases include Celluzyme® and Carezyme® (Novo Nordisk A/S); Clazinase™ and Puradax® HA (Danisco A/S); and KAC-500(B)™ (Kao Corporation).

Peroxidases/Oxidases: Suitable peroxidases/oxidases contemplated for use in the compositions include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include Guardzyme™ (Novo Nordisk A/S), for example.

The detergent enzyme(s) may be included in a detergent composition by adding separate additives containing one or more enzymes, or by adding a combined additive comprising all of these enzymes. A detergent additive, i.e., a separate additive or a combined additive, can be formulated as a granulate, liquid, slurry, etc. Suitable granulate detergent additive formulations include non-dusting granulates.

Non-dusting granulates may be produced, e.g., as disclosed in U.S. Pat. Nos. 4,106,991 and 4,661,452 and optionally may be coated by methods known in the art. Examples of waxy coating materials are poly(ethylene oxide) products (e.g., polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591, for example. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238 216.

The detergent composition may be in any convenient form, e.g., a bar, tablet, gel, powder, granule, paste, or liquid. A liquid detergent may be aqueous, typically containing up to about 70% water, and 0% to about 30% organic solvent. Compact detergent gels containing 30% or less water are also contemplated. The detergent composition comprises one or more surfactants, which may be non-ionic, including semipolar, anionic, cationic, or zwitterionic, or any combination thereof. The surfactants are typically present at a level of from 0.1% to 60% by weight.

When included therein the detergent typically will contain from about 1% to about 40% of an anionic surfactant, such as linear alkylbenzenesulfonate, α-olefinsulfonate, alkyl sulfate (fatty alcohol sulfate), alcohol ethoxysulfate, secondary alkanesulfonate, α-sulfo fatty acid methyl ester, alkyl- or alkenylsuccinic acid, or soap.

When included therein, the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl-N-alkyl derivatives of glucosamine ("glucamides").

The detergent may contain 0% to about 65% of a detergent builder or complexing agent such as zeolite, diphosphate, triphosphate, phosphonate, carbonate, citrate, nitrilotriacetic acid, ethylenediaminetetraacetic acid (EDTA), diethylenetriaminepentaacetic acid, alkyl- or alkenylsuccinic acid, soluble silicates or layered silicates (e.g., SKS-6 from Hoechst).

The detergent may comprise one or more polymers. Examples are carboxymethylcellulose (CMC), poly(vinylpyrrolidone) (PVP), poly(ethylene glycol) (PEG), poly (vinyl alcohol) (PVA), poly(vinylpyridine-N-oxide), poly(vinylimidazole), polycarboxylates, e.g., polyacrylates, maleic/acrylic acid copolymers), and lauryl methacrylate/acrylic acid copolymers.

The detergent may contain a bleaching system that may comprise a source of $H_2O_2$, such as perborate or percarbonate, which may be combined with a peracid-forming bleach activator (e.g., tetraacetylethylenediamine or nonanoyloxybenzenesulfonate). Alternatively, the bleaching system may comprise peroxyacids (e.g., the amide-, imide-, or sulfone-type peroxyacids). The bleaching system can also be an enzymatic bleaching system.

The enzyme(s) of the detergent composition may be stabilized using conventional stabilizing agents, e.g., polyol (e.g., propylene glycol or glycerol), a sugar or sugar alcohol, lactic acid, boric acid, a boric acid derivative (e.g., an aromatic borate ester), or a phenyl boronic acid derivative (e.g., 4-formylphenyl boronic acid). The composition may be formulated as described in WO 92/19709 and WO 92/19708.

The detergent may also contain other conventional detergent ingredients such as e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is contemplated that in the detergent compositions, the enzyme variants may be added in an amount corresponding to about 0.01 to about 100 mg of enzyme protein per liter of wash liquor, particularly about 0.05 to about 5.0 mg of enzyme protein per liter of wash liquor, or even more particularly in 0.1 to about 1.0 mg of enzyme protein per liter of wash liquor.

A representative assay that may be used to test the efficacy of a cleaning composition comprising AmyE or a variant thereof includes a swatch test. A "swatch" is a piece of material such as a fabric that has a stain applied thereto. The material can be, for example, fabrics made of cotton, polyester or mixtures of natural and synthetic fibers. Alternatively, the material can be paper, such as filter paper or nitrocellulose, or a piece of a hard material, such as ceramic, metal, or glass. For α-amylases, the stain is starch based, but can include blood, milk, ink, grass, tea, wine, spinach, gravy, chocolate egg, cheese, clay, pigment, oil, or mixtures of these compounds. In one embodiment, the AmyE or variant thereof is tested in a BMI (blood/milk/ink) assay.

A "smaller swatch" is a piece of the swatch that has been cut with a single hole punch device, or a custom manufactured 96-hole punch device, where the pattern of the multi-hole punch is matched to standard 96-well microtiter plates, or has been otherwise removed from the swatch. The swatch can be of textile, paper, metal, or other suitable material. The smaller swatch can have the stain affixed either before or after it is placed into the well of a 24-, 48- or 96-well microtiter plate. The smaller swatch also can be made by applying a stain to a small piece of material. For example, the smaller swatch can be a piece of fabric with a stain ⅝" or 0.25" in diameter. The custom manufactured punch is designed in such a manner that it delivers 96 swatches simultaneously to all wells of a 96-well plate. The device allows delivery of more than one swatch per well by simply loading the same 96-well plate multiple times. Multi-hole punch devices can be conceived to deliver simultaneously swatches to any format plate, including, but not limited to, 24-well, 48-well, and 96-well plates. In another conceivable method, the soiled test platform can be a bead made of either metal, plastic, glass, ceramic, or other suitable material that is coated with the soil substrate. The one or more coated beads are then placed into wells of 96-, 48-, or 24-well plates or larger formats, containing suitable buffer and enzyme. In this case, supernatant can be examined for released soil either by direct absorbance measurement or after a secondary color development reaction. Analysis of the released soil might also be taken by mass spectral analysis.

In one embodiment, a treatment protocol provides control over degree of fixation of a stain. As a result, it is possible to produce swatches that, for example, release varying amounts of stain when washed in the absence of the enzyme being tested. The use of fixed swatches leads to a dramatic improvement of the signal-to-noise ratio in the wash assays. Furthermore, by varying the degree of fixation, one can generate stains that give optimum results under the various cleaning conditions.

Swatches having stains of known "strength" on various types of material are commercially available (EMPA, St. Gallen, Switzerland; wfk—Testgewebe GmbH, Krefeld Germany; or Center for Test Materials, Vlaardingen, The Netherlands) and/or can be made by the practitioner (Morris and Prato, Textile Research Journal 52(4): 280-286 (1982)). Swatches can comprise, for example, a cotton-containing fabric containing a stain made by blood/milk/ink (BMI), spinach, grass, or chocolate/milk/soot. A BMI stain can be fixed to cotton with 0.0003% to 0.3% hydrogen peroxide, for example. Other combinations include grass or spinach fixed with 0.001% to 1% glutaraldehyde, gelatin and Coomassie stain fixed with 0.001% to 1% glutaraldehyde, or chocolate, milk and soot fixed with 0.001% to 1% glutaraldehyde.

The swatch can also be agitated during incubation with the enzyme and/or detergent formulation. Wash performance data is dependent on the orientation of the swatches in the wells (horizontal versus vertical), particularly in the 96-well plate. This would indicate that mixing was insufficient during the incubation period. Although there are a number of ways to ensure sufficient agitation during incubation, a plate holder in which the microtiter plate is sandwiched between two plates of aluminum can be constructed. This can be as simple as placing, for example, an adhesive plate sealer over the wells then clamping the two aluminum plates to the 96-well plate with any type of appropriate, commercially available clamps. It can then be mounted in a commercial incubator shaker. Setting the shaker to about 400 rpm results in very efficient mixing, while leakage or cross-contamination is efficiently prevented by the holder.

Trinitrobenzenesulfonic acid (TNBS) can be used to quantify the concentration of amino groups in the wash liquor. This can serve as a measure of the amount of protein that was removed from the swatch (see, e.g., Cayot and Tainturier, Anal. Biochem. 249: 184-200 (1997)). However, if a detergent or an enzyme sample leads to the formation of unusually small peptide fragments (for example, from the presence of peptidases in the sample), then one will obtain a larger TNBS signal, i.e., more "noise."

Another means of measuring wash performance of blood/milk/ink that is based on ink release that can be quantified by measuring the absorbance of the wash liquor. The absorbance can be measured at any wavelength between 350 and 800 nm. In one embodiment, the wavelength is measured at 410 nm or 620 nm. The wash liquor can also be examined to determine the wash performance on stains containing grass, spinach, gelatin or Coomassie stain. Suitable wavelengths for these stains include and 670 nm for spinach or grass and 620 nm for gelatin or Coomassie. For example, an aliquot of the wash liquor (typically 100-150 µL from a 96-well microplate, for example) is removed and placed in a cuvette or multiwell microplate. This is then placed in a spectrophotometer and the absorbance is read at an appropriate wavelength. The system also can be used to determine a suitable enzyme and/or detergent composition for dish washing, for example, using a blood/milk/ink stain on a suitable substrate, such as cloth, plastic or ceramic.

In one aspect, a BMI stain is fixed to cotton by applying 0.3% hydrogen peroxide to the BMI/cotton swatch for 30 minutes at 25° C. or by applying 0.03% hydrogen peroxide to the BMI/cotton swatch for 30 minutes at 60° C. Smaller swatches of approximately 0.25" are cut from the BMI/cotton swatch and placed in the wells of a 96-well microtiter plate. Into each well, a known mixture of a detergent composition and an enzyme, such as a variant protein, is placed. After placing an adhesive plate sealer onto the top of the microtiter plate, the microtiter plate is clamped to an aluminum plate and agitated on an orbital shaker at approximately 250 rpm for about 10 to 60 minutes. At the end of this time, the supernatants are transferred to wells in a new microtiter plate and the absorbance of the ink at 620 nm is measured. This can be similarly tests with spinach stains or grass stains fixed to cotton by applying 0.01% glutaraldehyde to the spinach/cotton swatch or grass/cotton swatch for 30 minutes at 25° C. The same can be done with chocolate, milk, and/or soot stains.

5.4. Textile Desizing Compositions and Use

Also contemplated are compositions and methods of treating fabrics (e.g., to desize a textile) using one or more AmyE or variant thereof. The AmyE or variants thereof can be used in any fabric-treating method, which are well known in the art (see, e.g., U.S. Pat. No. 6,077,316). For example, in one aspect, the feel and appearance of a fabric is improved by a method comprising contacting the fabric with an enzyme variant in a solution. In one aspect, the fabric is treated with the solution under pressure.

In one aspect, the enzymes are applied during or after the weaving of textiles, or during the desizing stage, or one or more additional fabric processing steps. During the weaving of textiles, the threads are exposed to considerable mechanical strain. Prior to weaving on mechanical looms, warp yarns are often coated with sizing starch or starch derivatives in order to increase their tensile strength and to prevent breaking. The AmyE or variants thereof can be applied to remove these sizing starch or starch derivatives. After the textiles have been woven, a fabric can proceed to a desizing stage. This can be followed by one or more additional fabric processing steps. Desizing is the act of removing size from textiles. After weaving, the size coating should be removed before further processing the fabric in order to ensure a homogeneous and wash-proof result. Also provided is a method of desizing comprising enzymatic hydrolysis of the size by the action of an enzyme variant.

The AmyE or variants thereof can be used alone or with other desizing chemical reagents and/or desizing enzymes to desize fabrics, including cotton-containing fabrics, as detergent additives, e.g., in aqueous compositions. The AmyE or variants thereof also can be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of amylolytic enzymes to provide softness to the fabric and make the cotton more accessible to the subsequent enzymatic finishing steps. The α-amylase variant can be used in methods of finishing denim garments (e.g., a "bio-stoning process"), enzymatic desizing and providing softness to fabrics, and/or finishing process.

5.5. Compositions and Methods for Baking and Food Preparation

The presently disclosed AmyE or variant thereof also may be used in compositions and methods for baking and food preparation. For the commercial and home use of flour for baking and food production, it is important to maintain an appropriate level of α-amylase activity in the flour. A level of activity that is too high may result in a product that is sticky and/or doughy and unmarketable; but flour with insufficient α-amylase activity may not contain enough sugar for proper yeast function, resulting in dry, crumbly bread. Accordingly, an AmyE or variant thereof, by itself or in combination with another α-amylase(s), may be added to the flour to augment the level of endogenous α-amylase activity in flour. The AmyE or variant thereof typically has a temperature optimum in the presence of starch in the ranges of 30-90° C., 50-80° C., 55-75° C., or 60-70° C., for example. The temperature optimum may be measured in a 1% solution of soluble starch at pH 5.5.

In addition to the use of grains and other plant products in baking, grains such as barley, oats, wheat, as well as plant components, such as corn, hops, and rice are used for brewing, both in industry and for home brewing. The components used in brewing may be unmalted or may be malted, i.e., partially germinated, resulting in an increase in the levels of enzymes, including α-amylase. For successful brewing, adequate levels of α-amylase enzyme activity are necessary to ensure the appropriate levels of sugars for fermentation. An AmyE or variant thereof, by itself or in combination with another α-amylase(s), accordingly may be added to the components used for brewing.

As used herein, the term "flour" means milled or ground cereal grain. The term "flour" also may mean Sago or tuber products that have been ground or mashed. In some embodiments, flour may also contain components in addition to the milled or mashed cereal or plant matter. An example of an additional component, although not intended to be limiting, is a leavening agent. Cereal grains include wheat, oat, rye, and barley. Tuber products include tapioca flour, cassaya flour, and custard powder. The term "flour" also includes ground corn flour, maize-meal, rice flour, whole-meal flour, self-rising flour, tapioca flour, cassaya flour, ground rice, enriched flower, and custard powder.

As used herein, the term "stock" means grains and plant components that are crushed or broken. For example, barley used in beer production is a grain that has been coarsely ground or crushed to yield a consistency appropriate for producing a mash for fermentation. As used herein, the term "stock" includes any of the aforementioned types of plants and grains in crushed or coarsely ground forms. The methods described herein may be used to determine α-amylase activity levels in both flours and stock.

An AmyE or variant thereof further can be added alone or in a combination with other amylases to prevent or retard staling, i.e., crumb firming of baked products. The amount of anti-staling amylase will typically be in the range of 0.01-10 mg of enzyme protein per kg of flour, e.g., 1-10 mg/kg. Additional anti-staling amylases that can be used in combination with an α-amylase variant polypeptide include an endo-amylase, e.g., a bacterial endo-amylase from *Bacillus*. The additional amylase can be a maltogenic α-amylase (EC 3.2.1.133), e.g., from *Bacillus*. Novamyl® is a suitable maltogenic α-amylase from *B. stearothermophilus* strain NCIB 11837 and is described in Christophersen et al., *Starch*, 50(1): 39-45 (1997). Other examples of anti-staling endo-amylases include bacterial α-amylases derived from *Bacillus*, such as *B. licheniformis* or *B. amyloliquefaciens*. The anti-staling amylase may be an exo-amylase, such as β-amylase, e.g., from plant sources, such as soy bean, or from microbial sources, such as *Bacillus*.

The baking composition comprising an AmyE or variant thereof further can comprise a phospholipase. The phospholipase may have $A_1$ or $A_2$ activity to remove fatty acid from the phospholipids, forming a lyso-phospholipid. It may or may not have lipase activity, i.e., activity on triglycerides. The phospholipase typically has a temperature optimum in the range of 30-90° C., e.g., 30-70° C. The added phospholipases can be of animal origin, for example, from pancreas, e.g., bovine or porcine pancreas, snake venom or bee venom. Alternatively, the phospholipase may be of microbial origin, e.g., from filamentous fungi, yeast or bacteria, such as the genus or species *Aspergillus, A. niger; Dictyostelium, D. discoideum; Mucor, M. javanicus, M. mucedo, M. subtilissimus; Neurospora, N. crassa; Rhizomucor, R. pusillus; Rhizopus, R. arrhizus, R. japonicus, R. stolonifer; Sclerotinia, S. libertiana; Trichophyton, T. rubrum; Whetzelinia, W. sclerotiorum; Bacillus, B. megaterium, B. subtilis; Citrobacter, C. freundii; Enterobacter, E. aerogenes, E. cloacae; Edwardsiella, E. tarda; Etwinia, E. herbicola; Escherichia, E. coli; Klebsiella, K. pneumoniae; Proteus, P. vulgaris; Providencia, P. stuartii; Salmonella, S. typhimurium; Serratia, S. liquefasciens, S. marcescens; Shigella, S. flexneri; Streptomyces, S. violeceoruber; Yersinia, Y. enterocolitica; Fusarium, F. oxysporum*, strain DSM 2672), for example.

A phospholipase is added in an amount that improves the softness of the bread during the initial period after baking, particularly the first 24 hours. The amount of phospholipase will typically be in the range of 0.01-10 mg of enzyme protein per kg of flour, e.g., 0.1-5 mg/kg. That is, phospholipase activity generally will be in the range of 20-1000 Lipase Unit (LU)/kg of flour, where a Lipase Unit is defined as the amount of enzyme required to release 1 μmol butyric acid per minute at 30° C., pH 7.0, with gum arabic as emulsifier and tributyrin as substrate.

Compositions of dough generally comprise wheat meal or wheat flour and/or other types of meal, flour or starch such as corn flour, cornstarch, rye meal, rye flour, oat flour, oatmeal, soy flour, sorghum meal, sorghum flour, potato meal, potato flour or potato starch. The dough may be fresh, frozen or par-baked. The dough can be a leavened dough or a dough to be subjected to leavening. The dough may be leavened in various ways, such as by adding chemical leavening agents, e.g., sodium bicarbonate or by adding a leaven, i.e., fermenting dough. Dough also may be leavened by adding a suitable yeast culture, such as a culture of *Saccharomyces cerevisiae* (baker's yeast), e.g., a commercially available strain of *S. cerevisiae*.

The dough may also comprise other conventional dough ingredients, e.g., proteins, such as milk powder, gluten, and soy; eggs (either whole eggs, egg yolks or egg whites); an oxidant, such as ascorbic acid, potassium bromate, potassium iodate, azodicarbonamide (ADA) or ammonium persulfate; an amino acid such as L-cysteine; a sugar; or a salt, such as sodium chloride, calcium acetate, sodium sulfate or calcium sulfate. The dough further may comprise fat, e.g., triglyceride, such as granulated fat or shortening. The dough further may comprise an emulsifier such as mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyethylene stearates, or lysolecithin. In particular, the dough can be made without addition of emulsifiers.

Optionally, an additional enzyme may be used together with the anti-staling amylase and the phospholipase. The additional enzyme may be a second amylase, such as an amyloglucosidase, a β-amylase, a cyclodextrin glucanotransferase, or the additional enzyme may be a peptidase, in particular an exopeptidase, a transglutaminase, a lipase, a cellulase, a hemicellulase, in particular a pentosanase such as xylanase, a protease, a protein disulfide isomerase, e.g., a protein disulfide isomerase as disclosed in WO 95/00636, for example, a glucanotranseferase, a branching enzyme (1,4-α-glucan branching enzyme), a 4-α-glucanotransferase (dextrin glycosyltransferase) or an oxidoreductase, e.g., a peroxidase, a laccase, a glucose oxidase, a pyranose oxidase, a lipoxygenase, an L-amino acid oxidase or a carbohydrate oxidase. The additional enzyme may be of any origin, including mammalian and plant, and particularly of microbial (bacterial, yeast or fungal) origin and may be obtained by techniques conventionally used in the art.

The xylanase is typically of microbial origin, e.g., derived from a bacterium or fungus, such as a strain of *Aspergillus*, in particular of *A. aculeatus, A. niger* (e.g., WO 91/19782), *A. awamori* (e.g., WO 91/18977), or *A. tubigensis* (e.g., WO 92/01793); from a strain of *Trichoderma*, e.g., *T. reesei*, or from a strain of *Humicola*, e.g., *H. insolens* (e.g., WO 92/17573). Pentopan® and Novozym 384® are commercially available xylanase preparations produced from *Trichoderma reesei*. The amyloglucosidase may be an *A. niger* amyloglucosidase (such as AMG®). Other useful amylase products include Grindamyl® A 1000 or A 5000 (available from Grindsted Products, Denmark) and Amylase® H or Amylase® P (available from Gist-Brocades, The Netherlands). The glucose oxidase may be a fungal glucose oxidase, in particular an *Aspergillus niger* glucose oxidase (such as Gluzyme®). An exemplary protease is Neutrase®. An exemplary lipase can be derived from strains of *Thermomyces* (*Humicola*), *Rhizomucor, Candida, Aspergillus, Rhizopus*, or *Pseudomonas*, in particular from *Thermomyces lanuginosus* (*Humicola lanuginosa*), *Rhizomucor miehei, Candida antarctica, Aspergillus niger, Rhizopus delemar* or *Rhizopus arrhizus* or *Pseudomonas cepacia*. In specific embodiments, the lipase may be Lipase A or Lipase B derived from *Candida antarctica* as described in WO 88/02775, for example, or the lipase may be derived from *Rhizomucor miehei* as described in EP 238,023, for example, or *Humicola lanuginosa*, described in EP 305,216, for example, or *Pseudomonas cepacia* as described in EP 214,761 and WO 89/01032, for example.

The process may be used for any kind of baked product prepared from dough, either of a soft or a crisp character, either of a white, light or dark type. Examples are bread, particularly white, whole-meal or rye bread, typically in the form of loaves or rolls, French baguette-type bread, pita bread, tortillas, cakes, pancakes, biscuits, cookies, pie crusts, crisp bread, steamed bread, pizza and the like.

In another embodiment, an AmyE or variant thereof may be used in a pre-mix, comprising flour together with an anti-staling amylase, a phospholipase and a phospholipid. The pre-mix may contain other dough-improving and/or bread-improving additives, e.g., any of the additives, including enzymes, mentioned above. In one aspect, the AmyE or variant thereof is a component of an enzyme preparation comprising an anti-staling amylase and a phospholipase, for use as a baking additive.

The enzyme preparation is optionally in the form of a granulate or agglomerated powder. The preparation can have a narrow particle size distribution with more than 95% (by weight) of the particles in the range from 25 to 500 μm.

Granulates and agglomerated powders may be prepared by conventional methods, e.g., by spraying the AmyE or variant thereof onto a carrier in a fluid-bed granulator. The carrier may consist of particulate cores having a suitable particle size. The carrier may be soluble or insoluble, e.g., a salt (such as NaCl or sodium sulfate), a sugar (such as sucrose or lactose), a sugar alcohol (such as sorbitol), starch, rice, corn grits, or soy.

Another aspect contemplates the enveloping of particles comprising an AmyE or variant thereof, i.e., α-amylase particles. To prepare the enveloped α-amylase particles, the enzyme is contacted with a food grade lipid in sufficient quantity so as to suspend all of the α-amylase particles. Food grade lipids, as used herein, may be any naturally organic compound that is insoluble in water but is soluble in non-polar organic solvents such as hydrocarbon or diethyl ether. Suitable food grade lipids include, but are not limited to, triglycerides either in the form of fats or oils which are either saturated or unsaturated. Examples of fatty acids and combinations thereof which make up the saturated triglycerides include, but are not limited to, butyric (derived from milk fat), palmitic (derived from animal and plant fat), and/or stearic (derived from animal and plant fat). Examples of fatty acids and combinations thereof which make up the unsaturated triglycerides include, but are not limited to, palmitoleic (derived from animal and plant fat), oleic (derived from animal and plant fat), linoleic (derived from plant oils), and/or linolenic (derived from linseed oil). Other suitable food grade lipids include, but are not limited to, monoglycerides and diglycerides derived from the triglycerides discussed above, phospholipids and glycolipids.

The food grade lipid, particularly in the liquid form, is contacted with a powdered form of the α-amylase particles in such a fashion that the lipid material covers at least a portion of the surface of at least a majority, e.g., 100% of the α-amylase particles. Thus, each α-amylase particle is individually enveloped in a lipid. For example, all or substantially all of the α-amylase particles are provided with a thin, continuous, enveloping film of lipid. This can be accomplished by first pouring a quantity of lipid into a container, and then slurrying the α-amylase particles so that the lipid thoroughly wets the surface of each α-amylase particle. After a short period of stirring, the enveloped α-amylase particles, carrying a substantial amount of the lipids on their surfaces, are recovered. The thickness of the coating so applied to the particles of α-amylase can be controlled by selection of the type of lipid used and by repeating the operation in order to build up a thicker film, when desired.

The storing, handling and incorporation of the loaded delivery vehicle can be accomplished by means of a packaged mix. The packaged mix can comprise the enveloped α-amylase. However, the packaged mix may further contain additional ingredients as required by the manufacturer or baker. After the enveloped α-amylase has been incorporated into the dough, the baker continues through the normal production process for that product.

The advantages of enveloping the α-amylase particles are two-fold. First, the food grade lipid protects the enzyme from thermal denaturation during the baking process for those enzymes that are heat labile. Consequently, while the α-amylase is stabilized and protected during the proving and baking stages, it is released from the protective coating in the final baked good product, where it hydrolyzes the glucosidic linkages in polyglucans. The loaded delivery vehicle also provides a sustained release of the active enzyme into the baked good. That is, following the baking process, active α-amylase is continually released from the protective coating at a rate that counteracts, and therefore reduces the rate of, staling mechanisms.

In general, the amount of lipid applied to the α-amylase particles can vary from a few percent of the total weight of the α-amylase to many times that weight, depending upon the nature of the lipid, the manner in which it is applied to the α-amylase particles, the composition of the dough mixture to be treated, and the severity of the dough-mixing operation involved.

The loaded delivery vehicle, i.e., the lipid-enveloped enzyme, is added to the ingredients used to prepare a baked good in an effective amount to extend the shelf-life of the baked good. The baker computes the amount of enveloped α-amylase, prepared as discussed above, that will be required to achieve the desired anti-staling effect. The amount of the enveloped α-amylase required is calculated based on the concentration of enzyme enveloped and on the proportion of α-amylase to flour specified. A wide range of concentrations has been found to be effective, although, as has been discussed, observable improvements in anti-staling do not correspond linearly with the α-amylase concentration, but above certain minimal levels, large increases in α-amylase concentration produce little additional improvement. The α-amylase concentration actually used in a particular bakery production could be much higher than the minimum necessary in order to provide the baker with some insurance against inadvertent under-measurement errors by the baker. The lower limit of enzyme concentration is determined by the minimum anti-staling effect the baker wishes to achieve.

A method of preparing a baked good may comprise: (a) preparing lipid-coated α-amylase particles, wherein substantially 100 percent of the α-amylase particles are coated; (b) mixing a dough containing flour; (c) adding the lipid-coated α-amylase to the dough before the mixing is complete and terminating the mixing before the lipid coating is removed from the α-amylase; (d) proofing the dough; and (e) baking the dough to provide the baked good, wherein the α-amylase is inactive during the mixing, proofing and baking stages and is active in the baked good.

The enveloped α-amylase can be added to the dough during the mix cycle, e.g., near the end of the mix cycle. The enveloped α-amylase is added at a point in the mixing stage that allows sufficient distribution of the enveloped α-amylase throughout the dough; however, the mixing stage is terminated before the protective coating becomes stripped from the α-amylase particle(s). Depending on the type and volume of dough, and mixer action and speed, anywhere from one to six minutes or more might be required to mix the enveloped α-amylase into the dough, but two to four minutes is average. Thus, several variables may determine the precise procedure. First, the quantity of enveloped α-amylase should have a total volume sufficient to allow the enveloped α-amylase to be spread throughout the dough mix. If the preparation of enveloped α-amylase is highly concentrated, additional oil may need to be added to the pre-mix before the enveloped α-amylase is added to the dough. Recipes and production processes may require specific modifications; however, good results generally can be achieved when 25% of the oil specified in a bread dough formula is held out of the dough and is used as a carrier for a concentrated enveloped α-amylase when added near the end of the mix cycle. In bread or other baked goods, recipes which have extremely low fat content (such as French-style breads), it has been found that an enveloped α-amylase mixture of approximately 1% of the dry flour weight is sufficient to admix the enveloped α-amylase properly with the dough, but the range of percentages that may work is extremely wide and depends on the formula, finished product, and production methodology requirements of the individual baker. Second, the enveloped α-amylase suspension should be added to the mix with enough time remaining in the mix cycle for complete mixture into the dough, but not so early that excessive mechanical action will strip the protective lipid coating from a large proportion of the enveloped α-amylase particles.

In another embodiment, bacterial α-amylase (BAA) is added to the lipid-coated particles comprising an AmyE or variant thereof. BAA reduces bread to a gummy mass due to its excessive thermostability and retained activity in the fully baked loaf of bread; however, when BAA is incorporated into the lipid-coated particles, substantial additional anti-staling protection is obtained, even at very low BAA dosage levels. For example, BAA dosages of 150 RAU (Reference Amylase Units) per 100 pounds of flour have been found to be effective. In one embodiment, between about 50 to 2000 RAU of BAA is added to the lipid-coated enzyme product. This low BAA dosage level, combined with the ability of the protective coating to keep enzyme in the fully-baked loaf from free contact with the starches (except when water vapor randomly releases the enzyme from its coating), helps to achieve very high levels of anti-staling activity without the negative side-effects of BAA.

It will be apparent to those skilled in the art that various modifications and variation can be made to the compositions and methods of using same without departing from the spirit or scope of the intended use. Thus, it is the modifications and variations provided they come within the scope of the appended claims and their equivalents.

All references cited herein are incorporated by reference in their entirety for all purposes.

EXAMPLES

Example 1

1.1. Plasmid Construction

Nucleic acids encoding the AmyE of SEQ ID NO: 1 or a C-terminal truncated AmyE variant, AmyE-tr (SEQ ID NO: 2), were cloned into the *B. subtilis* pHPLT expression vector, disclosed in U.S. Pat. No. 5,024,943. FIG. 2 depicts the vector comprising a nucleic acid encoding AmyE-tr.

Referring to FIG. 2, the pHPLT vector contains the *B. licheniformis* LAT promoter ("Plat"), a sequence encoding the LAT signal peptide ("preLAT"), followed by PstI and HpaI restriction sites for cloning. Additional plasmid elements from plasmid pUB110 disclosed in McKenzie et al., *Plasmid* 15(2): 93-103 (1986): "ori-pUB" is the origin of replication from pUB110; "reppUB" is the replicase gene from pUB110, "neo" is the neomycin/kanamycin resistance gene from pUB110; "bleo" is the bleomycin resistance marker, "Tlat" is the transcriptional terminator from *B. licheniformis* amylase.

Plasmid constructs for the expression of AmyE and AmyE-tr were assembled using the AmyE-encoding sequence described by Yang et al, "Nucleotide sequence of the amylase gene from *Bacillus subtilis*," *Nucl. Acids Res.* 11(2): 237-49 (1983). Plasmid pME629.5 contains the nucleic acid encoding the full-length AmyE of SEQ ID NO: 1. The gene has a three base deletion in the sequence encoding the starch binding domain, compared to the sequence described by Yang et al.

Plasmid pME630.7 contains the truncated AmyE sequence, AmyE-tr, and is shown in FIG. 2. AmyE-tr is truncated at D425 of SEQ ID NO: 1. AmyE-tr was designed from a crystal structure of an AmyE variant that lacks the starch binding domain, disclosed in Fujimoto et al., "Crystal structure of a catalytic-site mutant alpha-amylase from *Bacillus subtilis* complexed with maltopentaose," *J. Mol. Biol.* 277: 393-407 (1998). See RCSB Protein Data Bank© Accession No. 1BAG, "Alpha-Amylase From *Bacillus Subtilis* Complexed With Maltopentaose."

For expression plasmid construction, the nucleic acid encoding AmyE was PCR-amplified using Herculase® (Stratagene, Calif.). The PCR products were purified using a column provided in a Qiagen QIAquik™ PCR purification kit (Qiagen, Valencia, Calif.), and resuspended in 50 µL of Milli-Q™-purified water. 50 µL of the purified DNA was digested sequentially with HpaI (Roche) and PstI (Roche), and the resultant DNA resuspended in 30 µL of Milli-Q™-purified water. 10-20 ng/µL DNA was cloned into plasmid pHPLT using PstI and HpaI cloning sites. The ligation mixtures were directly transformed into competent *B. subtilis* cells (genotype: DaprE, DnprE, degUHy32 oppA, DspoIIE3501, amyE::xylRPxylAcomK-phleo). SC6.1 *B. subtilis* cells have a competency gene (comK) which is placed under a xylose-inducible promoter. Competency for DNA binding and uptake is induced by the addition of xylose. Because the AmyE gene in the parent plasmid has two PstI sites, a PCR fusion reaction was carried out to remove these sites before cloning. PCR fusion was done after two separate PCR reactions. The following primers were used for making the pHPLT construct using HpaI and PstI sites:

```
SEQ ID NO: 18: Primer PSTAMYE-F'
CTTCTTGCTGCCTCATTCTGCAGCTTCAGCACTTACAGCACCGTCGATC
AAAAGCGGAAC 3'

SEQ ID NO: 19: Primer AMYENOPST-R'
CTGGAGGCACTATCCTGAAGGATTTCTCCGTATTGGAACTCTGCTGAT
GTATTTGTG SEQ ID NO: 20: Primer AMYENOPST-F'
CACAAATACATCAGCAGAGTTCCAATACGGAGAAATCCTTCAGGATA
GTGCCTCCAG SEQ ID NO: 21: Primer HPAIAMYE-R'
CAGGAAATCCGTCCTCTGTTAACTCAATGGGAAGAGAACCGCTTAAG
CCCGAGTC SEQ ID NO: 22: Primer HPAIAMYE-R'
CAGGAAATCCGTCCTCTGTTAACTCAATCAGGATAAAGCACAGCTACA
GACCTGG SEQ ID NO: 23: Primer AMYE SEQ-F'
TACACAAGTACAGTCCTATCTG 3'

SEQ ID NO: 24: Primer AMYE SEQ-F'
CATCCTCTGTCTCTATCAATAC 3'
```

The plasmids pME629.5 and pME630.7 express AmyE with a 31 residue signal sequence, which is cleaved post-translationally. The subsequent 10 N-terminal amino acids are processed separately as proposed by Yang et al. (1983).

1.2. Protein Expression

Transformants for AmyE full-length and truncated clones were selected on LA with 10 µg/mL neomycin, 1% insoluble starch and incubated overnight at 37° C. Transformants showing a clearing (or halo) around the colony were selected, and vials were made for further studies. Precultures of the transformants were grown for 8 h in LB with 10 µg/mL neomycin. Then, 30 µL of this pre-culture were added into a 250 mL flask filled with 30 mL of cultivation media (described below) supplemented with 10 µg/mL neomycin and 5 mM $CaCl_2$. The cultivation media was an enriched semi-defined media based on MOPs buffer, with urea as the major nitrogen source, glucose as the main carbon source, and supplemented with 1% soytone for robust cell growth. The shake flasks were incubated for 60-65 hours at 37° C., with mixing at 250 rpm. Cultures were harvested by centrifugation at 5000 rpm for 20 minutes in conical tubes. Since both AmyE full-length and AmyE truncated proteins expressed at high levels, the culture supernatants were used for assays without further purification.

Example 2

The following assays were used in the examples described below. Any deviations from the protocols provided below are indicated in the examples. In these experiments, a spectrophotometer was used to measure the absorbance of the products formed after the completion of the reactions.

2.1. Bradford Assay for Protein Content Determination in 96-Well Microtiter Plate Protein concentration in sample supernatants was determined using the Bradford QuickStart™ Dye Reagent (Bio-Rad, California). Samples were obtained by filtration of broths from cultures grown in microtiter plates (MTPs) for 3 days at 37° C. with shaking at 280 rpm and humidified aeration. A 10 µL sample of the culture filtrate was combined with 200 µL Bradford QuickStart™ Dye Reagent in a well of a second MTP. After thorough mixing, the MTP's were incubated for at least 10 minutes at room temperature. Air bubbles were removed and the OD (optical density) was measured at 595 nm. To determine the protein concentration, the background reading (from uninoculated wells) was subtracted from the sample readings.

2.2. Conventional Ethanol Fermentation

Two batches of liquifact (31% DS) obtained from Illinois River Energy, containing 400 ppm urea were adjusted to pH 4.3 and pH 5.8 (using 5N $H_2SO_4$). 100 g substrate was added to a 125 mL Erlenmeyer flask. AmyE-tr and Spezyme® Xtra amylase were dosed at 0.20 mg/g DS. Fermentations were inoculated with 0.2 ml of 10% (w/v) Red Star Ethanol Red yeast pre-hydrated ~45 min in DI water. Flasks were incubated at 32° C. with stir bars at 320 rpm for a 48 h fermentation.

2.3. Ethanol Fermentation on Whole Ground Corn

Two batches of 32% DS corn flour substrate with 400 ppm urea were prepared at pH 4.3 and pH 5.8 (adjusted with 5N $H_2SO_4$). 100 g substrate was added to a 125 ml Erlenmeyer flask. Full length AmyE (SEQ ID NO: 1) and AmyE-tr (SEQ ID NO: 2) were dosed at 0.20 mg/g DS, *A. kawachii* α-amylase (AkAA; SEQ ID NO: 6) was dosed at 1.5 SSU/g DS. The amino acid sequence of AkAA is disclosed in SEQ ID NO: 4 of U.S. Pat. No. 7,332,319. The ability of AmyE and AmyE-tr to hydrolyze whole ground corn was also compared to a mixture of *T. reesei* glucoamylase (TrGA; SEQ ID NO: 7) dosed at 0.5 GAU/g plus *A. kawachii* α-amylase dosed at 1.5 SSU/g DS. The amino acid sequence of TrGA was disclosed in SEQ ID NO: 3 of WO 2006/060062. Fermentations were inoculated with 0.2 ml of 10% (w/v) Red Star Ethanol Red yeast prehydrated ~45 min in DI water. Flasks were incubated at 32° C. with stir bars at 300 rpm for 72 h fermentation.

2.4. Glucose Formation Determination by HPLC Measurement

Hydrolysis of Maltose and Maltoheptaose 0.5% maltose or maltoheptaose solutions were prepared in 50 mM sodium acetate, pH 4.5 or 5.6, or in 50 mM malic acid pH 5.6, as specified for each experiment. All enzyme samples were initially diluted to 1 mg/mL. Reaction mixtures were prepared by diluting the enzyme using the appropriate substrate solutions to give a final enzyme concentration of 1 ppm, then 200 μL aliquots were transferred to sterile screw top tubes and place in a 37° C. incubator. The reactions were stopped at the indicated times by diluting 10-fold into 10 mM sodium hydroxide.

Hydrolysis of Insoluble Starch

For measuring the hydrolysis of insoluble granular starch, purified Amy E (24.5 g/L) was diluted to a final concentration of 20.4 ppm in malic acid buffer, pH 5.6. The protein was then added to a 5% corn flour solution prepared in malic acid buffer, pH 5.6, to a final concentration of 1 ppm, and the mixture was incubated in a shaker at 32° C. Samples were periodically removed and diluted 10 fold into 50 mM NaOH to quench the reaction.

HPLC Detection Method

The formation of glucose and other breakdown products of the substrates were analyzed by HPLC using an Agilent 1100 LC system equipped with a Dionex PA-1 column and electrochemical detector. 10 μL samples were injected and a gradient of NaOH and sodium acetate was applied at 1.0 mL/min at 25° C. The distribution of saccharides was determined from previously run standards. Elution profiles were obtained over 45 minutes. Quantitation of glucose produced (reported as g/L) was obtained using authenticated glucose reference standard (Sigma, Mo.) to convert peak area for the sugars to actual sugar concentrations.

Example 3

Figure 3:
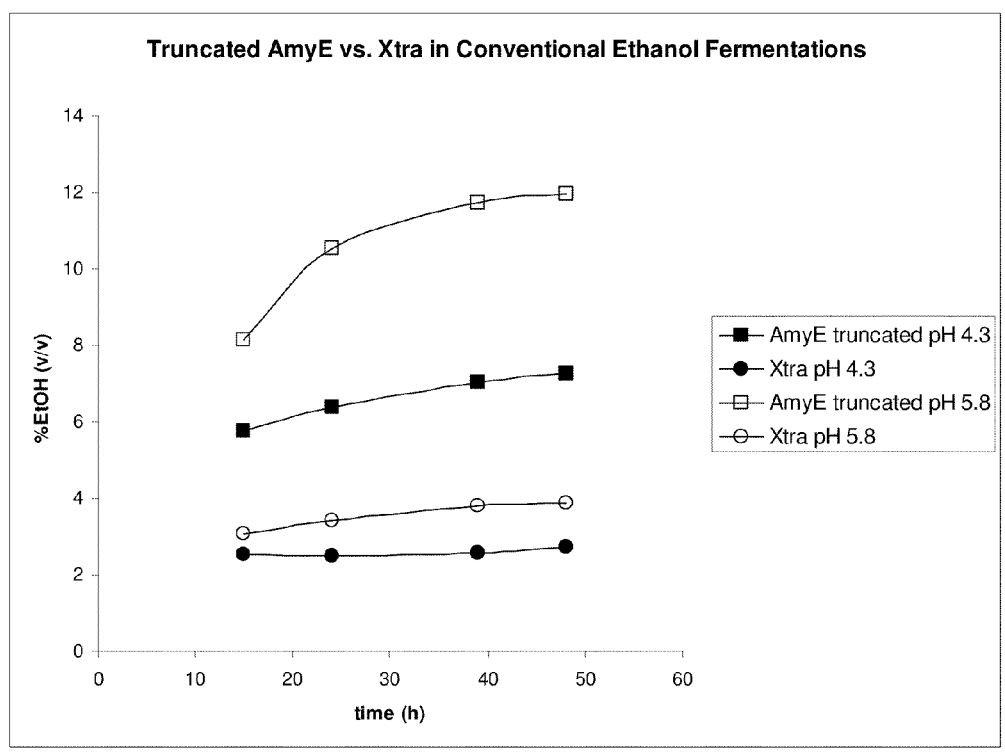
FIG. 3 depicts ethanol formation by AmyE-tr ("AmyE truncated") and Spezyme® Xtra amylase ("Xtra") in conventional fermentation at pH 4.3 and pH 5.8.

The performance of truncated AmyE in conventional ethanol fermentation was tested on Illinois River Energy liquefact (31% DS), using the conventional ethanol fermentation assay described in Example 2.2. The performance of AmyE-tr (SEQ ID NO: 2) was compared to Spezyme® Xtra amylase (AmyR; SEQ ID NO: 5) at pH 4.3 and pH 5.8. Fermentations were carried out for 48 h. AmyE-tr and Spezyme® Xtra amylase were dosed at 0.2 mg/g DS. As shown in FIG. 3, the final ethanol yield produced by AmyE-tr at pH 5.8 is 12.0% (v/v). AmyE-tr at pH 4.3 yielded a final ethanol yield of 7.3% (v/v). Final ethanol yields in the presence of Spezyme® Xtra amylase were 2.7% (v/v) at pH 4.3 and 3.9% (v/v) at pH 5.8. AmyE-tr thus produces significantly more ethanol in conventional ethanol fermentation of liquefact than Spezyme® Xtra amylase. This example also demonstrates that AmyE-tr produces more ethanol at pH 5.8 than at pH 4.3.

Example 4

The ability of AmyE (SEQ ID NO: 1) and AmyE-tr (SEQ ID NO: 2) to catalyze the hydrolysis of insoluble granular (uncooked) starch into ethanol at pH 4.3 and pH 5.8 was compared, using the ethanol fermentation on whole ground corn assay described in Example 2.3. The ethanol forming performance of AmyE and AmyE-tr was compared to *A. kawachii* α-amylase (AkAA, SEQ ID NO: 6), dosed at 1.5 SSU/g, a mixture of *T. reesei* glucoamylase (TrGA; SEQ ID NO: 7) dosed at 0.5 GAU/g plus *A. kawachii* α-amylase dosed at 1.5 SSU/g DS. Both AmyE full-length and truncated AmyE were dosed at 0.2 mg/g DS.

Figure 4:
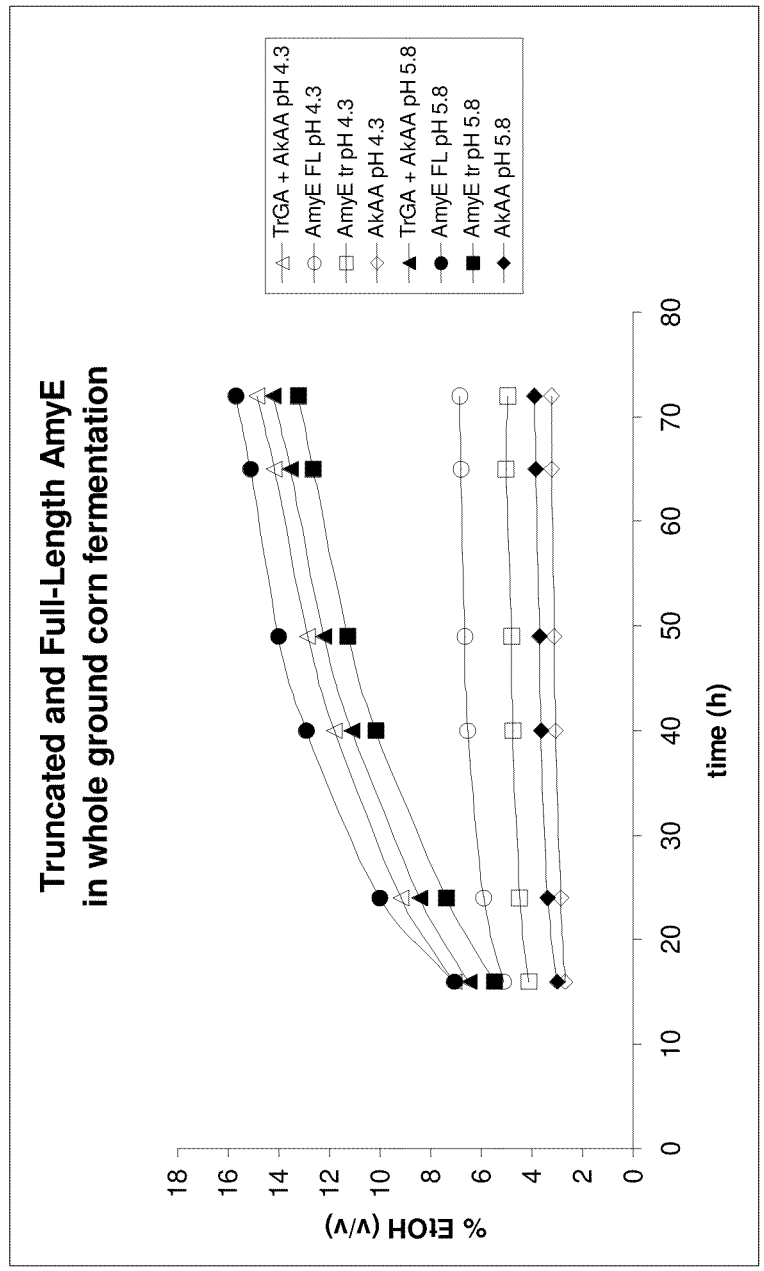
FIG. 4 depicts hydrolysis of insoluble granular (uncooked) starch into ethanol by full length AmyE ("AmyE FL") and AmyE-tr compared to *Aspergillus kawachii* α-amylase (AkAA) alone or a mixture of *A. kawachii* α-amylase and *Trichoderma reesei* glucoamylase (TrGA), at pH 4.3 and pH 5.8.

FIG. 4 shows the final ethanol yield produced by the enzymes at pH 4.3 and pH 5.8. When tested at pH 5.8, both AmyE (—●—) and AmyE-tr (—■—) performed comparably to the TrGA/AkAA (—▲—), with AmyE actually surpassing the ethanol yields observed for TrGA/AkAA. AmyE (—○—) and AmyE-tr (—□—) produced ethanol at pH 4.3, but the yield was not as high as obtained with TrGA/AkAA (—△—). In comparison, AkAA performed poorly at both pHs tested (—♦ ◇—). This example demonstrates that AmyE can completely replace glucoamylase in a saccharification reaction at around pH 5.8. It also demonstrates that AmyE can replace glucoamylase partially or completely in a saccharification reaction at pH 4.3.

Example 5

Figure 5:
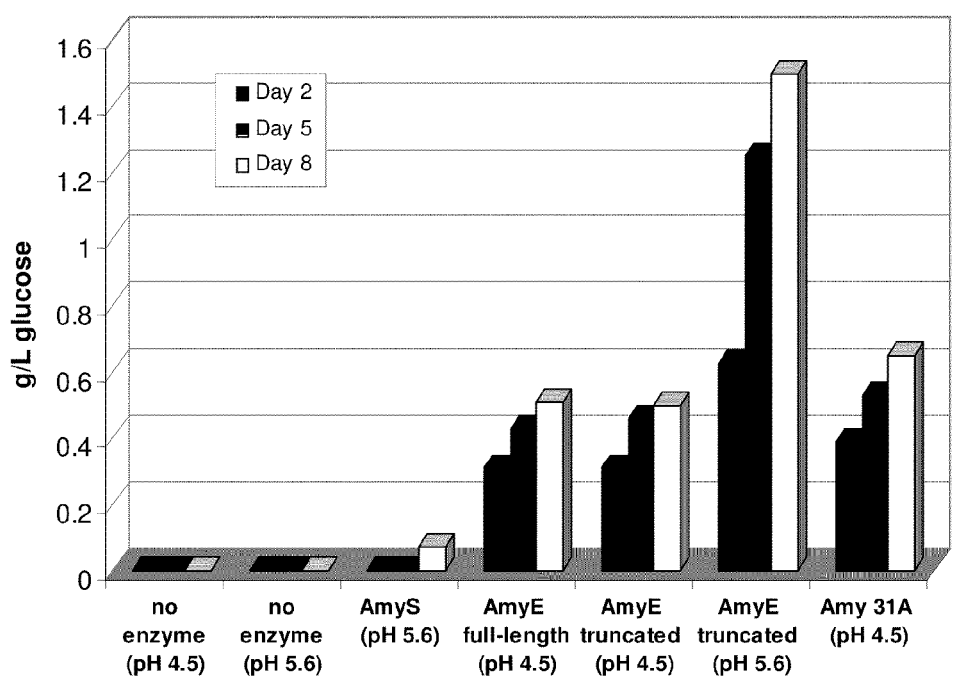
FIG. 5 depicts glucose formation by AmyE ("AmyE full-length"), AmyE-tr ("AmyE truncated"), and Amy 31A compared to *Geobacillus stearothermophilus* α-amylase (AmyS; SEQ ID NO: 4) at pH 4.5 and 5.6.

The ability of AmyE to convert maltose to glucose at pH 4.5 and 5.6 (using sodium acetate buffer) was tested, using the glucose formation assay described in Example 2.4. The reactions were analyzed after 2, 5, and 8 days. As shown in FIG. 5, AmyE (SEQ ID NO: 1), AmyE-tr (SEQ ID NO: 2), and Amy 31A (SEQ ID NO: 3) effectively converted maltose to glucose, whereas *Geobacillus stearothermophilus* α-amylase, AmyS (SEQ ID NO: 4, shown with a 34 amino acid leader sequence), showed only a minimal amount of glucose formation under these conditions.

Example 6

The ability of AmyE (SEQ ID NO: 1) and AmyE-tr (SEQ ID NO: 2) to catalyze the hydrolysis of DP7 or an insoluble, uncooked granular starch was tested. The HPLC method used for detection of saccharides produced from insoluble starch is described in Example 2.4. Degradation products were quantified by HPLC analysis at various times after the reaction was initiated.

Figure 6:
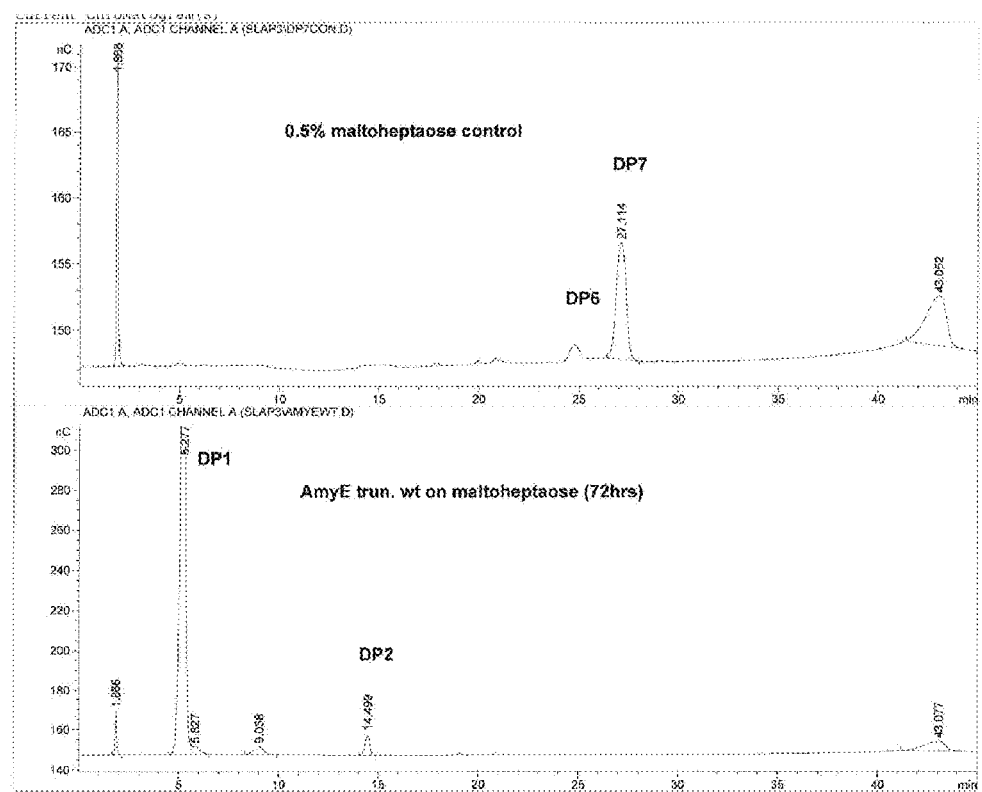
FIG. 6 depicts breakdown products detected by HPLC following a 0 h (top panel) and 72 h incubation (bottom panel) of AmyE-tr with maltoheptaose (DP7).

FIG. 6 depicts hydrolysis products obtained after incubating a 0.5% maltoheptaose substrate in the presence of 1 ppm AmyE-tr for 72 hours. As can be seen in the bottom panel of FIG. 6, AmyE-tr converts nearly all of the DP7 substrate to glucose by 72 hours. The results demonstrate that AmyE is capable of degrading a DP7 substrate to glucose efficiently.

Figure 7:
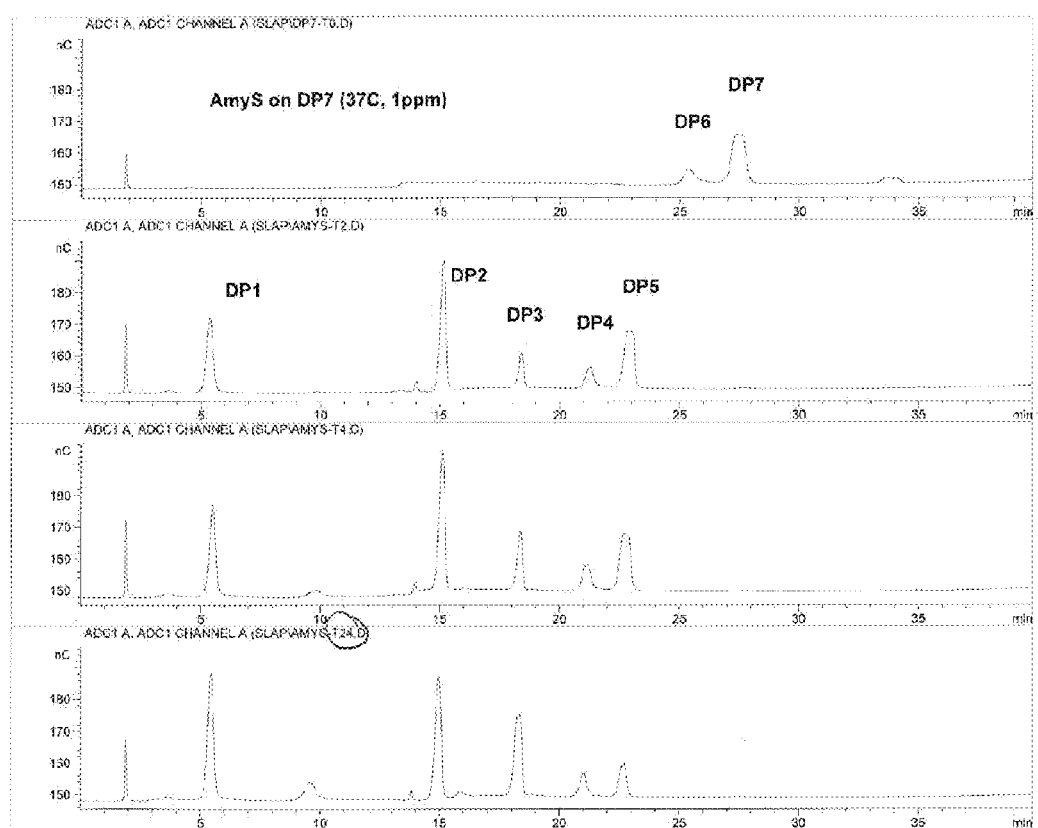
FIG. 7 depicts breakdown products detected by HPLC following a 0 h, 2 h, 4 h, and 24 h (panels from top to bottom) incubation of AmyS with a DP7 substrate.
Figure 8:
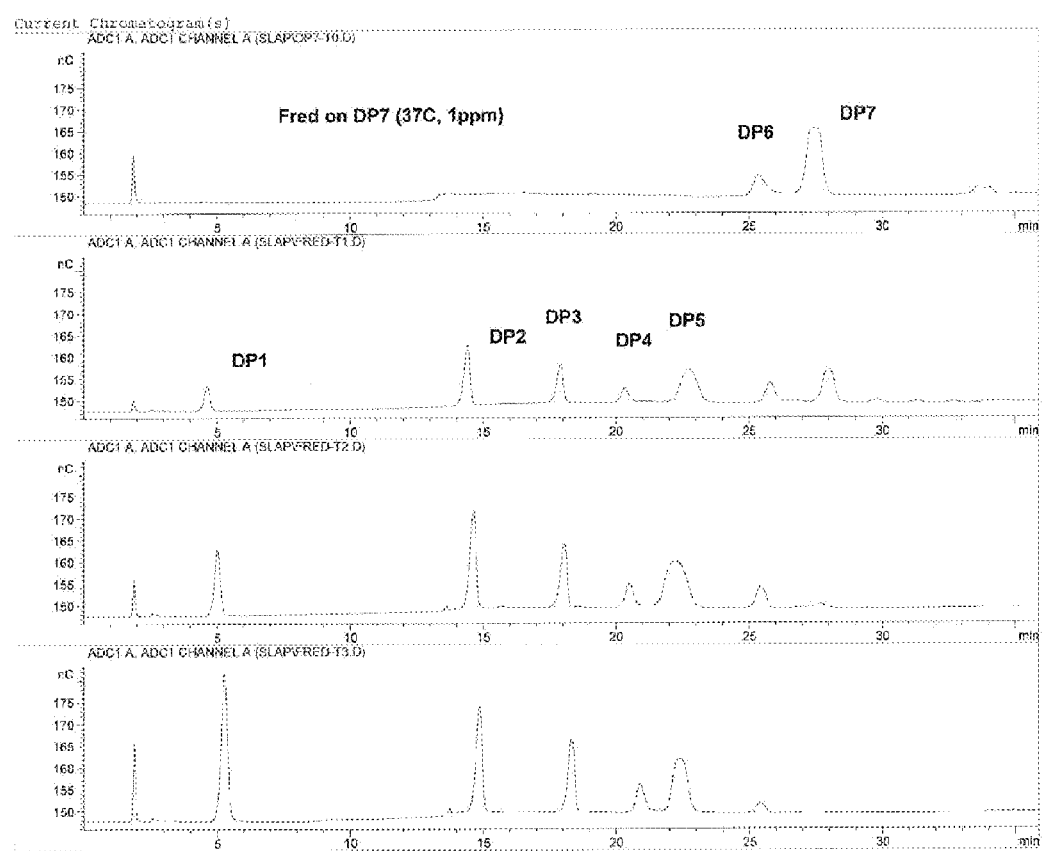
FIG. 8 depicts breakdown products detected by HPLC following a 0 h, 1 h, 2 h, and 3 h (panels from top to bottom) incubation of Spezyme® FRED ("Fred") with a DP7 substrate.

By comparison, the degradation of a DP7 substrate by 1 ppm of either AmyS (SEQ ID NO: 4) or SPEZYME® FRED ("Fred"; SEQ ID NO: 8) is depicted in FIG. 7 and FIG. 8, respectively. Samples from reactions were analyzed using the HPLC procedure set forth in Example 2.4 above. The panels in FIG. 7 from top to bottom represent the reaction products at 0 hours, 2 hours, 4 hours and 24 hours after addition of AmyS. The panels in FIG. 8 from top to bottom represent the reaction products at 0 hours, 1 hours, 2 hours and 3 hours after addition of SPEZYME® FRED. The results show that a considerable portion of the DP7 substrate remains at a degree of polymerization of DP2 or greater in the presence of AmyS or SPEZYME® FRED at the times indicated.

Figure 9:
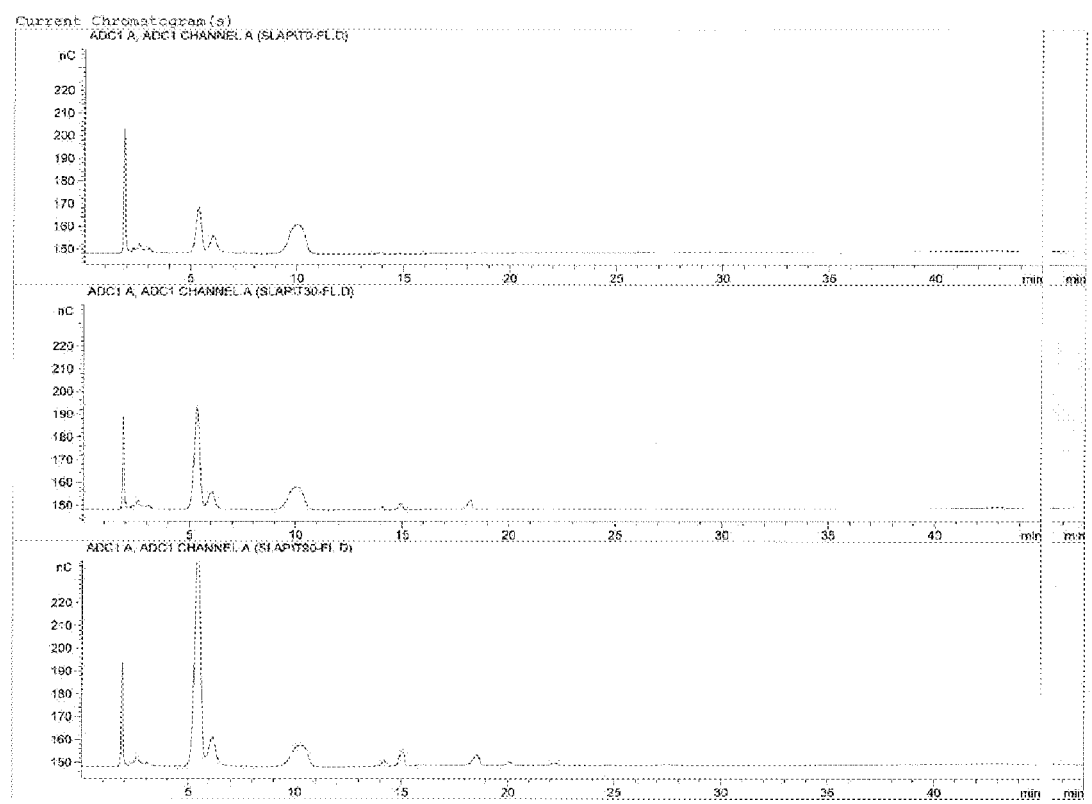
FIG. 9 depicts breakdown products detected by HPLC following a 0 min, 30 min, and 90 (panels from top to bottom) min incubation of AmyE (SEQ ID NO: 1) with raw corn flour starch.

FIG. 9 depicts the results of incubating a 5% corn flour solution with 1 ppm AmyE (SEQ ID NO: 1) at 32° C., according to the procedure set forth in Example 2.4. The results show that AmyE by itself can convert insoluble granular starch efficiently to glucose.

What is claimed is:

1. A method of using a *Bacillus subtilis* α-amylase (AmyE) to produce glucose from an oligosaccharide or starch substrate solution, comprising:
   (i) contacting AmyE with the oligosaccharide or polysaccharide substrate; and
   (ii) converting the substrate solution to a solution comprising glucose, wherein the AmyE consists of the amino acid sequence of SEQ ID NO: 1, wherein said α-amylase (AmyE) is not the α-amylase (AmyE) having the amino acid sequence of SEQ ID NO: 1.

2. The method of claim 1, wherein the oligosaccharide solution comprises predominantly maltoheptaose (DP7) or higher oligosaccharides.

3. The method of claim 1, wherein the starch solution is uncooked corn starch.

4. The method of claim 1, wherein the pH of the substrate solution during said converting is pH 5.6 to pH 5.8.

5. The method of claim 1, where said converting does not comprise contacting the substrate solution with a glucoamylase.

6. The method of claim 1, wherein step (i) further comprises contacting the starch substrate with a glucoamylase or pullulanase.

7. The method of claim 6, wherein the glucoamylase is added to a concentration of less than 0.5 GAU/g ds (glucoamylase activity units per gram of dry solids).

8. The method of claim 7, wherein the glucoamylase is added to a concentration of less than 0.02 GAU/g ds.

9. The method of claim 1, wherein the solution comprising glucose contains at least 0.2 g/L glucose.

10. The method of claim 9, wherein the solution comprising glucose contains at least 0.4 g/L glucose.

11. The method of claim 10, wherein the solution comprising glucose contains at least 1.4 g/L glucose.

12. The method of claim 1, wherein the AmyE comprises the amino acid sequence set forth in SEQ ID NO: 1.

13. The method of claim 1, further comprising (iii) fermenting the solution comprising glucose to produce ethanol.

14. The method of claim 13, wherein the ethanol concentration is at least 6% v/v ethanol.

15. The method of claim 14, wherein the ethanol concentration is at least 14% v/v ethanol.

16. The method of claim 1, further comprising (iii) contacting the solution comprising glucose with a glucose isomerase to produce high fructose corn syrup.

* * * * *

SEQUENCE LISTING

<160> NUMBER OF SEQ ID NOS: 25

<210> SEQ ID NO 1
<211> LENGTH: 618

<212> TYPE: PRT
<213> ORGANISM: Bacillus subtilis

<400> SEQUENCE: 1

```
Leu Thr Ala Pro Ser Ile Lys Ser Gly Thr Ile Leu His Ala Trp Asn
1               5                   10                  15

Trp Ser Phe Asn Thr Leu Lys His Asn Met Lys Asp Ile His Asp Ala
            20                  25                  30

Gly Tyr Thr Ala Ile Gln Thr Ser Pro Ile Asn Gln Val Lys Glu Gly
        35                  40                  45

Asn Gln Gly Asp Lys Ser Met Ser Asn Trp Tyr Trp Leu Tyr Gln Pro
    50                  55                  60

Thr Ser Tyr Gln Ile Gly Asn Arg Tyr Leu Gly Thr Glu Gln Glu Phe
65                  70                  75                  80

Lys Glu Met Cys Ala Ala Glu Glu Tyr Gly Ile Lys Val Ile Val
                85                  90                  95

Asp Ala Val Ile Asn His Thr Thr Ser Asp Tyr Ala Ala Ile Ser Asn
            100                 105                 110

Glu Val Lys Ser Ile Pro Asn Trp Thr His Gly Asn Thr Gln Ile Lys
        115                 120                 125

Asn Trp Ser Asp Arg Trp Asp Val Thr Gln Asn Ser Leu Leu Gly Leu
    130                 135                 140

Tyr Asp Trp Asn Thr Gln Asn Thr Gln Val Gln Ser Tyr Leu Lys Arg
145                 150                 155                 160

Phe Leu Asp Arg Ala Leu Asn Asp Gly Ala Asp Gly Phe Arg Phe Asp
                165                 170                 175

Ala Ala Lys His Ile Glu Leu Pro Asp Asp Gly Ser Tyr Gly Ser Gln
            180                 185                 190

Phe Trp Pro Asn Ile Thr Asn Thr Ser Ala Glu Phe Gln Tyr Gly Glu
        195                 200                 205

Ile Leu Gln Asp Ser Ala Ser Arg Asp Ala Ala Tyr Ala Asn Tyr Met
    210                 215                 220

Asp Val Thr Ala Ser Asn Tyr Gly His Ser Ile Arg Ser Ala Leu Lys
225                 230                 235                 240

Asn Arg Asn Leu Gly Val Ser Asn Ile Ser His Tyr Ala Ser Asp Val
                245                 250                 255

Ser Ala Asp Lys Leu Val Thr Trp Val Glu Ser His Asp Thr Tyr Ala
            260                 265                 270

Asn Asp Asp Glu Glu Ser Thr Trp Met Ser Asp Asp Ile Arg Leu
        275                 280                 285

Gly Trp Ala Val Ile Ala Ser Arg Ser Gly Ser Thr Pro Leu Phe Phe
    290                 295                 300

Ser Arg Pro Glu Gly Gly Gly Asn Gly Val Arg Phe Pro Gly Lys Ser
305                 310                 315                 320

Gln Ile Gly Asp Arg Gly Ser Ala Leu Phe Glu Asp Gln Ala Ile Thr
                325                 330                 335

Ala Val Asn Arg Phe His Asn Val Met Ala Gly Gln Pro Glu Glu Leu
            340                 345                 350

Ser Asn Pro Asn Gly Asn Asn Gln Ile Phe Met Asn Gln Arg Gly Ser
        355                 360                 365

His Gly Val Val Leu Ala Asn Ala Gly Ser Ser Ser Val Ser Ile Asn
    370                 375                 380

Thr Ala Thr Lys Leu Pro Asp Gly Arg Tyr Asp Asn Lys Ala Gly Ala
385                 390                 395                 400
```

Gly Ser Phe Gln Val Asn Asp Gly Lys Leu Thr Gly Thr Ile Asn Ala
            405                 410                 415

Arg Ser Val Ala Val Leu Tyr Pro Asp Asp Ile Ala Lys Ala Pro His
            420                 425                 430

Val Phe Leu Glu Asn Tyr Lys Thr Gly Val Thr His Ser Phe Asn Asp
            435                 440                 445

Gln Leu Thr Ile Thr Leu Arg Ala Asp Ala Asn Thr Thr Lys Ala Val
        450                 455                 460

Tyr Gln Ile Asn Asn Gly Pro Glu Thr Ala Phe Lys Asp Gly Asp Gln
465                 470                 475                 480

Phe Thr Ile Gly Lys Gly Asp Pro Phe Gly Lys Thr Tyr Thr Ile Met
                485                 490                 495

Leu Lys Gly Thr Asn Ser Asp Gly Val Thr Arg Thr Glu Lys Tyr Ser
                500                 505                 510

Phe Val Lys Arg Asp Pro Ala Ser Ala Lys Thr Ile Gly Tyr Gln Asn
            515                 520                 525

Pro Asn His Trp Ser Gln Val Asn Ala Tyr Ile Tyr Lys His Asp Gly
        530                 535                 540

Ser Arg Val Ile Glu Leu Thr Gly Ser Trp Pro Gly Lys Pro Met Thr
545                 550                 555                 560

Lys Asn Ala Asp Gly Ile Tyr Thr Leu Thr Leu Pro Ala Asp Thr Asp
                565                 570                 575

Thr Thr Asn Ala Lys Val Ile Phe Asn Asn Gly Ser Ala Gln Val Pro
            580                 585                 590

Gly Gln Asn Gln Pro Gly Phe Asp Tyr Val Leu Asn Gly Leu Tyr Asn
        595                 600                 605

Asp Ser Gly Leu Ser Gly Ser Leu Pro His
    610                 615

<210> SEQ ID NO 2
<211> LENGTH: 425
<212> TYPE: PRT
<213> ORGANISM: Bacillus subtilis

<400> SEQUENCE: 2

Leu Thr Ala Pro Ser Ile Lys Ser Gly Thr Ile Leu His Ala Trp Asn
1               5                   10                  15

Trp Ser Phe Asn Thr Leu Lys His Asn Met Lys Asp Ile His Asp Ala
                20                  25                  30

Gly Tyr Thr Ala Ile Gln Thr Ser Pro Ile Asn Gln Val Lys Glu Gly
            35                  40                  45

Asn Gln Gly Asp Lys Ser Met Ser Asn Trp Tyr Trp Leu Tyr Gln Pro
        50                  55                  60

Thr Ser Tyr Gln Ile Gly Asn Arg Tyr Leu Gly Thr Glu Gln Glu Phe
65                  70                  75                  80

Lys Glu Met Cys Ala Ala Ala Glu Glu Tyr Gly Ile Lys Val Ile Val
                85                  90                  95

Asp Ala Val Ile Asn His Thr Thr Ser Asp Tyr Ala Ala Ile Ser Asn
            100                 105                 110

Glu Val Lys Ser Ile Pro Asn Trp Thr His Gly Asn Thr Gln Ile Lys
        115                 120                 125

Asn Trp Ser Asp Arg Trp Asp Val Thr Gln Asn Ser Leu Leu Gly Leu
    130                 135                 140

Tyr Asp Trp Asn Thr Gln Asn Thr Gln Val Gln Ser Tyr Leu Lys Arg

```
            145                 150                 155                 160
        Phe Leu Asp Arg Ala Leu Asn Asp Gly Ala Asp Gly Phe Arg Phe Asp
                        165                 170                 175
        Ala Ala Lys His Ile Glu Leu Pro Asp Asp Gly Ser Tyr Gly Ser Gln
                        180                 185                 190
        Phe Trp Pro Asn Ile Thr Asn Thr Ser Ala Glu Phe Gln Tyr Gly Glu
                        195                 200                 205
        Ile Leu Gln Asp Ser Ala Ser Arg Asp Ala Ala Tyr Ala Asn Tyr Met
                        210                 215                 220
        Asp Val Thr Ala Ser Asn Tyr Gly His Ser Ile Arg Ser Ala Leu Lys
        225                 230                 235                 240
        Asn Arg Asn Leu Gly Val Ser Asn Ile Ser His Tyr Ala Ser Asp Val
                        245                 250                 255
        Ser Ala Asp Lys Leu Val Thr Trp Val Glu Ser His Asp Thr Tyr Ala
                        260                 265                 270
        Asn Asp Asp Glu Glu Ser Thr Trp Met Ser Asp Asp Asp Ile Arg Leu
                        275                 280                 285
        Gly Trp Ala Val Ile Ala Ser Arg Ser Gly Ser Thr Pro Leu Phe Phe
                        290                 295                 300
        Ser Arg Pro Glu Gly Gly Gly Asn Gly Val Arg Phe Pro Gly Lys Ser
        305                 310                 315                 320
        Gln Ile Gly Asp Arg Gly Ser Ala Leu Phe Glu Asp Gln Ala Ile Thr
                        325                 330                 335
        Ala Val Asn Arg Phe His Asn Val Met Ala Gly Gln Pro Glu Glu Leu
                        340                 345                 350
        Ser Asn Pro Asn Gly Asn Asn Gln Ile Phe Met Asn Gln Arg Gly Ser
                        355                 360                 365
        His Gly Val Val Leu Ala Asn Ala Gly Ser Ser Ser Val Ser Ile Asn
                        370                 375                 380
        Thr Ala Thr Lys Leu Pro Asp Gly Arg Tyr Asp Asn Lys Ala Gly Ala
        385                 390                 395                 400
        Gly Ser Phe Gln Val Asn Asp Gly Lys Leu Thr Gly Thr Ile Asn Ala
                        405                 410                 415
        Arg Ser Val Ala Val Leu Tyr Pro Asp
                        420                 425

<210> SEQ ID NO 3
<211> LENGTH: 659
<212> TYPE: PRT
<213> ORGANISM: Bacillus subtilis

<400> SEQUENCE: 3

Met Phe Glu Lys Arg Phe Lys Thr Ser Leu Leu Pro Leu Phe Ala Gly
        1               5                   10                  15
        Phe Leu Leu Leu Phe His Leu Val Leu Ser Gly Pro Ala Ala Ala Asn
                        20                  25                  30
        Ala Glu Thr Ala Asn Lys Ser Asn Lys Val Thr Ala Ser Ser Val Lys
                        35                  40                  45
        Asn Gly Thr Ile Leu His Ala Trp Asn Trp Ser Phe Asn Thr Leu Thr
                    50                  55                  60
        Gln Asn Met Lys Asp Ile Arg Asp Ala Gly Tyr Ala Ala Ile Gln Thr
        65                  70                  75                  80
        Ser Pro Ile Asn Gln Val Lys Glu Gly Asn Gln Gly Asp Lys Ser Met
                        85                  90                  95
```

-continued

```
Ser Asn Trp Tyr Trp Leu Tyr Gln Pro Thr Ser Tyr Gln Ile Gly Asn
                100                 105                 110

Arg Tyr Leu Gly Thr Glu Gln Glu Phe Lys Asp Met Cys Ala Ala Ala
            115                 120                 125

Glu Lys Tyr Gly Val Lys Val Ile Val Asp Ala Val Asn His Thr
        130                 135                 140

Thr Ser Asp Tyr Gly Ala Ile Ser Asp Glu Ile Lys Arg Ile Pro Asn
145                 150                 155                 160

Trp Thr His Gly Asn Thr Gln Ile Lys Asn Trp Ser Asp Arg Trp Asp
                165                 170                 175

Ile Thr Gln Asn Ala Leu Leu Gly Leu Tyr Asp Trp Asn Thr Gln Asn
            180                 185                 190

Thr Glu Val Gln Ala Tyr Leu Lys Gly Phe Leu Glu Arg Ala Leu Asn
        195                 200                 205

Asp Gly Ala Asp Gly Phe Arg Tyr Asp Ala Ala Lys His Ile Glu Leu
210                 215                 220

Pro Asp Asp Gly Asn Tyr Gly Ser Gln Phe Trp Pro Asn Ile Thr Asn
225                 230                 235                 240

Thr Ser Ala Glu Phe Gln Tyr Gly Glu Ile Leu Gln Asp Ser Ala Ser
                245                 250                 255

Arg Asp Thr Ala Tyr Ala Asn Tyr Met Asn Val Thr Ala Ser Asn Tyr
            260                 265                 270

Gly His Ser Ile Arg Ser Ala Leu Lys Asn Arg Ile Leu Ser Val Ser
        275                 280                 285

Asn Ile Ser His Tyr Ala Ser Asp Val Ser Ala Asp Lys Leu Val Thr
        290                 295                 300

Trp Val Glu Ser His Asp Thr Tyr Ala Asn Asp Asp Glu Glu Ser Thr
305                 310                 315                 320

Trp Met Ser Asp Asp Asp Ile Arg Leu Gly Trp Ala Val Ile Gly Ser
                325                 330                 335

Arg Ser Gly Ser Thr Pro Leu Phe Phe Ser Arg Pro Glu Gly Gly Gly
            340                 345                 350

Asn Gly Val Arg Phe Pro Gly Lys Ser Gln Ile Gly Asp Arg Gly Ser
        355                 360                 365

Ala Leu Phe Lys Asp Gln Ala Ile Thr Ala Val Asn Gln Phe His Asn
370                 375                 380

Glu Met Ala Gly Gln Pro Glu Glu Leu Ser Asn Pro Asn Gly Asn Asn
385                 390                 395                 400

Gln Ile Phe Met Asn Gln Arg Gly Ser Lys Gly Val Val Leu Ala Asn
                405                 410                 415

Ala Gly Ser Ser Ser Val Thr Ile Asn Thr Ser Thr Lys Leu Pro Asp
            420                 425                 430

Gly Arg Tyr Asp Asn Arg Ala Gly Ala Gly Ser Phe Gln Val Ala Asn
        435                 440                 445

Gly Lys Leu Thr Gly Thr Ile Asn Ala Arg Ser Ala Ala Val Leu Tyr
    450                 455                 460

Pro Asp Asp Ile Gly Asn Ala Pro His Val Phe Leu Glu Asn Tyr Gln
465                 470                 475                 480

Thr Glu Ala Val His Ser Phe Asn Asp Gln Leu Thr Val Thr Leu Arg
                485                 490                 495

Ala Asn Ala Lys Thr Thr Lys Ala Val Tyr Gln Ile Asn Asn Gly Gln
            500                 505                 510

Glu Thr Ala Phe Lys Asp Gly Asp Arg Leu Thr Ile Gly Lys Glu Asp
```

```
            515                 520                 525
Pro Ile Gly Thr Thr Tyr Asn Val Lys Leu Thr Gly Thr Asn Gly Glu
    530                 535                 540

Gly Ala Ser Arg Thr Gln Glu Tyr Thr Phe Val Lys Lys Asp Pro Ser
545                 550                 555                 560

Gln Thr Asn Ile Ile Gly Tyr Gln Asn Pro Asp His Trp Gly Asn Val
                565                 570                 575

Asn Ala Tyr Ile Tyr Lys His Asp Gly Gly Ala Ile Glu Leu Thr
                580                 585                 590

Gly Ser Trp Pro Gly Lys Ala Met Thr Lys Asn Ala Asp Gly Ile Tyr
            595                 600                 605

Thr Leu Thr Leu Pro Ala Asn Ala Asp Thr Ala Asp Ala Lys Val Ile
    610                 615                 620

Phe Asn Asn Gly Ser Ala Gln Val Pro Gly Gln Asn His Pro Gly Phe
625                 630                 635                 640

Asp Tyr Val Gln Asn Gly Leu Tyr Asn Asn Ser Gly Leu Asn Gly Tyr
                645                 650                 655

Leu Pro His

<210> SEQ ID NO 4
<211> LENGTH: 518
<212> TYPE: PRT
<213> ORGANISM: Geobacillus stearothermophilus

<400> SEQUENCE: 4

Met Leu Thr Phe His Arg Ile Ile Arg Lys Gly Trp Met Phe Leu Leu
1               5                   10                  15

Ala Phe Leu Leu Thr Ala Ser Leu Phe Cys Pro Thr Gly Gln His Ala
                20                  25                  30

Lys Ala Ala Ala Pro Phe Asn Gly Thr Met Met Gln Tyr Phe Glu Trp
            35                  40                  45

Tyr Leu Pro Asp Asp Gly Thr Leu Trp Thr Lys Val Ala Asn Glu Ala
    50                  55                  60

Asn Asn Leu Ser Ser Leu Gly Ile Thr Ala Leu Trp Leu Pro Pro Ala
65                  70                  75                  80

Tyr Lys Gly Thr Ser Arg Ser Asp Val Gly Tyr Gly Val Tyr Asp Leu
                85                  90                  95

Tyr Asp Leu Gly Glu Phe Asn Gln Lys Gly Thr Val Arg Thr Lys Tyr
            100                 105                 110

Gly Thr Lys Ala Gln Tyr Leu Gln Ala Ile Gln Ala Ala His Ala Ala
    115                 120                 125

Gly Met Gln Val Tyr Ala Asp Val Val Phe Asp His Lys Gly Gly Ala
130                 135                 140

Asp Gly Thr Glu Trp Val Asp Ala Val Glu Val Asn Pro Ser Asp Arg
145                 150                 155                 160

Asn Gln Glu Ile Ser Gly Thr Tyr Gln Ile Gln Ala Trp Thr Lys Phe
                165                 170                 175

Asp Phe Pro Gly Arg Gly Asn Thr Tyr Ser Ser Phe Lys Trp Arg Trp
            180                 185                 190

Tyr His Phe Asp Gly Val Asp Trp Asp Glu Ser Arg Lys Leu Ser Arg
    195                 200                 205

Ile Tyr Lys Phe Ile Gly Lys Ala Trp Asp Trp Glu Val Asp Thr Glu
210                 215                 220

Asn Gly Asn Tyr Asp Tyr Leu Met Tyr Ala Asp Leu Asp Met Asp His
```

```
                225                 230                 235                 240
Pro Glu Val Val Thr Glu Leu Lys Asn Trp Gly Lys Trp Tyr Val Asn
                    245                 250                 255

Thr Thr Asn Ile Asp Gly Phe Arg Leu Asp Ala Val Lys His Ile Lys
                    260                 265                 270

Phe Ser Phe Phe Pro Asp Trp Leu Ser Tyr Val Arg Ser Gln Thr Gly
            275                 280                 285

Lys Pro Leu Phe Thr Val Gly Glu Tyr Trp Ser Tyr Asp Ile Asn Lys
        290                 295                 300

Leu His Asn Tyr Ile Thr Lys Thr Asn Gly Thr Met Ser Leu Phe Asp
305                 310                 315                 320

Ala Pro Leu His Asn Lys Phe Tyr Thr Ala Ser Lys Ser Gly Gly Ala
                    325                 330                 335

Phe Asp Met Arg Thr Leu Met Thr Asn Thr Leu Met Lys Asp Gln Pro
                340                 345                 350

Thr Leu Ala Val Thr Phe Val Asp Asn His Asp Thr Glu Pro Gly Gln
            355                 360                 365

Ala Leu Gln Ser Trp Val Asp Pro Trp Phe Lys Pro Leu Ala Tyr Ala
        370                 375                 380

Phe Ile Leu Thr Arg Gln Glu Gly Tyr Pro Cys Val Phe Tyr Gly Asp
385                 390                 395                 400

Tyr Tyr Gly Ile Pro Gln Tyr Asn Ile Pro Ser Leu Lys Ser Lys Ile
                    405                 410                 415

Asp Pro Leu Leu Ile Ala Arg Arg Asp Tyr Ala Tyr Gly Thr Gln His
                420                 425                 430

Asp Tyr Leu Asp His Ser Asp Ile Ile Gly Trp Thr Arg Glu Gly Val
            435                 440                 445

Thr Glu Lys Pro Gly Ser Gly Leu Ala Ala Leu Ile Thr Asp Gly Pro
        450                 455                 460

Gly Gly Ser Lys Trp Met Tyr Val Gly Lys Gln His Ala Gly Lys Val
465                 470                 475                 480

Phe Tyr Asp Leu Thr Gly Asn Arg Ser Asp Thr Val Thr Ile Asn Ser
                    485                 490                 495

Asp Gly Trp Gly Glu Phe Lys Val Asn Gly Gly Ser Val Ser Val Trp
                500                 505                 510

Val Pro Arg Lys Thr Thr
            515

<210> SEQ ID NO 5
<211> LENGTH: 486
<212> TYPE: PRT
<213> ORGANISM: Geobacillus stearothermophilus

<400> SEQUENCE: 5

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
            35                  40                  45

Gly Thr Ser Arg Ser Asp Val Gly Tyr Gly Val Tyr Asp Leu Tyr Asp
        50                  55                  60

Leu Gly Glu Phe Asn Gln Lys Gly Thr Val Arg Thr Lys Tyr Gly Thr
65                  70                  75                  80
```

```
Lys Ala Gln Tyr Leu Gln Ala Ile Gln Ala His Ala Ala Gly Met
                85                  90                  95

Gln Val Tyr Ala Asp Val Phe Asp His Lys Gly Ala Asp Gly
            100                 105                 110

Thr Glu Trp Val Asp Ala Val Glu Val Asn Pro Ser Asp Arg Asn Gln
            115                 120                 125

Glu Ile Ser Gly Thr Tyr Gln Ile Gln Ala Trp Thr Lys Phe Asp Phe
            130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
                180                 185                 190

Asn Gly Asn Tyr Asp Tyr Leu Met Tyr Ala Asp Leu Asp Met Asp His
                195                 200                 205

Pro Glu Val Val Thr Glu Leu Lys Asn Trp Gly Lys Trp Tyr Val Asn
                210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
                260                 265                 270

Leu His Asn Tyr Ile Thr Lys Thr Asn Gly Thr Met Ser Leu Phe Asp
                275                 280                 285

Ala Pro Leu His Asn Lys Phe Tyr Thr Ala Ser Lys Ser Gly Gly Ala
                290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
                340                 345                 350

Phe Ile Leu Thr Arg Gln Glu Gly Tyr Pro Cys Val Phe Tyr Gly Asp
                355                 360                 365

Tyr Tyr Gly Ile Pro Gln Tyr Asn Ile Pro Ser Leu Lys Ser Lys Ile
                370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
                420                 425                 430

Gly Gly Ser Lys Trp Met Tyr Val Gly Lys Gln His Ala Gly Lys Val
                435                 440                 445

Phe Tyr Asp Leu Thr Gly Asn Arg Ser Asp Thr Val Thr Ile Asn Ser
                450                 455                 460

Asp Gly Trp Gly Glu Phe Lys Val Asn Gly Gly Ser Val Ser Val Trp
465                 470                 475                 480

Val Pro Arg Lys Thr Thr
                485
```

-continued

```
<210> SEQ ID NO 6
<211> LENGTH: 640
<212> TYPE: PRT
<213> ORGANISM: Aspergillus kawachii

<400> SEQUENCE: 6
```

| | | | | | | | | | | | | | | |
|---|---|---|---|---|---|---|---|---|---|---|---|---|---|---|
| Met | Arg | Val | Ser | Thr | Ser | Ser | Ile | Ala | Leu | Ala | Val | Ser | Leu | Phe | Gly |
| 1 | | | | 5 | | | | | 10 | | | | | 15 | |

Lys Leu Ala Leu Gly Leu Ser Ala Ala Glu Trp Arg Thr Gln Ser Ile
            20                  25                  30

Tyr Phe Leu Leu Thr Asp Arg Phe Gly Arg Thr Asp Asn Ser Thr Thr
        35                  40                  45

Ala Thr Cys Asn Thr Gly Asp Gln Ile Tyr Cys Gly Gly Ser Trp Gln
    50                  55                  60

Gly Ile Ile Asn His Leu Asp Tyr Ile Gln Gly Met Gly Phe Thr Ala
65                  70                  75                  80

Ile Trp Ile Ser Pro Ile Thr Glu Gln Leu Pro Gln Asp Thr Ser Asp
                85                  90                  95

Gly Glu Ala Tyr His Gly Tyr Trp Gln Gln Lys Ile Tyr Asn Val Asn
            100                 105                 110

Ser Asn Phe Gly Thr Ala Asp Asp Leu Lys Ser Leu Ser Asp Ala Leu
        115                 120                 125

His Ala Arg Gly Met Tyr Leu Met Val Asp Val Val Pro Asn His Met
    130                 135                 140

Gly Tyr Ala Gly Asn Gly Asn Asp Val Asp Tyr Ser Val Phe Asp Pro
145                 150                 155                 160

Phe Asp Ser Ser Ser Tyr Phe His Pro Tyr Cys Leu Ile Thr Asp Trp
                165                 170                 175

Asp Asn Leu Thr Met Val Gln Asp Cys Trp Glu Gly Asp Thr Ile Val
            180                 185                 190

Ser Leu Pro Asp Leu Asn Thr Thr Glu Thr Ala Val Arg Thr Ile Trp
        195                 200                 205

Tyr Asp Trp Val Ala Asp Leu Val Ser Asn Tyr Ser Val Asp Gly Leu
    210                 215                 220

Arg Ile Asp Ser Val Glu Glu Val Glu Pro Asp Phe Phe Pro Gly Tyr
225                 230                 235                 240

Gln Glu Ala Ala Gly Val Tyr Cys Val Gly Glu Val Asp Asn Gly Asn
                245                 250                 255

Pro Ala Leu Asp Cys Pro Tyr Gln Lys Tyr Leu Asp Gly Val Leu Asn
            260                 265                 270

Tyr Pro Ile Tyr Trp Gln Leu Leu Tyr Ala Phe Glu Ser Ser Ser Gly
        275                 280                 285

Ser Ile Ser Asn Leu Tyr Asn Met Ile Lys Ser Val Ala Ser Asp Cys
    290                 295                 300

Ser Asp Pro Thr Leu Leu Gly Asn Phe Ile Glu Asn His Asp Asn Pro
305                 310                 315                 320

Arg Phe Ala Ser Tyr Thr Ser Asp Tyr Ser Gln Ala Lys Asn Val Leu
                325                 330                 335

Ser Tyr Ile Phe Leu Ser Asp Gly Ile Pro Ile Val Tyr Ala Gly Glu
            340                 345                 350

Glu Gln His Tyr Ser Gly Gly Asp Val Pro Tyr Asn Arg Glu Ala Thr
        355                 360                 365

Trp Leu Ser Gly Tyr Asp Thr Ser Ala Glu Leu Tyr Thr Trp Ile Ala
    370                 375                 380

```
Thr Thr Asn Ala Ile Arg Lys Leu Ala Ile Ser Ala Asp Ser Asp Tyr
385                 390                 395                 400

Ile Thr Tyr Ala Asn Asp Pro Ile Tyr Thr Asp Ser Asn Thr Ile Ala
                405                 410                 415

Met Arg Lys Gly Thr Ser Gly Ser Gln Ile Ile Thr Val Leu Ser Asn
            420                 425                 430

Lys Gly Ser Ser Gly Ser Ser Tyr Thr Leu Thr Leu Ser Gly Ser Gly
        435                 440                 445

Tyr Thr Ser Gly Thr Lys Leu Ile Glu Ala Tyr Thr Cys Thr Ser Val
    450                 455                 460

Thr Val Asp Ser Asn Gly Asp Ile Pro Val Pro Met Ala Ser Gly Leu
465                 470                 475                 480

Pro Arg Val Leu Leu Pro Ala Ser Val Val Asp Ser Ser Ser Leu Cys
                485                 490                 495

Gly Gly Ser Gly Asn Thr Thr Thr Thr Thr Ala Ala Thr Ser Thr
            500                 505                 510

Ser Lys Ala Thr Thr Ser Ser Ser Ser Ser Ala Ala Ala Thr Thr
        515                 520                 525

Ser Ser Ser Cys Thr Ala Thr Ser Thr Thr Leu Pro Ile Thr Phe Glu
530                 535                 540

Glu Leu Val Thr Thr Thr Tyr Gly Glu Glu Val Tyr Leu Ser Gly Ser
545                 550                 555                 560

Ile Ser Gln Leu Gly Glu Trp Asp Thr Ser Asp Ala Val Lys Leu Ser
                565                 570                 575

Ala Asp Asp Tyr Thr Ser Ser Asn Pro Glu Trp Ser Val Thr Val Ser
                580                 585                 590

Leu Pro Val Gly Thr Thr Phe Glu Tyr Lys Phe Ile Lys Val Asp Glu
                595                 600                 605

Gly Gly Ser Val Thr Trp Glu Ser Asp Pro Asn Arg Glu Tyr Thr Val
            610                 615                 620

Pro Glu Cys Gly Ser Gly Ser Gly Glu Thr Val Val Asp Thr Trp Arg
625                 630                 635                 640

<210> SEQ ID NO 7
<211> LENGTH: 632
<212> TYPE: PRT
<213> ORGANISM: Trichoderma reesei

<400> SEQUENCE: 7

Met His Val Leu Ser Thr Ala Val Leu Leu Gly Ser Val Ala Val Gln
1               5                   10                  15

Lys Val Leu Gly Arg Pro Gly Ser Ser Gly Leu Ser Asp Val Thr Lys
                20                  25                  30

Arg Ser Val Asp Asp Phe Ile Ser Thr Glu Thr Pro Ile Ala Leu Asn
            35                  40                  45

Asn Leu Leu Cys Asn Val Gly Pro Asp Gly Cys Arg Ala Phe Gly Thr
        50                  55                  60

Ser Ala Gly Ala Val Ile Ala Ser Pro Ser Thr Ile Asp Pro Asp Tyr
65                  70                  75                  80

Tyr Tyr Met Trp Thr Arg Asp Ser Ala Leu Val Phe Lys Asn Leu Ile
                85                  90                  95

Asp Arg Phe Thr Glu Thr Tyr Asp Ala Gly Leu Gln Arg Arg Ile Glu
            100                 105                 110

Gln Tyr Ile Thr Ala Gln Val Thr Leu Gln Gly Leu Ser Asn Pro Ser
        115                 120                 125
```

-continued

Gly Ser Leu Ala Asp Gly Ser Leu Gly Glu Pro Lys Phe Glu Leu
    130                 135                 140

Thr Leu Lys Pro Phe Thr Gly Asn Trp Gly Arg Pro Gln Arg Asp Gly
145                 150                 155                 160

Pro Ala Leu Arg Ala Ile Ala Leu Ile Gly Tyr Ser Lys Trp Leu Ile
                165                 170                 175

Asn Asn Asn Tyr Gln Ser Thr Val Ser Asn Val Ile Trp Pro Ile Val
                180                 185                 190

Arg Asn Asp Leu Asn Tyr Val Ala Gln Tyr Trp Asn Gln Thr Gly Phe
            195                 200                 205

Asp Leu Trp Glu Glu Val Asn Gly Ser Ser Phe Phe Thr Val Ala Asn
210                 215                 220

Gln His Arg Ala Leu Val Glu Gly Ala Thr Leu Ala Ala Thr Leu Gly
225                 230                 235                 240

Gln Ser Gly Ser Ala Tyr Ser Ser Val Ala Pro Gln Val Leu Cys Phe
                245                 250                 255

Leu Gln Arg Phe Trp Val Ser Ser Gly Gly Tyr Val Asp Ser Asn Ile
            260                 265                 270

Asn Thr Asn Glu Gly Arg Thr Gly Lys Asp Val Asn Ser Val Leu Thr
            275                 280                 285

Ser Ile His Thr Phe Asp Pro Asn Leu Gly Cys Asp Ala Gly Thr Phe
    290                 295                 300

Gln Pro Cys Ser Asp Lys Ala Leu Ser Asn Leu Lys Val Val Asp
305                 310                 315                 320

Ser Phe Arg Ser Ile Tyr Gly Val Asn Lys Gly Ile Pro Ala Gly Ala
                325                 330                 335

Ala Val Ala Ile Gly Arg Tyr Ala Glu Asp Val Tyr Tyr Asn Gly Asn
            340                 345                 350

Pro Trp Tyr Leu Ala Thr Phe Ala Ala Ala Glu Gln Leu Tyr Asp Ala
            355                 360                 365

Ile Tyr Val Trp Lys Lys Thr Gly Ser Ile Thr Val Thr Ala Thr Ser
370                 375                 380

Leu Ala Phe Phe Gln Glu Leu Val Pro Gly Val Thr Ala Gly Thr Tyr
385                 390                 395                 400

Ser Ser Ser Ser Ser Thr Phe Thr Asn Ile Ile Asn Ala Val Ser Thr
                405                 410                 415

Tyr Ala Asp Gly Phe Leu Ser Glu Ala Ala Lys Tyr Val Pro Ala Asp
            420                 425                 430

Gly Ser Leu Ala Glu Gln Phe Asp Arg Asn Ser Gly Thr Pro Leu Ser
            435                 440                 445

Ala Leu His Leu Thr Trp Ser Tyr Ala Ser Phe Leu Thr Ala Thr Ala
450                 455                 460

Arg Arg Ala Gly Ile Val Pro Pro Ser Trp Ala Asn Ser Ser Ala Ser
465                 470                 475                 480

Thr Ile Pro Ser Thr Cys Ser Gly Ala Ser Val Val Gly Ser Tyr Ser
                485                 490                 495

Arg Pro Thr Ala Thr Ser Phe Pro Pro Ser Gln Thr Pro Lys Pro Gly
            500                 505                 510

Val Pro Ser Gly Thr Pro Tyr Thr Pro Leu Pro Cys Ala Thr Pro Thr
            515                 520                 525

Ser Val Ala Val Thr Phe His Glu Leu Val Ser Thr Gln Phe Gly Gln
530                 535                 540

```
Thr Val Lys Val Ala Gly Asn Ala Ala Ala Leu Gly Asn Trp Ser Thr
545                 550                 555                 560

Ser Ala Ala Val Ala Leu Asp Ala Val Asn Tyr Ala Asp Asn His Pro
                565                 570                 575

Leu Trp Ile Gly Thr Val Asn Leu Glu Ala Gly Asp Val Val Glu Tyr
            580                 585                 590

Lys Tyr Ile Asn Val Gly Gln Asp Gly Ser Val Thr Trp Glu Ser Asp
        595                 600                 605

Pro Asn His Thr Tyr Thr Val Pro Ala Val Ala Cys Val Thr Gln Val
    610                 615                 620

Val Lys Glu Asp Thr Trp Gln Ser
625                 630

<210> SEQ ID NO 8
<211> LENGTH: 483
<212> TYPE: PRT
<213> ORGANISM: Artificial
<220> FEATURE:
<223> OTHER INFORMATION: Synthetic Spezyme Fred sequence

<400> SEQUENCE: 8

Ala Asn Leu Asn Gly Thr Leu Met Gln Tyr Phe Glu Trp Tyr Thr Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu Tyr Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Ser Glu Asn Gly Asn
            180                 185                 190

Tyr Asp Tyr Leu Met Tyr Ala Asp Ile Asp Tyr Asp His Pro Asp Val
        195                 200                 205

Val Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270
```

```
Tyr Leu Asn Lys Thr Asn Phe Asn His Ser Val Phe Asp Val Pro Leu
            275                 280                 285

His Tyr Gln Phe His Ala Ala Ser Thr Gln Gly Gly Gly Tyr Asp Met
        290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
    370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
        435                 440                 445

Trp His Asp Ile Thr Gly Asn Arg Ser Glu Pro Val Val Ile Asn Ser
    450                 455                 460

Glu Gly Trp Gly Glu Phe His Val Asn Gly Gly Ser Val Ser Ile Tyr
465                 470                 475                 480

Val Gln Arg

<210> SEQ ID NO 9
<211> LENGTH: 1854
<212> TYPE: DNA
<213> ORGANISM: Bacillus subtilis

<400> SEQUENCE: 9
cttacagcac cgtcgatcaa aagcggaacc attcttcatg catggaattg gtcgttcaat      60
acgttaaaac acaatatgaa ggatattcat gatgcaggat atacagccat tcagacatct     120
ccgattaacc aagtaaagga agggaatcaa ggagataaaa gcatgtcgaa ctggtactgg     180
ctgtatcagc cgacatcgta tcaaattggc aaccgttact taggtactga acaagaattt     240
aaagaaatgt gtgcagccgc tgaagaatat ggcataaagg tcattgttga cgcggtcatc     300
aatcatacca ccagtgatta tgccgcgatt ccaatgaggt taagagtat tccaaactgg      360 acacatggaa acacacaaat taaaaactgg tctgatcgat gggatgtcac gcagaattca     420
ttgctcgggc tgtatgactg gaatacacaa atacacaag tacagtccta tctgaaacgg      480
ttcttagaca gggcattgaa tgacggggca acggttttc gatttgatgc cgccaaacat      540
atagagcttc cagatgatgg cagttacggc agtcaatttt ggccgaatat cacaaataca     600
tcagcagagt ccaatacgg agaaatcctt caggatagtg cctccagaga tgctgcatat     660
gcgaattata tggatgtgac agcgtctaac tatgggcatt ccataaggtc cgcttttaaag    720 aatcgtaatc tgggcgtgtc gaatatctcc cactatgcat ctgatgtgtc tgcggacaag     780
ctagtgacat gggtagagtc gcatgatacg tatgccaatg atgatgaaga gtcgacatgg     840
atgagcgatg atgatatccg tttaggctgg gcggtgatag cttctcgttc aggcagtacg     900
```

-continued

```
cctcttttct tttccagacc tgagggaggc ggaaatggtg tgaggttccc ggggaaaagc      960
caaataggcg atcgcgggag tgctttattt gaagatcagg ctatcactgc ggtcaataga     1020
tttcacaatg tgatggctgg acagcctgag gaactctcga acccgaatgg aaacaaccag     1080
atatttatga atcagcgcgg ctcacatggc gttgtgctgg caaatgcagg ttcatcctct     1140
gtctctatca atacggcaac aaaattgcct gatggcaggt atgacaataa agctggagcg     1200
ggttcatttc aagtgaacga tggtaaactg acaggcacga tcaatgccag gtctgtagct     1260
gtgctttatc ctgatgatat tgcaaaagcg cctcatgttt tccttgagaa ttacaaaaca     1320
ggtgtaacac attctttcaa tgatcaactg acgattacct gcgtgcaga tgcgaataca      1380 acaaaagccg tttatcaaat caataatgga ccagagacgg cgtttaagga tggagatcaa     1440
ttcacaatcg aaaaggaga tccatttggc aaaacataca ccatcatgtt aaaaggaacg      1500
aacagtgatg gtgtaacgag gaccgagaaa tacagttttg ttaaaagaga tccagcgtcg     1560
gccaaaacca tcggctatca aaatccgaat cattggagcc aggtaaatgc ttatatctat     1620
aaacatgatg ggagccgagt aattgaattg accggatctt ggcctggaaa accaatgact     1680
aaaaatgcag acggaattta cacgctgacg ctgcctgcgg acacggatac aaccaacgca     1740
aaagtgattt taataatgg cagcgcccaa gtgcccggtc agaatcagcc tggctttgat      1800
tacgtgctaa atggtttata taatgactcg ggcttaagcg ttctcttcc ccat            1854
```

<210> SEQ ID NO 10
<211> LENGTH: 1275
<212> TYPE: DNA
<213> ORGANISM: Bacillus subtilis

<400> SEQUENCE: 10

```
cttacagcac cgtcgatcaa aagcggaacc attcttcatg catggaattg gtcgttcaat       60
acgttaaaac acaatatgaa ggatattcat gatgcaggat atacagccat tcagacatct      120
ccgattaacc aagtaaagga agggaatcaa ggagataaaa gcatgtcgaa ctggtactgg      180
ctgtatcagc cgacatcgta tcaaattggc aaccgttact taggtactga acaagaattt      240
aaagaaatgt gtgcagccgc tgaagaatat ggcataaagg tcattgttga cgcggtcatc      300
aatcatacca ccagtgatta tgccgcgatt tccaatgagg ttaagagtat ccaaactgg       360 acacatggaa acacacaaat taaaaactgg tctgatcgat gggatgtcac gcagaattca      420
ttgctcgggc tgtatgactg gaatacacaa aatacacaag tacagtccta tctgaaacgg      480
ttcttagaca gggcattgaa tgacggggca gacggttttc gatttgatgc cgccaaacat      540
atagagcttc cagatgatgg cagttacggc agtcaatttt ggccgaatat cacaaataca      600
tcagcagagt tccaatacgg agaaatcctt caggatagtg cctccagaga tgctgcatat      660
gcgaattata tggatgtgac agcgtctaac tatgggcatt ccataaggtc cgcttttaaag     720 aatcgtaatc tgggcgtgtc gaatatctcc cactatgcat ctgatgtgtc tgcggacaag     780
ctagtgacat gggtagagtc gcatgatacg tatgccaatg atgatgaaga gtcgacatgg     840
atgagcgatg atgatatccg tttaggctgg gcggtgatag cttctcgttc aggcagtacg     900
cctcttttct tttccagacc tgagggaggc ggaaatggtg tgaggttccc ggggaaaagc     960
caaataggcg atcgcgggag tgctttattt gaagatcagg ctatcactgc ggtcaataga    1020
tttcacaatg tgatggctgg acagcctgag gaactctcga acccgaatgg aaacaaccag    1080
atatttatga atcagcgcgg ctcacatggc gttgtgctgg caaatgcagg ttcatcctct    1140
gtctctatca atacggcaac aaaattgcct gatggcaggt atgacaataa agctggagcg    1200
```

```
ggttcatttc aagtgaacga tggtaaactg acaggcacga tcaatgccag gtctgtagct    1260
gtgctttatc ctgat                                                     1275

<210> SEQ ID NO 11
<211> LENGTH: 1842
<212> TYPE: DNA
<213> ORGANISM: Bacillus subtilis

<400> SEQUENCE: 11
tctgttaaaa acggcactat tctgcatgca tggaactgga gctttaacac gctgacccag      60
aacatgaaag atattcgtga cgcgggctat gctgcgatcc aaaccagccc tatcaaccag     120
gtcaaagaag gcaaccaagg cgacaaatcc atgtccaact ggtactggct gtatcaaccg     180
acgtcctatc agattggcaa ccgttatctg ggcacggagc aagagttcaa agacatgtgt     240
gctgcggctg agaaatatgg tgtgaaagtt atcgtggacg ctgtggtaaa ccacacgacc     300
tctgattatg tgctattagc gacgagatt aaacgtattc caaattggac ccatggtaat     360
acccagatca aaaattggag cgaccgctgg acattaccc agaatgcgct gctgggtctg     420
tatgactgga acacgcaaaa caccgaagta caggcatatc tgaagggctt cctggaacgc     480
gctctgaacg atggtgctga tggttttcgc tacgacgccg caaagcatat tgagctgccg     540
gatgacggca actacggttc ccaattctgg ccgaacatca ccaacacctc tgccgaattc     600
cagtacggcg agatcctgca agactccgcg agccgtgaca ccgcttatgc caactatatg     660
aacgtaactg cctctaacta tggccattcc attcgttctg cgctgaaaaa tcgtatcctg     720
tccgtgtcca atatctccca ctatgcatcc gacgtttctg ctgacaaact ggtaacttgg     780
gtcgagtctc acgacaccta tgcaaatgat gacgaggaga gcacctggat gagcgatgat     840
gatattcgtc tgggttgggc ggttattggt tctcgctctg gttctactcc gctgttcttt     900
agccgtccgg aaggtggcgg caatggcgtt cgtttcccgg gtaaatctca aattggtgat     960
cgtggctctg cactgtttaa agatcaagct attacggcgg tgaatcagtt ccataatgag    1020
atggcaggtc aacctgaaga actgtccaat ccaaacggta caaccaaat cttcatgaac     1080 cagcgtggca gcaaaggcgt cgtcctggcg aacgccggta gctcttctgt taccatcaac     1140
acgtctacca aactgccaga cggccgctat gataaccgtg cgggtgctgg ttcctttcag     1200
gtagccaacg gcaagctgac gggcaccatc aacgctcgtt ctgctgctgt tctgtacccg     1260
gacgacattg gcaacgctcc gcacgtgttc ctggagaatt accagaccga gcggtacat     1320 agctttaatg accagctgac cgtcactctg cgtgccaacg caaaaaccac gaaagcagtc     1380
tatcagatca ataatggtca agaaactgct ttcaaggatg gcgaccgtct gactattggt     1440
aaggaggacc cgattggcac cacttataac gttaaactga ctggcaccaa tggcgagggc     1500
gctagccgca ctcaagagta tacgttcgta agaaagacc cgtctcaaac caacatcatc     1560
ggttaccaga atcctgacca ctgggggtaat gtgaacgctt acatctataa acatgatggt     1620
ggcggtgcta tcgaactgac cggctcttgg ccaggtaaag ccatgacgaa aaacgcggat     1680
ggcatctata ccctgaccct gccggccaat gcggataccg cagatgcgaa ggttatcttc     1740
aataacggct ccgcgcaggt tccgggccaa aaccatccgg gctttgacta cgtacaaaat     1800
ggtctgtata caaactctgg cctgaacggt tacctgccgc ac                       1842

<210> SEQ ID NO 12
<211> LENGTH: 1452
<212> TYPE: DNA
```

<213> ORGANISM: Geobacillus stearothermophilus

<400> SEQUENCE: 12

| | | | | | |
|---|---|---|---|---|---|
| gccgcaccgt | ttaacggtac | catgatgcag | tattttgaat | ggtacttgcc | ggatgatggc | 60 |
| acgttatgga | ccaaagtggc | caatgaagcc | aacaacttat | ccagccttgg | catcaccgct | 120 |
| ctttggctgc | cgcccgctta | caaaggaaca | agccgcagcg | acgtagggta | cggagtatac | 180 |
| gacttgtatg | acctcggcga | attcaatcaa | aaagggaccg | tccgcacaaa | atatggaaca | 240 |
| aaagctcaat | atcttcaagc | cattcaagcc | gcccacgccg | ctggaatgca | agtgtacgcc | 300 |
| gatgtcgtgt | tcgaccataa | aggcggcgct | gacggcacgg | aatgggtgga | cgccgtcgaa | 360 |
| gtcaatccgt | ccgaccgcaa | ccaagaaatc | tcgggcacct | atcaaatcca | agcatggacg | 420 |
| aaatttgatt | tccccgggcg | gggcaacacc | tactccagct | ttaagtggcg | ctggtaccat | 480 |
| tttgacggcg | ttgactggga | cgaaagccga | aaattaagcc | gcatttacaa | attcatcggc | 540 |
| aaagcgtggg | attgggaagt | agacacagaa | acggaaact | atgactactt | aatgtatgcc | 600 |
| gaccttgata | tggatcatcc | cgaagtcgtg | accgagctga | aaaactgggg | gaatggtat | 660 |
| gtcaacacaa | cgaacattga | tgggttccgg | cttgatgccg | tcaagcatat | taagttcagt | 720 |
| ttttttcctg | attggttgtc | gtatgtgcgt | tctcagactg | gcaagccgct | atttaccgtc | 780 |
| ggggaatatt | ggagctatga | catcaacaag | ttgcacaatt | acattacgaa | aacaaacgga | 840 |
| acgatgtctt | tgtttgatgc | cccgttacac | aacaaatttt | ataccgcttc | caaatcaggg | 900 |
| ggcgcatttg | atatgcgcac | gttaatgacc | aatactctca | tgaaagatca | accgacattg | 960 |
| gccgtcacct | tcgttgataa | tcatgacacc | gaacccggcc | aagcgctgca | gtcatgggtc | 1020 |
| gacccatggt | tcaaaccgtt | ggcttacgcc | tttattctaa | ctcggcagga | aggatacccg | 1080 |
| tgcgtctttt | atggtgacta | ttatggcatt | ccacaatata | acattccttc | gctgaaaagc | 1140 |
| aaaatcgatc | cgctcctcat | cgcgcgcagg | gattatgctt | acggaacgca | acatgattat | 1200 |
| cttgatcact | ccgacatcat | cggtggaca | agggaagggg | tcactgaaaa | accaggatcc | 1260 |
| gggctggccg | cactgatcac | cgatgggccg | ggaggaagca | aatggatgta | cgttggcaaa | 1320 |
| caacacgctg | aaaagtgtt | ctatgacctt | accggcaacc | ggagtgacac | cgtcaccatc | 1380 |
| aacagtgatg | gatgggggga | attcaaagtc | aatggcggtt | cggtttcggt | ttgggttcct | 1440 |
| agaaaaacga | cc | | | | | 1452 |

<210> SEQ ID NO 13
<211> LENGTH: 1458
<212> TYPE: DNA
<213> ORGANISM: Geobacillus stearothermophilus

<400> SEQUENCE: 13

| | | | | | |
|---|---|---|---|---|---|
| gccgcaccgt | ttaacggtac | catgatgcag | tattttgaat | ggtacttgcc | ggatgatggc | 60 |
| acgttatgga | ccaaagtggc | caatgaagcc | aacaacttat | ccagccttgg | catcaccgct | 120 |
| ctttggctgc | cgcccgctta | caaaggaaca | agccgcagcg | acgtagggta | cggagtatac | 180 |
| gacttgtatg | acctcggcga | attcaatcaa | aaagggaccg | tccgcacaaa | atatggaaca | 240 |
| aaagctcaat | atcttcaagc | cattcaagcc | gcccacgccg | ctggaatgca | agtgtacgcc | 300 |
| gatgtcgtgt | tcgaccataa | aggcggcgct | gacggcacgg | aatgggtgga | cgccgtcgaa | 360 |
| gtcaatccgt | ccgaccgcaa | ccaagaaatc | tcgggcacct | atcaaatcca | agcatggacg | 420 |
| aaatttgatt | tccccgggcg | gggcaacacc | tactccagct | ttaagtggcg | ctggtaccat | 480 |
| tttgacggcg | ttgattggga | cgaaagccga | aaattaagcc | gcatttacaa | attcaggggc | 540 |

```
atcggcaaag cgtgggattg ggaagtagac acagaaaacg gaaactatga ctacttaatg      600
tatgccgacc ttgatatgga tcatcccgaa gtcgtgaccg agctgaaaaa ctggggaaa       660 tggtatgtca acacaacgaa cattgatggg ttccggcttg atgccgtcaa gcatattaag     720
ttcagttttt ttcctgattg gttgtcgtat gtgcgttctc agactggcaa gccgctattt     780
accgtcgggg aatattggag ctatgacatc aacaagttgc acaattacat tacgaaaaca     840
aacggaacga tgtctttgtt tgatgccccg ttacacaaca aattttatac cgcttccaaa     900 tcaggggcg catttgatat gcgcacgtta atgaccaata ctctcatgaa agatcaaccg      960
acattggccg tcaccttcgt tgataatcat gacaccgaac ccggccaagc gcttcagtca    1020
tgggtcgacc catggttcaa accgttggct tacgcccttta ttctaactcg gcaggaagga   1080
tacccgtgcg tcttttatgg tgactattat ggcattccac aatataacat tccttcgctg   1140
aaaagcaaaa tcgatccgct cctcatcgcg cgcagggatt atgcttacgg aacgcaacat    1200
gattatcttg atcactccga catcatcggg tggacaaggg aagggtcac tgaaaaacca     1260 ggatccgggc tggccgcact gatcaccgat gggccgggag aagcaaatg gatgtacgtt     1320 ggcaaacaac acgctggaaa agtgttctat gaccttaccg gcaaccggag tgacaccgtc    1380
accatcaaca gtgatggatg gggggaattc aaagtcaatg gcggttcggt ttcggtttgg    1440
gttcctagaa aaacgacc                                                  1458

<210> SEQ ID NO 14
<211> LENGTH: 1923
<212> TYPE: DNA
<213> ORGANISM: Aspergillus kawachii

<400> SEQUENCE: 14
atgagagtgt cgacttcaag tattgcccctt gctgtgtccc tttttgggaa gctggccctt     60
gggctgtcag ctgcagaatg gcgcactcaa tccatctact tccttttgac ggatcggttc    120
ggtaggacgg acaattcgac tacagctacg tgcaatacgg gtgaccaaat ctactgtggt    180
ggaagttggc aaggaattat caaccatctg gactatatcc agggcatggg attcacagct    240
atctggatct cgcctatcac tgagcagcta ccccaggata cttcggatgg tgaagcctac    300
catggatact ggcagcagaa gatatacaat gtgaactcca acttcggcac ggcagatgat    360
ctgaagtccc tctccgatgc tcttcacgcc cgcggaatgt acctcatggt cgacgtcgtc    420
cctaaccaca tgggctacgc aggtaacggc aacgatgtgg attacagcgt cttcgacccc    480
ttcgactcct cctcctactt ccatccatac tgcctcatca cagattggga caacttgacc    540
atggtccaag actgttggga gggtgacacc atcgtgtctc tgccagatct gaacaccacg    600
gaaaccgccg tgagaaccat ttggtacgat tgggtagccg acctggtatc caactactca    660
gtcgacggcc tccgtatcga cagtgtcgaa gaagtcgaac ccgacttctt cccgggctac    720
caagaagcag caggagtcta ctgcgtcggt gaagtcgaca cggcaaccc tgctctcgac    780 tgcccatacc aaaaatatct agatggtgtt ctcaactatc ccatctactg gcaactcctc    840 tacgccttg aatcctccag cggcagcatc agcaacctct acaacatgat caaatccgtc    900
gccagcgact gctccgatcc gaccctcctg ggcaacttta tcgaaaacca cgacaacccc    960
cgcttcgcct cctacacatc cgactactcc caagccaaaa acgtcctcag ctacatcttc    1020
ctctccgacg catccccat cgtctacgcc ggcgaagaac agcactactc cggcggcgac   1080 gtgcctaca accgcgaagc tacctggcta tcaggctacg acacctccgc ggagctctac   1140
```

| | |
|---|---|
| acctggatag ccaccacaaa cgcgatccgg aaactagcta tctcagcaga ctcggactac | 1200 |
| attacttacg cgaacgaccc aatctacaca gacagcaaca ccatcgcgat gcgcaaaggc | 1260 |
| acctccggct cccaaatcat caccgtcctc tccaacaaag gctcctccgg aagcagctac | 1320 |
| accctcaccc tcagcggaag cggctacacg tccggcacga agctcatcga agcgtacacc | 1380 |
| tgcacgtccg tgacggtgga ctcgaacggg gatatccctg tgccgatggc ttcgggatta | 1440 |
| cctagagttc tcctccctgc ttcggtggtt gatagttctt cgctttgtgg ggggagtggt | 1500 |
| aacacaacca cgaccacaac tgctgctacc tccacatcca aagccaccac ctcctcttct | 1560 |
| tcttcttctg ctgctgctac tacttcttca tcatgcaccg caacaagcac cccctcccc | 1620 |
| atcaccttcg aagaactcgt caccactacc tacggggaag aagtctacct cagcggatct | 1680 |
| atctcccagc tcggagagtg ggatacgagt gacgcgtga agttgtccgc ggatgattat | 1740 |
| acctcgagta accccgagtg gtctgttact gtgtcgttgc cggtggggac gaccttcgag | 1800 |
| tataagttta ttaaggtcga tgagggtgga agtgtgactt gggaaagtga tccgaatagg | 1860 |
| gagtatactg tgcctgaatg tgggagtggg agtggggaga cggtggttga tacgtggagg | 1920 |
| tag | 1923 |

<210> SEQ ID NO 15
<211> LENGTH: 1899
<212> TYPE: DNA
<213> ORGANISM: Trichoderma reesei

<400> SEQUENCE: 15

| | |
|---|---|
| atgcacgtcc tgtcgactgc ggtgctgctc ggctccgttg ccgttcaaaa ggtcctggga | 60 |
| agaccaggat caagcggtct gtccgacgtc accaagaggt ctgttgacga cttcatcagc | 120 |
| accgagacgc ctattgcact gaacaatctt ctttgcaatg ttggtcctga tggatgccgt | 180 |
| gcattcggca catcagctgg tgcggtgatt gcatctccca gcacaattga cccggactac | 240 |
| tattacatgt ggacgcgaga tagcgctctt gtcttcaaga acctcatcga ccgcttcacc | 300 |
| gaaacgtacg atgcgggcct gcagcgccgc atcgagcagt acattactgc ccaggtcact | 360 |
| ctccagggcc tctctaaccc ctcgggctcc ctcgcgacg gctctggtct cggcgagccc | 420 |
| aagtttgagt tgaccctgaa gcctttcacc ggcaactggg gtcgaccgca gcgggatggc | 480 |
| ccagctctgc gagccattgc cttgattgga tactcaaagt ggctcatcaa caacaactat | 540 |
| cagtcgactg tgtccaacgt catctggcct attgtgcgca acgacctcaa ctatgttgcc | 600 |
| cagtactgga ccaaaaccgg cttttgacctc tgggaagaag tcaatgggag ctcattcttt | 660 |
| actgttgcca accagcaccg agcacttgtc gagggcgcca ctcttgctgc cactcttggc | 720 |
| cagtcgggaa gcgcttattc atctgttgct ccccaggttt tgtgctttct ccaacgattc | 780 |
| tgggtgtcgt ctggtggata cgtcgactcc aacatcaaca ccaacgaggg caggactggc | 840 |
| aaggatgtca actccgtcct gacttccatc cacaccttcg atcccaacct tggctgtgac | 900 |
| gcaggcacct tccagccatg cagtgacaaa gcgctctcca acctcaaggt tgttgtcgac | 960 |
| tccttccgct ccatctacgg cgtgaacaag ggcattcctg ccggtgctgc cgtcgccatt | 1020 |
| ggccggtatg cagaggatgt gtactacaac ggcaacccct tggtatcttg cacatttgct | 1080 |
| gctgccgagc agctgtacga tgccatctac gtctggaaga gacgggctc catcacggtg | 1140 |
| accgccacct ccctggcctt cttccaggag cttgttcctg gcgtgacggc cgggacctac | 1200 |
| tccagcagct cttcgacctt taccaacatc atcaacgccg tctcgacata cgccgatggc | 1260 |
| ttcctcagcg aggctgccaa gtacgtcccc gccgacggtt cgctggccga gcagtttgac | 1320 |

```
cgcaacagcg gcactccgct gtctgcgctt cacctgacgt ggtcgtacgc ctcgttcttg    1380
acagccacgg cccgtcgggc tggcatcgtg ccccctcgt gggccaacag cagcgctagc    1440
acgatcccct cgacgtgctc cggcgcgtcc gtggtcggat cctactcgcg tcccaccgcc    1500
acgtcattcc ctccgtcgca gacgcccaag cctggcgtgc cttccggtac tccctacacg    1560
cccctgccct gcgcgacccc aacctccgtg gccgtcacct ccacgagct cgtgtcgaca    1620 cagtttggcc agacggtcaa ggtggcgggc aacgccgcgg ccctgggcaa ctggagcacg    1680
agcgccgccg tggctctgga cgccgtcaac tatgccgata accacccct gtggattggg    1740 acggtcaacc tcgaggctgg agacgtcgtg gagtacaaga catcaatgt gggccaagat    1800 ggctccgtga cctgggagag tgatcccaac cacacttaca cggttcctgc ggtggcttgt    1860
gtgacgcagg ttgtcaagga ggacacctgg cagtcgtaa                          1899
```

<210> SEQ ID NO 16  
<211> LENGTH: 1449  
<212> TYPE: DNA  
<213> ORGANISM: Artificial  
<220> FEATURE:  
<223> OTHER INFORMATION: Synthetic sequence encoding SEQ ID NO:8

<400> SEQUENCE: 16

```
acaaatctta atgggacgct gatgcagtat tttgaatggt acacgcccaa tgacggccaa      60
cattggaagc gtctgcaaaa cgactcggca tatttggctg aacacggtat tactgccgtc     120
tggattcccc cggcatataa gggaacgagc caagcggatg tgggctacgg tgcttacgac     180
ctttatgatt taggggagtt tcatcaaaaa gggacggttc ggacaaagta cggcacaaaa     240
ggagagctgc aatctgcgat caaaagtctt cattcccgcg acattaacgt ttacggggat     300
gtggtcatca accacaaagg cggcgctgat gcgaccgaag atgtaaccgc ggttgaagtc     360
gatcccgctg accgcaaccg cgtaatttcc ggagaatacc taattaaagc ctggacacat     420
tttcattttc cggggcgcgg cagcacatac agcgatttta atggcattg gtaccatttt     480 gacggaaccg attgggacga gtcccgaaag ctgaaccgca tctataagtt tcaaggaaag     540
gcttgggatt gggaagtttc cagtgaaaac ggcaactatg attatttgat gtatgccgac     600
atcgattatg accatcctga tgtcgtagca gaaattaaga gatggggcac ttggtatgcc     660
aatgagctcc aattggacgg tttccgtctt gatgctgtca aacacattaa atttctcttt     720
ttgcgggatt gggttaatca tgtcagggaa aaacgggga aggaaatgtt tacggtagct     780
gaatattggc agaatgactt gggcgcgctg aaaactatt tgaacaaaac aaatttaat    840 cattcagtgt tgacgtgcc gcttcattat cagttccatg ctgcatcgac acaggaggc     900 ggctatgata tgaggaaatt gctgaacggt acggtcgttt ccaagcatcc gttgaaatcg     960
gttacatttg tcgataacca tgatacacag ccggggcagt cgcttgagtc gactgtccaa    1020
acatggttta agccgcttgc ttacgctttt attctcacaa gggaatctgg ataccctcag    1080
gttttctacg gggatatgta cgggacgaaa ggagactccc agcgcgaaat tcctgccttg    1140
aaacacaaaa ttgaaccgat cttaaaagcg agaaaacagt atgcgtacgg agcacagcat    1200
gattatttcg accaccatga cattgtcggc tggacaaggg aaggcgacag ctcggttgca    1260
aattcaggtt tggcggcatt aataacagac ggacccggtg gggcaaagcg aatgtatgtc    1320
ggccggcaaa acgccggtga gacatggcat gacattaccg aaaaccgttc ggagccggtt    1380
gtcatcaatt cggaaggctg gggagagttt cacgtaaacg gcgggtcggt ttcaatttat    1440
``` gttcaaaga                                                          1449

<210> SEQ ID NO 17
<211> LENGTH: 41
<212> TYPE: PRT
<213> ORGANISM: Bacillus subtilis

<400> SEQUENCE: 17

Met Phe Ala Lys Arg Phe Lys Thr Ser Leu Leu Pro Leu Phe Ala Gly
1               5                   10                  15

Phe Leu Leu Leu Phe His Leu Val Leu Ala Gly Pro Ala Ala Ala Ser
            20                  25                  30

Ala Glu Thr Ala Asn Lys Ser Asn Glu
        35                  40

<210> SEQ ID NO 18
<211> LENGTH: 60
<212> TYPE: DNA
<213> ORGANISM: Artificial
<220> FEATURE:
<223> OTHER INFORMATION: Synthetic primer

<400> SEQUENCE: 18
cttcttgctg cctcattctg cagcttcagc acttacagca ccgtcgatca aaagcggaac      60

<210> SEQ ID NO 19
<211> LENGTH: 57
<212> TYPE: DNA
<213> ORGANISM: Artificial
<220> FEATURE:
<223> OTHER INFORMATION: Synthetic primer

<400> SEQUENCE: 19
ctggaggcac tatcctgaag gatttctccg tattggaact ctgctgatgt atttgtg        57

<210> SEQ ID NO 20
<211> LENGTH: 57
<212> TYPE: DNA
<213> ORGANISM: Artificial
<220> FEATURE:
<223> OTHER INFORMATION: Synthetic primer

<400> SEQUENCE: 20
cacaaataca tcagcagagt tccaatacgg agaaatcctt caggatagtg cctccag        57

<210> SEQ ID NO 21
<211> LENGTH: 56
<212> TYPE: DNA
<213> ORGANISM: Artificial
<220> FEATURE:
<223> OTHER INFORMATION: Synthetic primer

<400> SEQUENCE: 21
caggaaatcc gtcctctgtt aactcaatgg ggaagagaac cgcttaagcc cgagtc         56

<210> SEQ ID NO 22
<211> LENGTH: 55
<212> TYPE: DNA
<213> ORGANISM: Artificial
<220> FEATURE:
<223> OTHER INFORMATION: Synthetic primer

<400> SEQUENCE: 22
caggaaatcc gtcctctgtt aactcaatca ggataaagca cagctacaga cctgg          55

```
<210> SEQ ID NO 23
<211> LENGTH: 22
<212> TYPE: DNA
<213> ORGANISM: Artificial
<220> FEATURE:
<223> OTHER INFORMATION: Synthetic primer

<400> SEQUENCE: 23
tacacaagta cagtcctatc tg                                            22

<210> SEQ ID NO 24
<211> LENGTH: 22
<212> TYPE: DNA
<213> ORGANISM: Artificial
<220> FEATURE:
<223> OTHER INFORMATION: Synthetic primer

<400> SEQUENCE: 24
catcctctgt ctctatcaat ac                                            22

<210> SEQ ID NO 25
<211> LENGTH: 618
<212> TYPE: PRT
<213> ORGANISM: Bacillus subtilis

<400> SEQUENCE: 25
```

Val Thr Ala Ser Ser Val Lys Asn Gly Thr Ile Leu His Ala Trp Asn
1               5                   10                  15

Trp Ser Phe Asn Thr Leu Thr Gln Asn Met Lys Asp Ile Arg Asp Ala
            20                  25                  30

Gly Tyr Ala Ala Ile Gln Thr Ser Pro Ile Asn Gln Val Lys Glu Gly
        35                  40                  45

Asn Gln Gly Asp Lys Ser Met Ser Asn Trp Tyr Trp Leu Tyr Gln Pro
    50                  55                  60

Thr Ser Tyr Gln Ile Gly Asn Arg Tyr Leu Gly Thr Glu Gln Glu Phe
65                  70                  75                  80

Lys Asp Met Cys Ala Ala Ala Glu Lys Tyr Gly Val Lys Val Ile Val
                85                  90                  95

Asp Ala Val Val Asn His Thr Thr Ser Asp Tyr Gly Ala Ile Ser Asp
            100                 105                 110

Glu Ile Lys Arg Ile Pro Asn Trp Thr His Gly Asn Thr Gln Ile Lys
        115                 120                 125

Asn Trp Ser Asp Arg Trp Asp Ile Thr Gln Asn Ala Leu Leu Gly Leu
    130                 135                 140

Tyr Asp Trp Asn Thr Gln Asn Thr Glu Val Gln Ala Tyr Leu Lys Gly
145                 150                 155                 160

Phe Leu Glu Arg Ala Leu Asn Asp Gly Ala Asp Gly Phe Arg Tyr Asp
                165                 170                 175

Ala Ala Lys His Ile Glu Leu Pro Asp Asp Gly Asn Tyr Gly Ser Gln
            180                 185                 190

Phe Trp Pro Asn Ile Thr Asn Thr Ser Ala Glu Phe Gln Tyr Gly Glu
        195                 200                 205

Ile Leu Gln Asp Ser Ala Ser Arg Asp Thr Ala Tyr Ala Asn Tyr Met
    210                 215                 220

Asn Val Thr Ala Ser Asn Tyr Gly His Ser Ile Arg Ser Ala Leu Lys
225                 230                 235                 240

Asn Arg Ile Leu Ser Val Ser Asn Ile Ser His Tyr Ala Ser Asp Val
                245                 250                 255

```
Ser Ala Asp Lys Leu Val Thr Trp Val Glu Ser His Asp Thr Tyr Ala
            260                 265                 270
Asn Asp Asp Glu Glu Ser Thr Trp Met Ser Asp Asp Ile Arg Leu
            275                 280             285
Gly Trp Ala Val Ile Gly Ser Arg Gly Ser Thr Pro Leu Phe Phe
        290                 295                 300
Ser Arg Pro Glu Gly Gly Gly Asn Gly Val Arg Phe Pro Gly Lys Ser
305                 310                 315                 320
Gln Ile Gly Asp Arg Gly Ser Ala Leu Phe Lys Asp Gln Ala Ile Thr
                325                 330                 335
Ala Val Asn Gln Phe His Asn Glu Met Ala Gly Gln Pro Glu Glu Leu
            340                 345                 350
Ser Asn Pro Asn Gly Asn Asn Gln Ile Phe Met Asn Gln Arg Gly Ser
            355                 360                 365
Lys Gly Val Val Leu Ala Asn Ala Gly Ser Ser Val Thr Ile Asn
        370                 375                 380
Thr Ser Thr Lys Leu Pro Asp Gly Arg Tyr Asp Asn Arg Ala Gly Ala
385                 390                 395                 400
Gly Ser Phe Gln Val Ala Asn Gly Lys Leu Thr Gly Thr Ile Asn Ala
                405                 410                 415
Arg Ser Ala Ala Val Leu Tyr Pro Asp Asp Ile Gly Asn Ala Pro His
            420                 425                 430
Val Phe Leu Glu Asn Tyr Gln Thr Glu Ala Val His Ser Phe Asn Asp
            435                 440                 445
Gln Leu Thr Val Thr Leu Arg Ala Asn Ala Lys Thr Thr Lys Ala Val
        450                 455                 460
Tyr Gln Ile Asn Asn Gly Gln Glu Thr Ala Phe Lys Asp Gly Asp Arg
465                 470                 475                 480
Leu Thr Ile Gly Lys Glu Asp Pro Ile Gly Thr Thr Tyr Asn Val Lys
                485                 490                 495
Leu Thr Gly Thr Asn Gly Glu Gly Ala Ser Arg Thr Gln Glu Tyr Thr
            500                 505                 510
Phe Val Lys Lys Asp Pro Ser Gln Thr Asn Ile Ile Gly Tyr Gln Asn
        515                 520                 525
Pro Asp His Trp Gly Asn Val Asn Ala Tyr Ile Tyr Lys His Asp Gly
        530                 535                 540
Gly Gly Ala Ile Glu Leu Thr Gly Ser Trp Pro Gly Lys Ala Met Thr
545                 550                 555                 560
Lys Asn Ala Asp Gly Ile Tyr Thr Leu Thr Leu Pro Ala Asn Ala Asp
                565                 570                 575
Thr Ala Asp Ala Lys Val Ile Phe Asn Asn Gly Ser Ala Gln Val Pro
            580                 585                 590
Gly Gln Asn His Pro Gly Phe Asp Tyr Val Gln Asn Gly Leu Tyr Asn
            595                 600                 605
Asn Ser Gly Leu Asn Gly Tyr Leu Pro His
        610                 615
```